US007025813B2

United States Patent
(12) United States Patent
Vanmaele et al.

(10) Patent No.: US 7,025,813 B2
(45) Date of Patent: Apr. 11, 2006

(54) INK COMPOSITION CONTAINING A PARTICULAR TYPE OF DYE, AND CORRESPONDING INK-JET PRINTING PROCESS

(75) Inventors: Luc Vanmaele, Lochristi (BE); Johan Loccufier, Zwijnaarde (BE); Egbert Meijer, Waalre (NL); Henricus Janssen, Eindhoven (NL); Pieter Fransen, Boxtel (NL)

(73) Assignee: AGFA-Gevaert, Mortsel (BE)

( * ) Notice: Subject to any disclaimer, the term of this patent is extended or adjusted under 35 U.S.C. 154(b) by 84 days.

(21) Appl. No.: 10/844,114

(22) Filed: May 12, 2004

(65) Prior Publication Data

US 2004/0206270 A1 Oct. 21, 2004

Related U.S. Application Data

(63) Continuation-in-part of application No. 10/266,297, filed on Oct. 8, 2002, now abandoned.

(60) Provisional application No. 60/336,310, filed on Oct. 31, 2001.

(30) Foreign Application Priority Data

Oct. 25, 2001 (EP) .................................. 01000574

(51) Int. Cl.
*C09D 11/00* (2006.01)
*C09D 11/02* (2006.01)
*B41J 2/01* (2006.01)

(52) U.S. Cl. .............................. 106/31.27; 106/31.43; 106/31.47; 106/31.58; 347/100

(58) Field of Classification Search ............ 106/31.27, 106/31.43, 31.47, 31.58; 347/100
See application file for complete search history.

(56) References Cited

U.S. PATENT DOCUMENTS

| | | | | |
|---|---|---|---|---|
| 3,889,271 | A | 6/1975 | Freytag et al. | 346/1 |
| 5,736,535 | A * | 4/1998 | Bernstein et al. | 514/64 |
| 6,057,384 | A * | 5/2000 | Nguyen et al. | 523/160 |
| 6,803,447 | B1 * | 10/2004 | Janssen et al. | 528/423 |
| 6,827,768 | B1 * | 12/2004 | Andrievsky et al. | 106/31.27 |
| 6,855,193 | B1 * | 2/2005 | Andrievsky et al. | 106/31.27 |
| 2002/0149656 | A1 | 10/2002 | Nohr et al. | 347/95 |
| 2003/0021983 | A1 | 1/2003 | Nohr et al. | 428/327 |
| 2004/0045477 | A1 | 3/2004 | Andrievsky | 106/31.27 |
| 2004/0050290 | A1 | 3/2004 | Andrievsky | 106/31.27 |
| 2005/0051052 | A1 * | 3/2005 | Vanmaele et al. | 106/31.47 |

OTHER PUBLICATIONS

Derwent ACC No.: 2004-125942, 200428, Agfa-Gevaert, JP2003206424 Jul. 22, 2003.

* cited by examiner

*Primary Examiner*—Helene Klemanski
(74) *Attorney, Agent, or Firm*—Joseph T. Guy; Nexsen Pruet LLC

(57) ABSTRACT

An ink composition is disclosed which contains at least one novel dye $(CU)_n(SAU)_m$ that is capable of self-assembling under appropriate conditions to form supramolecular structures. More than one novel dye $(CU)_n(SAU)_m$ and/or at least one non-colored self-assembling compound $(SAU')_p(X)_q$ may be incorporated in these supramolecular structures. Also disclosed is an ink-jet printing process using these novel dyes, and an ink-jet printing apparatus provided with an ink cartridge containing such a dye.

49 Claims, No Drawings

INK COMPOSITION CONTAINING A PARTICULAR TYPE OF DYE, AND CORRESPONDING INK-JET PRINTING PROCESS

CROSS-REFERENCE TO RELATED PATENT APPLICATIONS

This application is a continuation-in-part of application Ser. No. 10/266,297, filed Oct. 8, 2002 now abandoned, which claims the benefit of U.S. Provisional Application No. 60/336,310 filed Oct. 31, 2001, which is incorporated by reference. In addition, this application claims the benefit of European Application No. 01000574.2 filed Oct. 25, 2001, which is also incorporated by reference.

FIELD OF THE INVENTION

The present invention relates to ink compositions comprising a particular type of novel dye. It further relates to an ink-jet printing process using these dyes, and to an ink-jet printing apparatus provided with an ink cartridge containing such a dye.

BACKGROUND OF THE INVENTION

In the majority of applications printing proceeds by pressure contact of an ink-laden printing form with an ink-receiving material which is usually plain paper. The most frequently used impact printing technique is known as lithographic printing based on the selective acceptance of oleophilic ink on a suitable receptor.

In recent times however so-called non-impact printing systems have replaced classical pressure-contact printing to some extent for specific applications. A survey is given e.g. in the book "Principles of Non Impact Printing" by Jerome L. Johnson (1986), Palatino Press, Irvine, Calif. 92715, USA.

Among non-impact printing techniques ink-jet printing has become a popular technique because of its simplicity, convenience and low cost. Especially in those instances where a limited edition of the printed matter is needed, ink-jet printing has become a technology of choice. A recent survey on progress and trends in ink-jet printing technology is given by Hue P. Le in *Journal of Imaging Science and Technology* Vol. 42 (1), January/February 1998.

In ink-jet printing tiny drops of ink fluid are projected directly onto an ink-receiver surface without physical contact between the printing device and the ink-receiver. The printing device stores the printing data electronically and controls a mechanism for ejecting the ink drops image-wise onto the ink-receiver. Printing can be accomplished by moving a print head across the ink-receiver or vice versa. Early patents on ink-jet printers include U.S. Pat. Nos. 3,739,393, 3,805,273 and 3,891,121.

The jetting of the ink droplets can be performed in several different ways. In a first type of process called continuous ink-jet printing, the ink stream jetted from an orifice of the print head is broken up, by applying a pressure wave pattern to this orifice, into ink droplets of uniform size and spacing. When the jet break-up mechanism is controlled, an electric charge can be applied to the droplets selectively and reliably as they form from the continuous ink stream. The charged drops passing through an electric field are deflected into a gutter for recuperation, while the uncharged drops proceed directly onto the ink-receiver to form an image or vice versa.

According to a second process the ink droplets can be created by a "drop on demand" method (DOD). A drop-on-demand device ejects ink droplets only when they are needed for imaging on the ink-receiver, thereby avoiding the complexity of drop charging, deflection hardware, and ink collection. In drop-on-demand ink-jet printing, the ink droplet can be formed by means of a pressure wave created by the mechanical motion of a piezoelectric transducer (so-called "piezo method"), or by means of discrete thermal pulses (so-called "bubble jet" method, or "thermal jet" method).

Ink receiving layers for ink-jet recording media are either non-absorptive or absorptive. In absorptive ink-receiving layers the ink is either absorbed by swelling of the layer due to the specific polymers present in the layer, or is absorbed by capillarity, due to the microporous character of the layer.

It is known that the ink-receiving layers in ink-jet recording elements must meet different stringent requirements:

- the ink-receiving layer should have a high ink absorbing capacity, so that the dots will not flow out and will not increase in size more than is necessary to obtain a high optical density;
- the ink-receiving layer should have a high ink absorbing speed (short ink drying time) so that the ink-droplets will not feather if touched immediately after application;
- the ink dots that are applied to the ink-receiving layer should be substantially round in shape and smooth at their peripheries. The dot diameter must be constant and accurately controlled;
- the receiving layer must be readily wetted so that there is no "puddling", i.e. coalescence of adjacent ink dots, and an previously absorbed ink drop should not show any "bleeding", i.e. overlap with neighbouring or later placed dots;
- transparent ink-jet recording elements must have a low haze-value and exhibit excellent transmittance properties;
- after being printed the image must have a good resistance regarding water-fastness, light-fastness, and be stable to extreme conditions of temperature and humidity;
- the ink-jet recording material must not show any curl or sticky behavior if stacked before or after being printed;
- the ink-jet recording element must be able to move smoothly through different types of printers.

All these properties are often in a trade-off relationship with one another, as it is difficult to satisfy them all at the same time.

It will be readily understood that the optimal composition of an ink is dependent on the ink jetting method used and on the nature of the ink-receiver to be printed.

Ink compositions for ink-jet typically include the following ingredients: dyes or pigments, water and/or organic solvents, humectants such as glycols, detergents, thickeners, polymeric binders, preservatives, etc.

Ink compositions can be roughly divided into:

- water based, the drying mechanism involving absorption, penetration and evaporation;
- oil based, the drying involving absorption and penetration;
- solvent based, the drying mechanism involving primarily evaporation;
- hot melt or phase change, in which the ink is liquid at the ejection temperature but solid at room temperature and wherein drying is replaced by solidification;
- UV-curable, in which drying is replaced by polymerization.

U.S. Pat. No. 5,919,846 discloses a compound comprising the addition product of (a) an organic chromophore having at least one reactive hydroxyl or amine substituent group; (b) a polyisocyanate; and (c) a carboxylic acid, sulfonic acid, or salt of either thereof having at least one reactive hydroxyl or amine substituent group; wherein the polyisocyanate reacts with each of the reactive hydroxyl or amine substituent groups to form isocyanate terminal groups on the organic chromophore and, subsequently, the carboxylic acid or salt thereof reacts with the isocyanate terminal groups to form urethane or urea moieties on the resulting compound.

U.S. Pat. No. 5,852,072 discloses an erasable ink composition which comprises a waterborne polyurethane-urea obtained by effecting polymerization of a waterborne polyurethane-urea-forming reaction medium containing at least two coreactive polyfunctional monomers, said waterborne polyurethane urea containing dye moiety covalently bonded thereto, the erasable ink composition when applied to a substrate and upon drying thereon exhibiting less than about 30 weight percent flaking based on the weight of the dried ink and an erasability value delta E*ab of less than about 4.0.

EP 816,410 discloses an isocyanate-derived colored resin comprising the reaction product of: (a) an isocyanate; and (b) at least one chromogen-containing nucleophile.

WO 96/18687 discloses an erasable ink composition which comprises (a) a water-insoluble polymer dye obtained by affecting polymerization of a polymer-forming reaction medium containing at least two coreactive polyfunctional monomers with at least one of the monomers possesing a dye moiety covalently bonded thereto and (b) and evaporable liquid carrier in which the polymer dye is dissolved, dispersed or swollen, the erasable ink composition when applied to a substrate and upon drying theron being (1) sufficiently adherent to the substrate as to resist flaking therefrom and (2) substantially erasable.

U.S. Pat. No. 5,413,630 discloses aqueous ink compositions for ink jet printing which comprises water, a humectant, and specific types of colorants.

It is also known that dyes used in inks for ink-jet printing must meet different stringent requirements. For example they are required to provide sharp, non-feathered images having good water-fastness, solvent fastness, light-fastness and optical density. Their solubility must be fine-tuned to the vehicle they are dissolved in. Preferably they have high molecular extinction coefficients. In spite of the many dyes that already exist for application in ink-jet inks, there is still a continuous search for novel dyes and especially for dyes with an improved light-fastness and stability towards (singlet)oxygen, ozone and air pollutants such as sulfur oxides (SOx) and nitrogen oxides (NOx).

OBJECTS OF THE INVENTION

It is an object of the present invention to provide novel ink compositions containing novel dyes for producing ink-jet images exhibiting improved light-fastness.

It is a further object of the present invention to provide an ink-jet printing process using these ink compositions.

It is still a further object of the present invention to provide an ink-jet apparatus comprising a cartridge containing these ink compositions.

Further objects of the invention will become clear from the detailed description hereinafter.

SUMMARY OF THE INVENTION

It has been surprisingly found that the presence of self-assembling dyes according to formula (I):

$$(CU)_n(SAU)_m \qquad (I)$$

wherein,

CU means a chromophore group with an absorption maximum between 200 nm and 2000 nm which is covalently linked to SAU;

SAU means a multiple H-donor/accepting group, which can form at least three hydrogen bonds;

n and m are at least 1;

when n is greater than 1 the individual CU groups may be the same or different; and when m is greater than 1 the individual SAU groups may be the same or different;

in ink-jet images results in a substantial improvement in the stability of ink-jet ink images to light fading.

The above mentioned objects are realized by providing an ink composition comprising at least one self-assembling dye according to formula (I) as described above.

The above mentioned objects are also realized by providing a process for use of an ink composition comprising at least one self-assembling dye according to formula (I) as described above.

The above mentioned objects are also realized by providing an ink-jet apparatus comprising a cartridge containing an ink composition comprising at least one self-assembling dye according to formula (I) as described above.

DETAILED DESCRIPTION OF THE INVENTION

Definitions

The term "self-assembly" as used in disclosing the present invention means the method of association in which individual molecules spontaneously associate upon Brownian movement in a solvent or gas phase until a stable structure of minimum energy is formed by means of hydrogen bonding.

The abbreviation "SAU" is used for Self-Assembling Unit, which is a part of a molecular structure capable of self-assembly by forming at least three hydrogen bonds.

The term "chromophore group" as used in disclosing the present invention means a part of a molecular structure capable of absorbing light from the visible spectrum and imparting color to other materials, e.g. an ink-jet ink or an ink-jet receiver. The abbreviation "CU" is used for chromophore group.

The term "self-assembling dye" as used in disclosing the present invention means a dye comprising in its molecular structure covalently bonded to each other in any manner at least one SAU and at least one chromophore group, CU.

The term "dye system" as used in disclosing the present invention means a self-assembled structure consisting of one or more self-assembling dyes and/or self-assembling non-dye compounds.

The term "reference dye" as used in disclosing the present invention means a dye that contains no SAU.

The term "vehicle" as used in disclosing the present invention means a medium for dissolving the self-assembling dye, e.g. water, an organic solvent or an oil.

The term "alkyl" as used in disclosing the present invention means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethylpropyl, 2,2-dimethylpropyl and 2-methyl-butyl etc.

The term "acyl group" as used in disclosing the present invention means —(C═O)-aryl and —(C═O)-alkyl groups.

The term "saturated aliphatic group" as used in disclosing the present invention means saturated straight chain, branched chain and alicyclic hydrocarbon groups.

The term "unsaturated aliphatic group" as used in disclosing the present invention means straight chain, branched chain and alicyclic hydrocarbon groups which contain at least one double or triple bond.

The term "aromatic group" as used in disclosing the present invention means a covalently bonded assemblage of cyclic conjugated carbon atoms, which are characterized by large resonance energies, e.g. benzene, naphthalene and anthracene.

The term "alicyclic hydrocarbon group" means a covalently bonded assemblage of cyclic conjugated carbon atoms, which do not form an aromatic group, e.g. cyclohexane.

The term "substituted" as used in disclosing this invention means that one or more of the carbon atoms and/or that a hydrogen atom of one or more of the carbon atoms in an aliphatic group, an aromatic group or an alicyclic hydrocarbon group, are replaced by an oxygen atom, a nitrogen atom, a phosphorous atom, a silicon atom, a sulfur atom, a selenium atom or a tellurium atom, or a group containing one or more of these said carbon and hydrogen replacing atoms. Such substituents include hydroxyl groups, thiol groups, carbamate groups, urea groups, ether groups, thioether groups, carboxylic acid groups, ester groups, sulphonate groups, sulphonamide groups, phosphonate groups, phosphonamide groups, phosphonamidate groups, amide groups and amine groups.

The term "heteroaromatic group" means an aromatic group wherein at least one of the cyclic conjugated carbon atoms is replaced by a nitrogen atom or a phosphorous atom.

The term "heterocyclic group" means an alicyclic hydrocarbon group wherein at least one of the cyclic conjugated carbon atoms is replaced by an oxygen atom, a nitrogen atom, a phosphorous atom, a silicon atom, a sulfur atom, a selenium atom or a tellurium atom.

Self-assembling Dyes

Objects of the present invention are realized with an ink composition comprising at least one self-assembling dye according to formula (I)

$$(CU)_n(SAU)_m \quad (I)$$

wherein,

CU means a chromophore group with an absorption maximum between 200 nm and 2000 nm which is covalently linked to SAU;

SAU means a multiple H-donor/accepting group, which can form at least three hydrogen bonds;

n and m are at least 1;

when n is greater than 1 the individual CU groups may be the same or different; and when m is greater than 1 the SAU groups may be the same or different.

In a preferred embodiment of the present invention the ink composition, according to the present invention, further contains at least one self-assembling non-dye compound according to formula (II):

$$(SAU')_p(X)_q \quad (II)$$

wherein, SAU' means a multiple H-donor/accepting group covalently linked to X;

X represents hydrogen, a halogen, a substituted or unsubstituted alkoxy group, a substituted or unsubstituted thioalkoxy group, a substituted or unsubstituted sulphoxy group, a substituted or unsubstituted sulphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group or a heterocyclic group;

p and p are at least 1;

q is 0 or 1;

when p is greater than 1 the SAU' groups may be the same or different, with it being particularly preferred that said at least one of said self-assembling dyes present in said ink composition is capable of self-assembling with at least one of said self-assembling non-dye compounds according to formula (II) present in said ink composition.

In a further preferred embodiment of the present invention the ink composition contains at least two self-assembling dyes according to formula (I), which in a particularly preferred embodiment are capable of self-assembling with one another.

For each case described above the association constant of the assembly reaction $K_{ass}$, determined by $^1$H-NMR in $CDCl_3$, is at least 2.5 $M^{-1}$, more preferably at least $10^2$ $M^{-1}$, and most preferably at least $10^5$ $M^{-1}$.

In a preferred embodiment of the present invention the ink composition, according to the present invention, the at least one self-assembling dye is a dye according to formula (III):

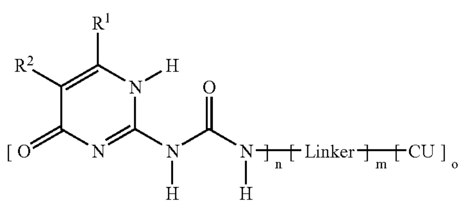

wherein

Linker represents any linking group containing at least one carbon, silicon, nitrogen, phosphorous, sulfur or oxygen atom;

CU means any dye chosen from the group consisting of an azo dye with a molar extinction coefficient larger than $10^3$ l $mol^{-1}$ $cm^{-1}$, an anthraquinone dye, a (poly)methine dye, an azomethine dye, a disazo dye, a carbonium dye, a styryl dye, a stilbene dye, a phthalocyanine dye, a coumarin dye, an aryl-carbonium dye, a nitro dye, a naphtholactam dye, a dioxazine dye, a flavin dye and a formazan dye;

n and o are the same or different and are integers having a value of at least 1; m can be zero or any integer having a value of at least 1;

$R^1$ and $R^2$ are the same or different and represent hydrogen, a halogen, a substituted or unsubstituted alkoxy group, a substituted or unsubstituted thioalkoxy group, a substituted or unsubstituted sulphoxy group, a substituted or unsubstituted sulphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group, a heterocyclic group, a chromophore group, or $R^1$ and $R^2$ represent the necessary atoms to form a ring system.

CU means any chromophore group with an absorption maximum between 200 nm and 2000 nm. Preferred chromophore groups are those that absorb light between 300 nm and 1200 nm. Most preferred are chromophore groups absorbing light between 380 nm and 850 nm.

The Linker is preferably selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group.

Preferably n and o are integers independently selected from the range 1 to 100, more preferably integers selected from the range 1 to 10, and particularly preferably integers selected from the range 1 to 5. Preferably m is an integer selected from the range 1 to 10, and particularly preferably selected from the range 1 to 5.

The nature of the vehicle used in the composition or ink to be formulated will determine the nature of the functional groups to be incorporated into the CU-fragment. This is different for water based, oil based, solvent based, UV-curable or hot melt inks.

The present invention is not limited to any type of CU-fragment and any dye provided with the necessary reactive group(s) can be used for the CU-fragment. They may be of any chemical class such as azo dyes, anthraquinone dyes, (poly)methine dyes, azomethine dyes, disazo dyes, carbonium dyes, polyene dyes, pyrene dyes, styryl dyes, stilbene dyes, phthalocyanine dyes, coumarin dyes, aryl-carbonium dyes, nitro dyes, naphtholactam dyes, dioxazine dyes, formazan dyes and flavin dyes. Suitable examples include dyes mentioned in:

The Colour Index International

Organic Chemistry in Colour, P. F. Gordon, P. Gregory

Color Chemistry, Heinrich Zollinger, Second revised edition

Colour Chemistry, The design and synthesis of organic dyes and pigments, A. T. Peters, H. S. Freeman Advances in Color Chemistry Series, Volume 3; Modern Colourants, Synthesis and Structure, A. T. Peters, H. S. Freeman Organic Colorants, A Handbook of Data of Selected Dyes for Electro-Optical Applications, M. Okawara, T. Kitao, T. Hirashima, M. Matsuoka Studies in Organic Chemistry 40, Photochromism, Molecules and Systems, Heinz Dürr and in the following U.S. Pat. Nos.:

5,510,225, 5,422,334, 5,122,499, 5,571,765, 5,169,828, 5,589,316, 5,366,951, 5,324,601, 5,514,638, 5,455,218, 5,420,097, 5,432,040, 5,665,677, 5,116,806, 5,391,536, 5,314,860, 5,438,030, 5,026,677, 5,397,762, 5,324,621, 5,326,666, 5,043,316, 4,987,119, 5,565,403, 5,021,393, 5,082,823, 5,246,908, 5,326,676, 5,518,984, 4,985,395, 5,356,857, 5,547,815, 5,476,935, 5,084,432, 5,595,574, 5,753,352, 5,468,258, 5,514,516, 5,698,364, 5,489,568, 5,468,870, 5,514,819, 5,571,289, 5,037,731, 5,229,353, 5,371,228, 5,463,045, 5,587,268, 5,616,697, 5,142,089, 5,328,887, 5,438,122

SAU is a multiple H-donor/acceptor unit, which can form at least three hydrogen bonds. The multiple H-donor/acceptor systems according to the present invention are preferably triple and quadruple hydrogen bonding systems, e.g. ureidopyrimidone systems, aminopyrimidine systems, aminopyridine systems, imide systems, aminotriazine systems, barbituric acid systems, urea based systems, uric acid based systems and saccharide based systems; other preferred examples of molecularly self-assembling units containing at least one multiple H-donor/acceptor system according to the present invention can be found in, but are not limited to: Chem. Soc. Rev., 2001, 30, 83–93; Tetrahedron, 57(2001), 1139–1159; J. Am. Chem. Soc., 2001, 123, 409–416; Adv. Mater. 2000, 12, no. 12, 874–878; Chem. Eur. J., 2001, 7, No. 10, 2059–2065; J. Am. Chem. Soc., 2000, 122, 5006–5007; Chem. Eur. J., 2000, 6, No. 21, 3871–3886; Tetrahedron, 56(2000), 8419–8427; WO 98/14504; Monographs in Supramolecular Chemistry, No. 7 Self-Assembly in Supramolecular Systems, L. F. Lindoy, I. M. Atkinson, especially the examples mentioned in Chapter 3; New Polymers based on the Quadruple Hydrogen Bonding Motif, Brigitte J. B. Folmer, Ph.D. Thesis, June 2000, T U Eindhoven; J. Org. Chem., 2001, 66, 6513–6522; Tetrahedron Letters, 42(2001), 7357–7359; Chemistry Letters, 2001, 7, 694.

The dyes according to the present invention can be prepared using synthetic methods known to those who are skilled in the art of organic synthesis. By way of example the synthesis of several dyes according to the present invention is described in the Examples.

Suitable examples of dyes according to the present invention are shown in Table 1.

TABLE 1

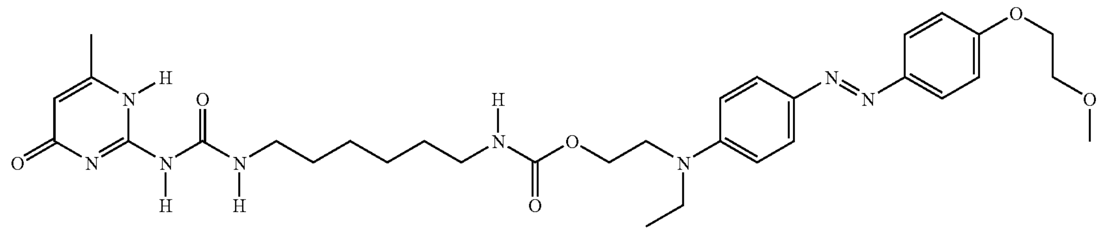

Dye 1

TABLE 1-continued
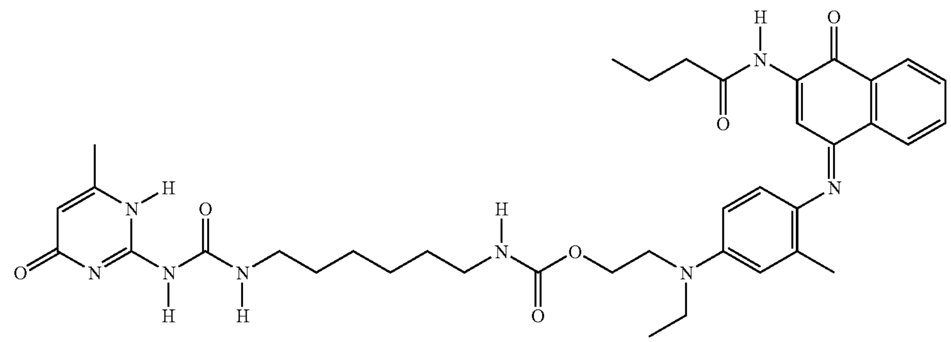
Dye 2
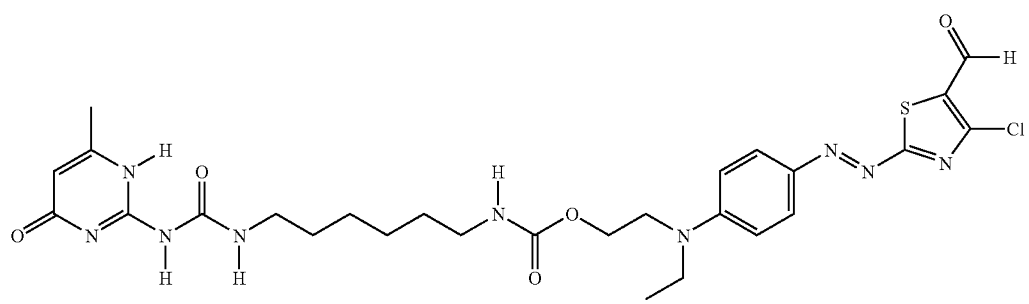
Dye 3
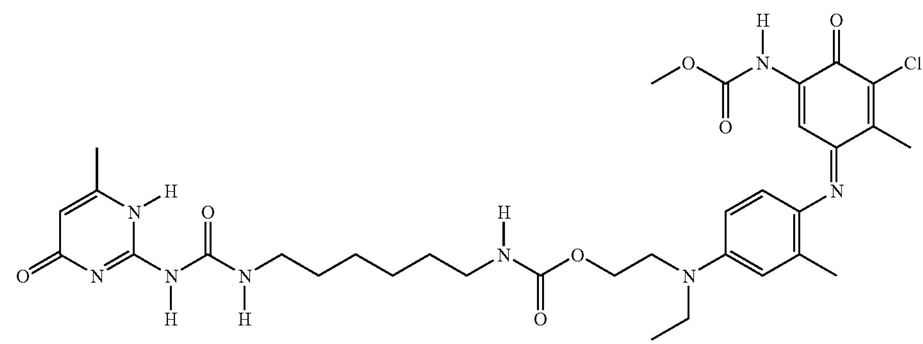
Dye 4
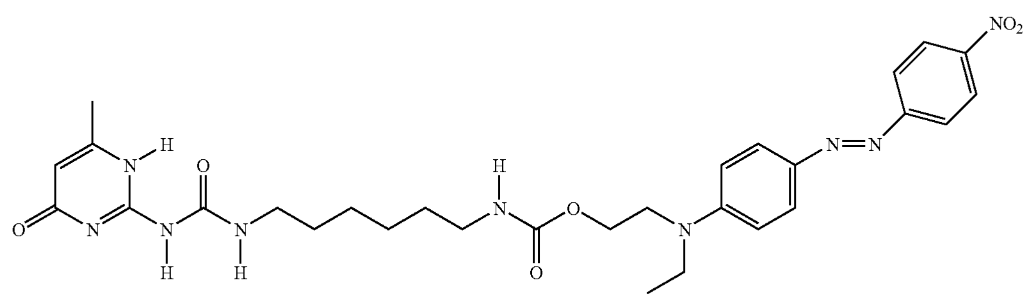
Dye 5

TABLE 1-continued
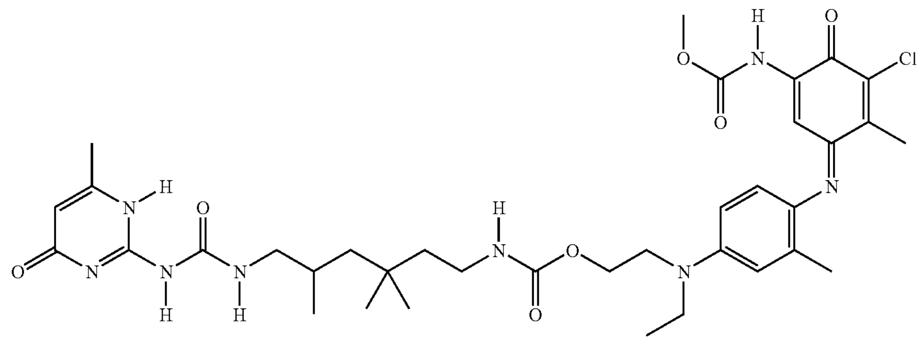
Dye 6
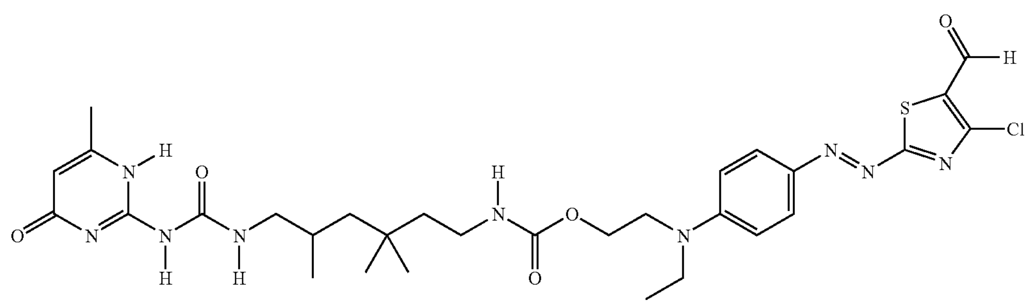
Dye 7
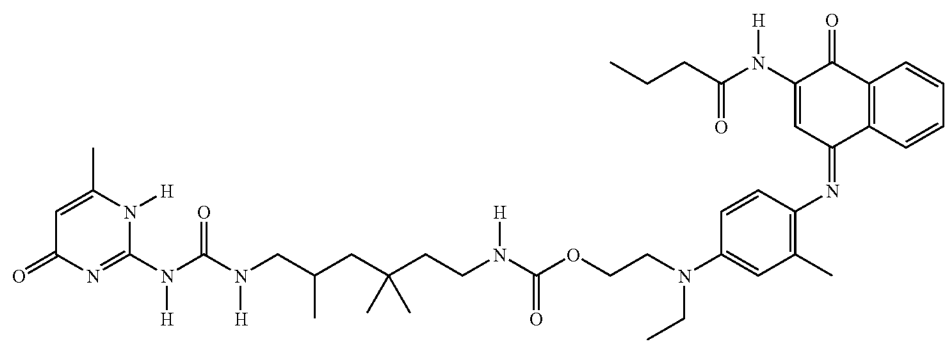
Dye 8
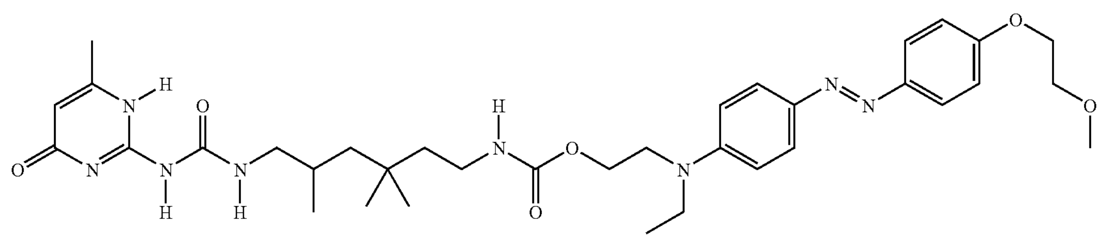
Dye 9

TABLE 1-continued
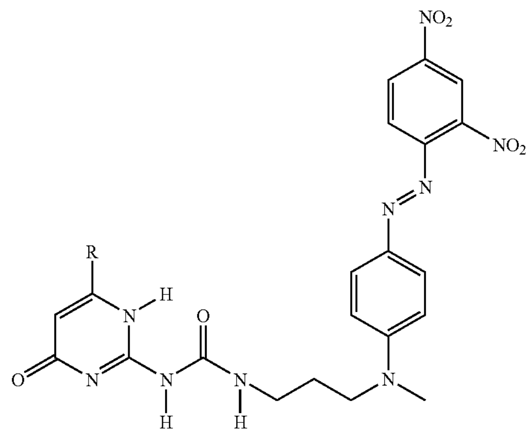
Dye 10
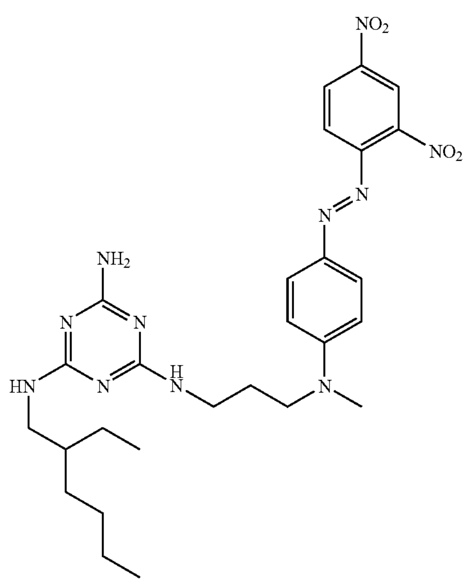
Dye 11
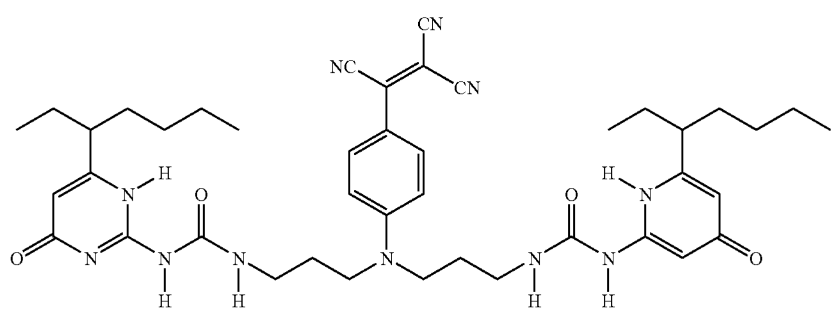
Dye 12

TABLE 1-continued
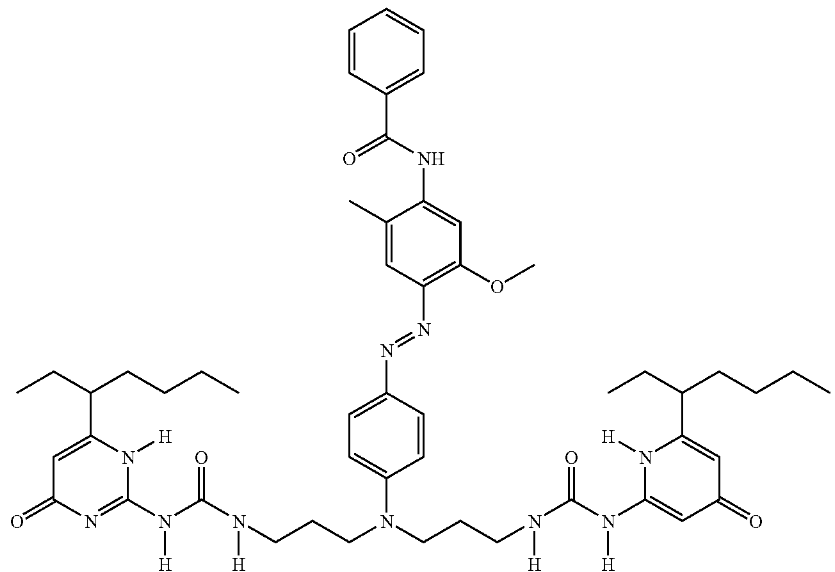
Dye 13
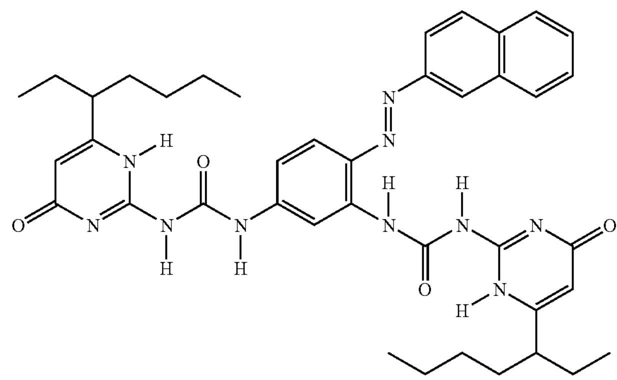
Dye 14
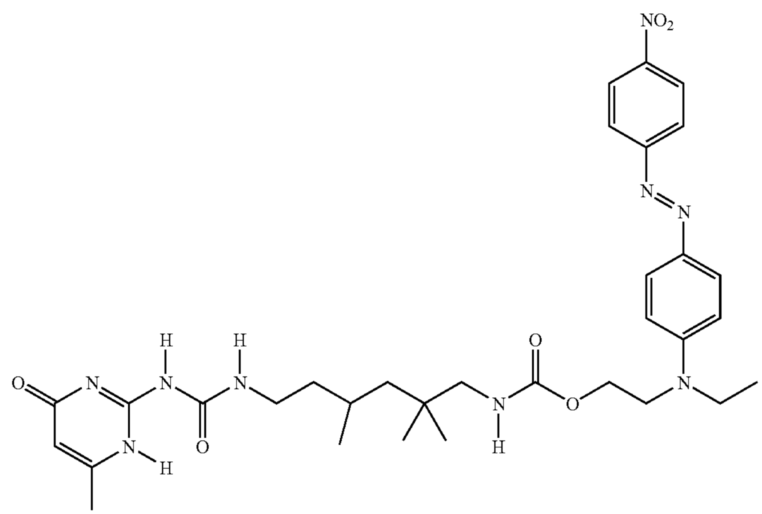

TABLE 1-continued
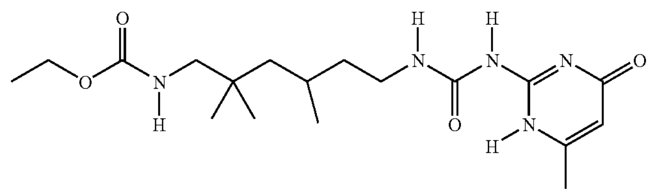
Dye 15
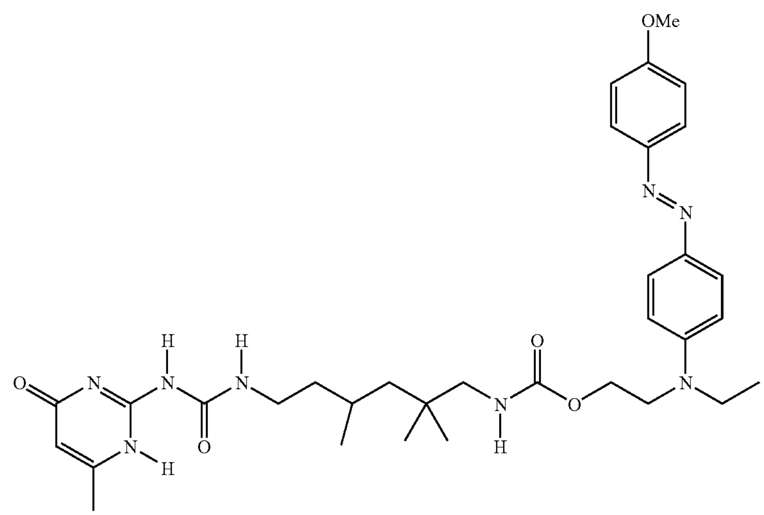
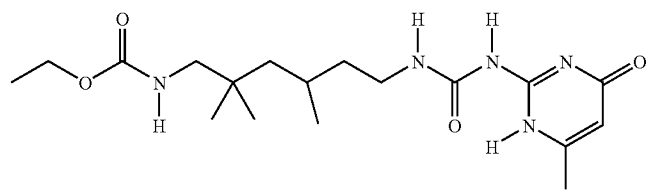
Dye 16
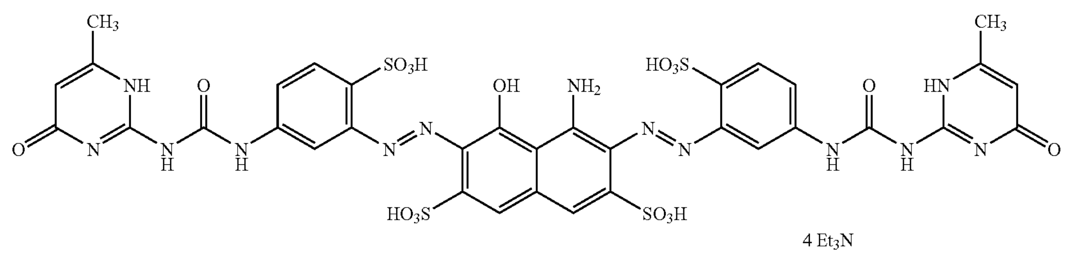
Dye 17

TABLE 1-continued
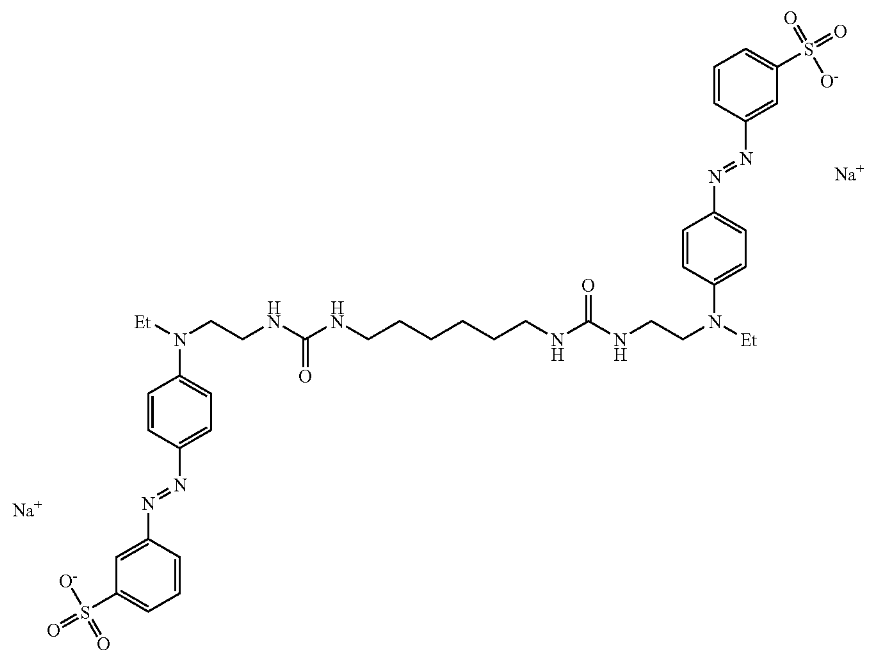
Dye 18
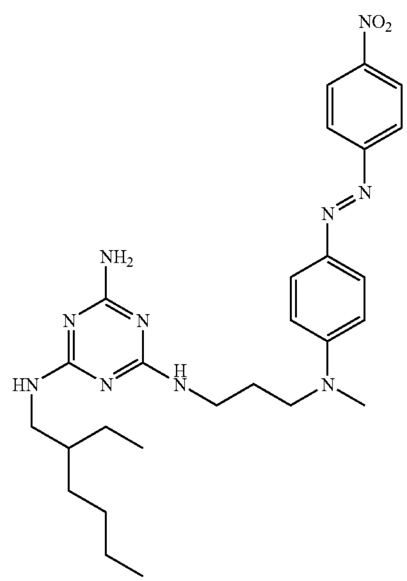
Dye 19

TABLE 1-continued
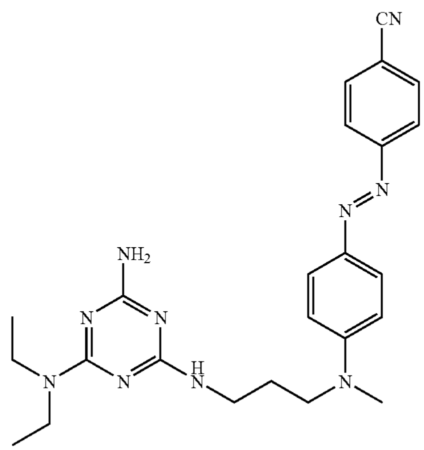
Dye 20
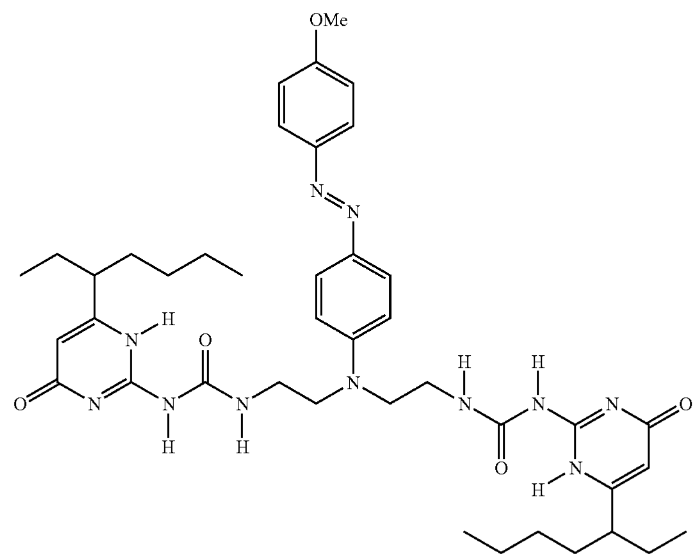
Dye 21
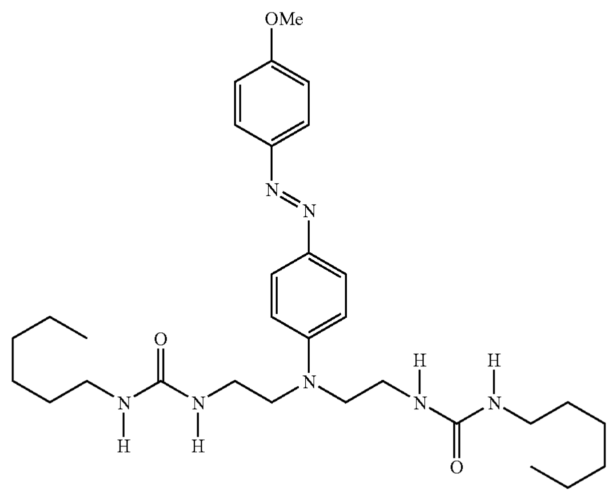
Dye 22

TABLE 1-continued
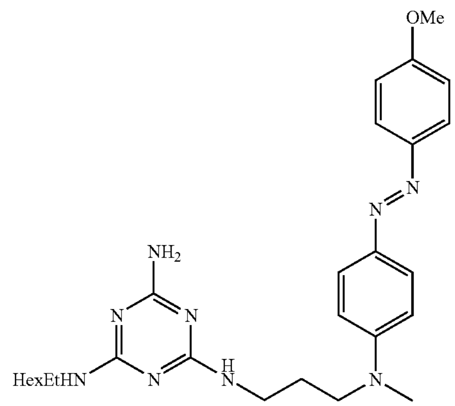
Dye 23
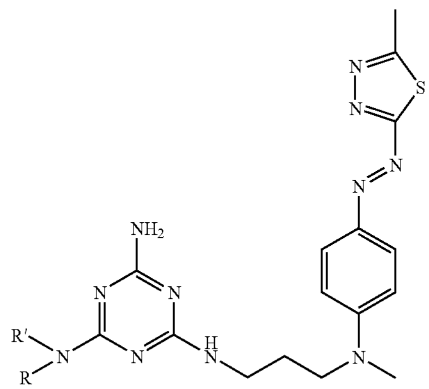
Dye 24 R,R' = isobutyl
Dye 25 R = ethylhexyl, R' = H
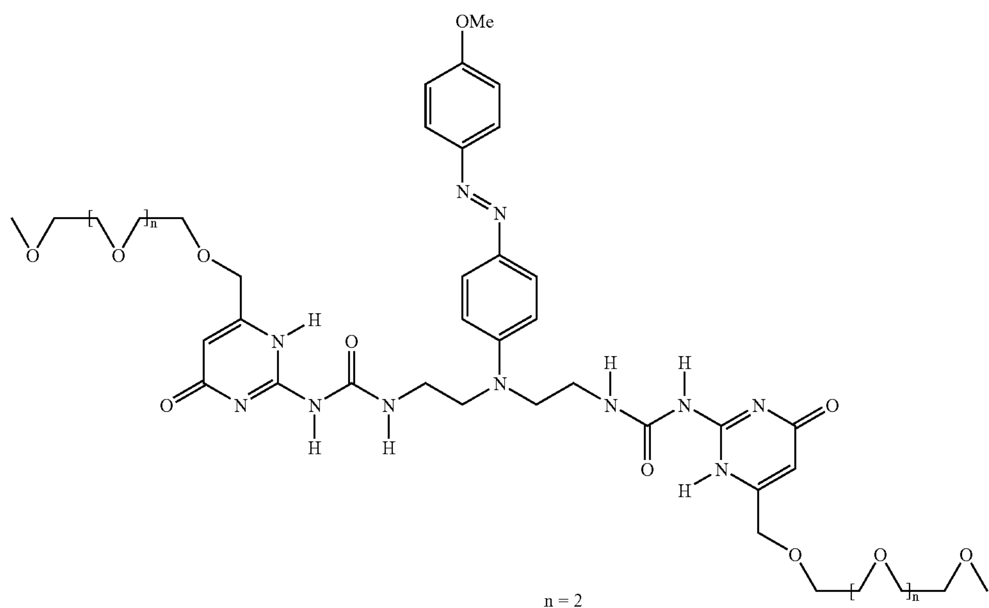
Dye 26

TABLE 1-continued
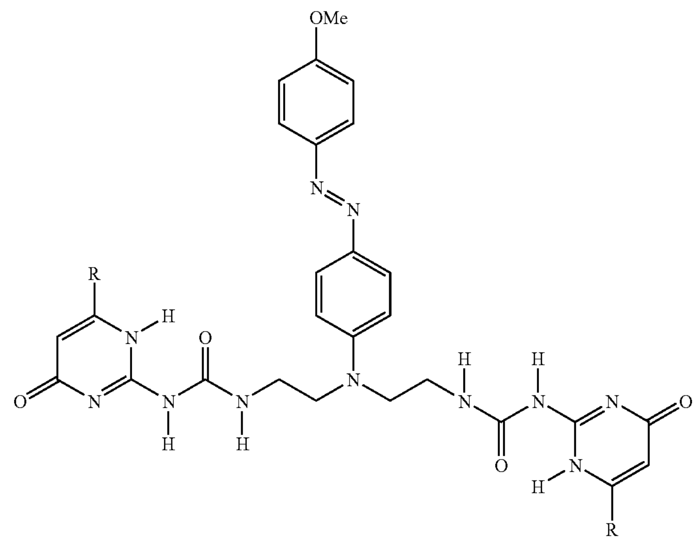
Dye 27
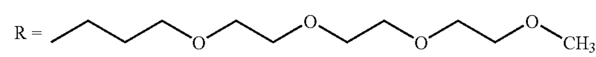
Dye 28
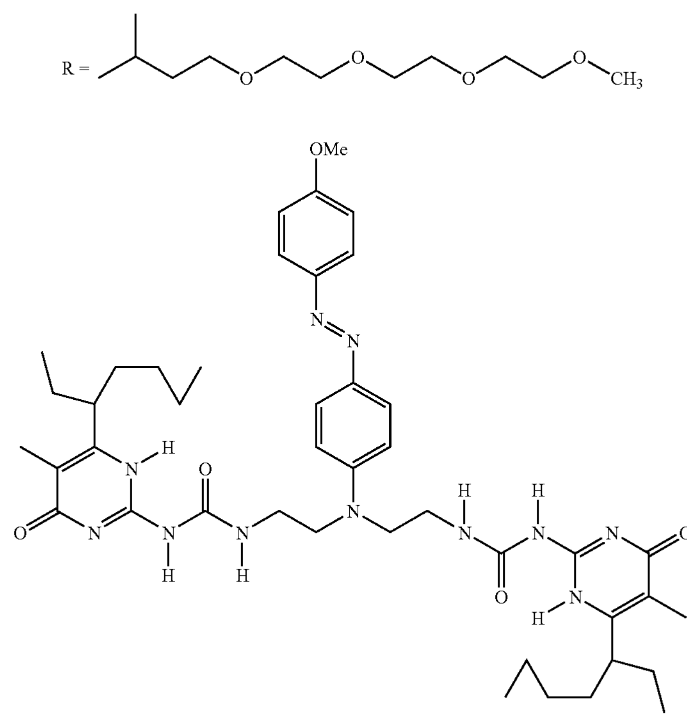
Dye 29

TABLE 1-continued
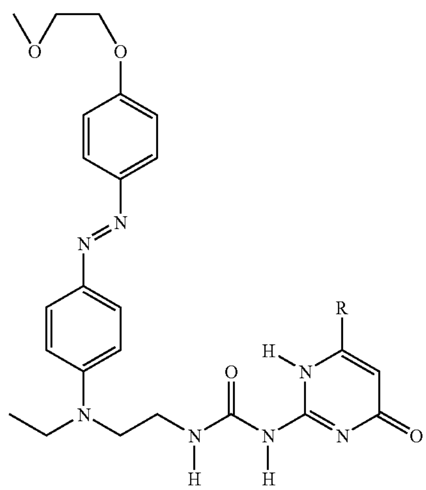
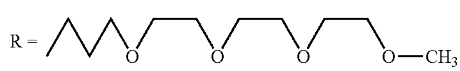
Dye 30
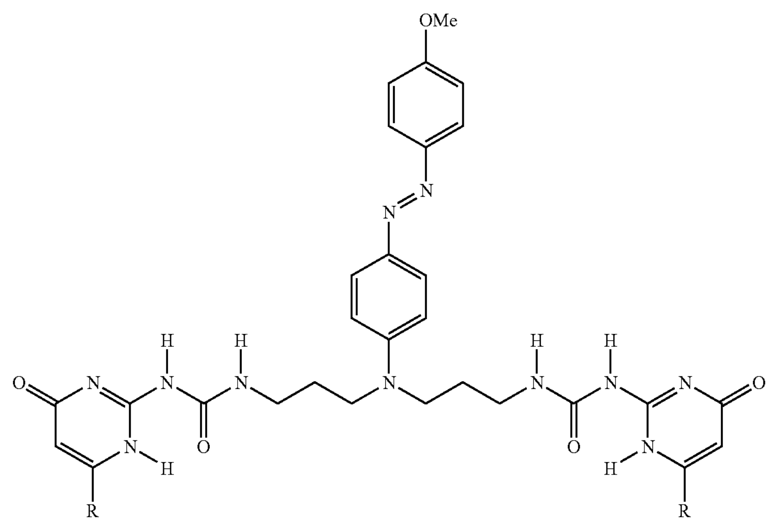
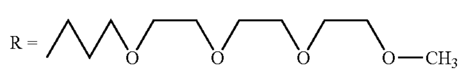
Dye 31

TABLE 1-continued
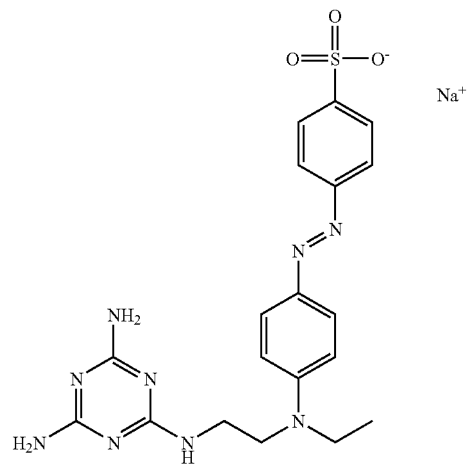
Dye 32
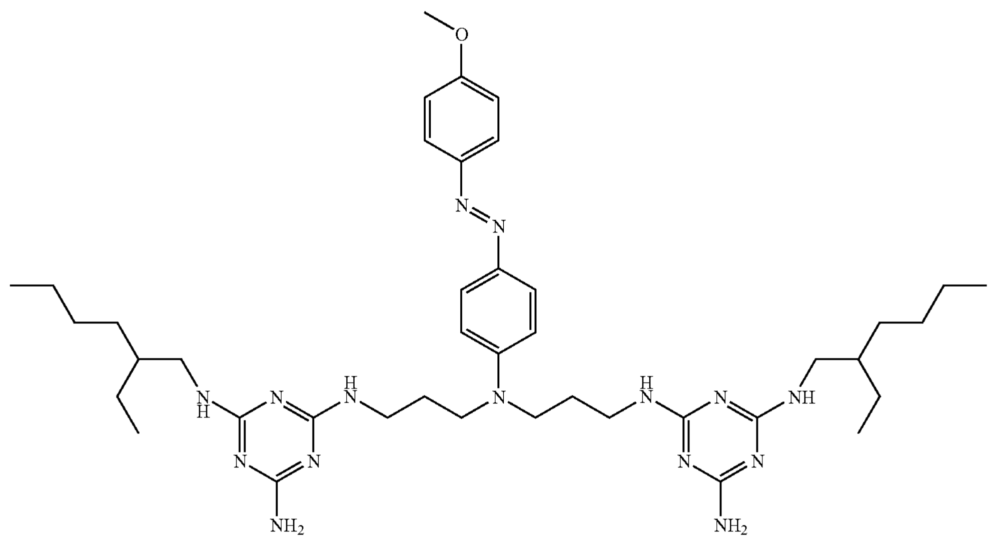
Dye 33
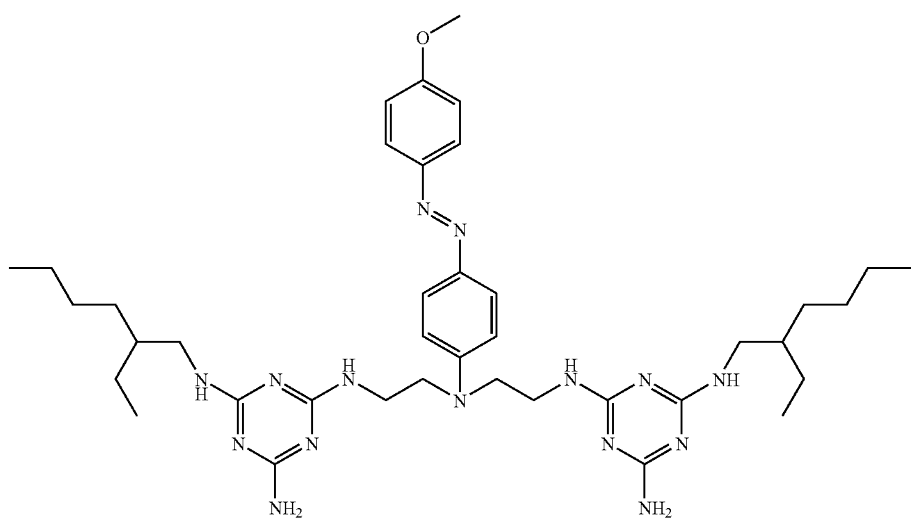
Dye 34

TABLE 1-continued

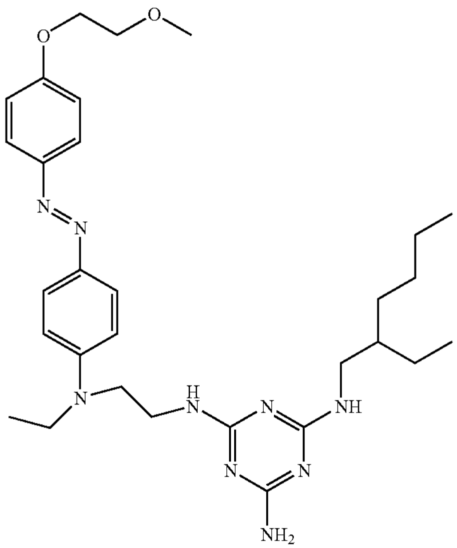

Dye 35

Self-assembling

According to the present invention self-assembling dyes are used to construct supramolecular dye-systems with improved properties such as light-fastness, water and solvent fastness. A distinctive feature of using weak, non-covalent forces in molecular assemblies is that such interactions are normally readily reversible so that the final product is in thermodynamic equilibrium with its components (usually via its corresponding partially assembled intermediates). This leads to an additional property of most supramolecular systems: they have a built-in capacity for error correction not available in fully covalent systems. Supramolecular systems may also form under kinetic rather than thermodynamic control. This situation will tend to be more likely for larger supra-molecular assemblies incorporating many intermolecular contacts, especially when moderately rigid components are involved.

According to the present invention new self-assembling dyes with improved light-fastness properties have been developed whereby the process of molecular recognition and self-assembly through the formation of intermolecular hydrogen bonds is induced through the removal of the ink vehicle. This process is called "Evaporation Induced Self-Assembly (EISA)". EISA has been used to prepare a photosensitive thin-film mesophase containing a photo-acid generator (Science, Vol. 290, 6 Oct. 2000, 107–111) and for rapid prototyping of patterned functional nanostructures (Nature, Vol. 405, 4 May 2000, 56–60). In liquid based inks EISA occurs through evaporation of the liquid. In phase change inks this process occurs through solidification of the ink. As long as the self-assembling dyes are dissolved in the ink no or only partial self-assembly occurs because of the formation of hydrogen bonds with the ink vehicle. Once the ink vehicle (or one of the ink vehicles) is removed through for example evaporation, self-assembly of the dyes is induced resulting in supramolecular structures. In these assemblies the integrity of the individual component molecules normally remains largely intact, that is, the wave functions of the respective molecular components remain largely separate on complex formation. However, after the initial self-assembly process through hydrogen bonding has started, secondary interactions may occur such as π-stacking resulting in more rigid structures with different physical properties such as shifts in spectral absorption and molecular extinction coefficient, extra energy levels for thermal relaxation, etc. Due to multiple intermolecular hydrogen bonding the molecule can absorb UV-radiation transforming it into vibrational energy and/or heat through efficient radiationless deactivation pathways, as described in J. Photochem. Photobiol. A: Chem. 1998, 41, p. 227.

According to the present invention the self-assembly process can occur between the self-assembling dyes themselves but also between (a) self-assembling dye molecule(s) and (a) complementary multiple H-donor/acceptor molecule (s) lacking the dye-fragment, e.g. molecules according to formula II.

Hydrogen bonds are a special type of electrostatic interaction and can be described as an attractive interaction between a proton donor and a proton acceptor. According to the present invention the definition of a hydrogen bond presented by Pimentel and McClellan (G. C. Pimentel, A. L. McClellan, The Hydrogen Bond, Freeman, San Francisco, 1960) is used, which is:

A hydrogen bond exists between a functional group A-H and an atom or a group of atoms B in the same or a different molecule when:

(a) there is evidence of bond formation (association or chelation);

(b) there is evidence that this new bond linking A-H and B specifically involves the hydrogen atom already bonded to A.

Both the donor (A) and the acceptor (B) atoms have electronegative character, with the proton involved in the hydrogen bond being shared between the electron pairs on A and B. The inherent directionality of hydrogen bonds makes them ideal for use in achieving complementarity in supramolecular systems.

Dye System

The self-assembly of dyes of ink compositions according to the present invention results in supramolecular structures, which are called dye systems. Representative examples of different types of dye systems are shown in System Formulas 1 to 10. In some System Formulas the dyes are represented in their assembled form, in other in their singular molecular form.

System Formula 1.

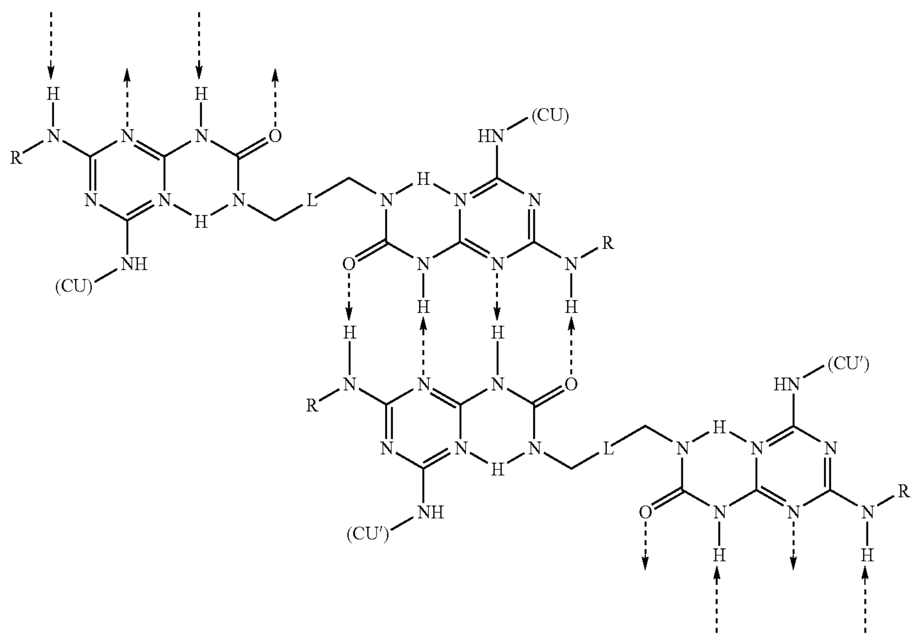

wherein

CU and CU' are the same or different and represent any chromophore group absorbing between 200 nm and 2000 nm, such as an azo dye, an anthraquinone dye, a (poly) methine dye, an azomethine dye, a polyene dye, a pyrene dye, a disazo dye, a carbonium dye, a styryl dye, a stilbene dye, a phthalocyanine dye, a coumarin dye, an arylcarbonium dye, a nitro dye, a naphtholactam dye, a dioxazine dye, a flavin dye and a formazan dye;

R represents hydrogen, a substituted or unsubstituted alkyl group, a substituted or unsubstituted aryl group, a substituted or unsubstituted aralkyl group, a substituted or unsubstituted acyl group, a substituted or unsubstituted sulphonyl group, a substituted or unsubstituted phosphoryl group, a heterocyclic group; and L represents any linking group containing at least one carbon, silicon, nitrogen, phosphorous, sulfur or oxygen atom, but is preferably selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group.

System Formula 2.

2.a

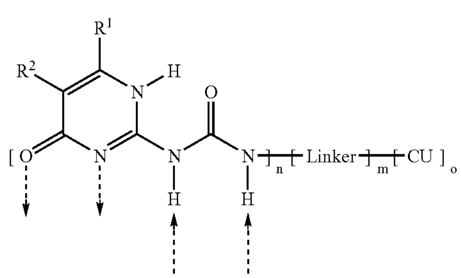

2.b

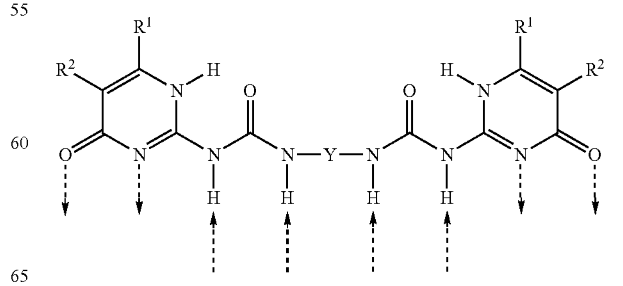

wherein,

Linker represents any linking group containing at least one carbon, silicon, nitrogen, phosphorous, sulfur or oxygen atom, but is preferably selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group.

CU means any chromophore group absorbing between 200 nm and 2000 nm, such as an azo dye, an anthraquinone dye, a (poly)methine dye, an azomethine dye, a polyene dye, a pyrene dye, a disazo dye, a carbonium dye, a styryl dye, a stilbene dye, a phthalocyanine dye, a coumarin dye, an aryl-carbonium dye, a nitro dye, a naphtholactam dye, a dioxazine dye, a flavin dye and a formazan dye;

n and o are the same or different and are integers having a value of at least 1; m can be zero or any integer having a value of at least 1;

$R^1$ and $R^2$ are the same or different and represent hydrogen, a halogen, a substituted or unsubstituted alkoxy group, a substituted or unsubstituted thioalkoxy group, a substituted or unsubstituted sulphoxy group, a substituted or unsubstituted sulphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group, a heterocyclic group, a CU group, or $R^1$ and $R^2$ represent the necessary atoms to form a ring system;

Y represents CU or Z-CU; and

Z represents any linking group containing at least one carbon, silicon, nitrogen, phosphorous, sulfur or oxygen atom, but is preferably selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group.

Preferably n and o are integers independently selected from the range 1 to 100, more preferably integers selected from the range 1 to 10, and particularly preferably integers selected from the range 1 to 5. Preferably m is an integer selected from the range 1 to 10, and particularly preferably selected from the range 1 to 5.

System Formula 3.

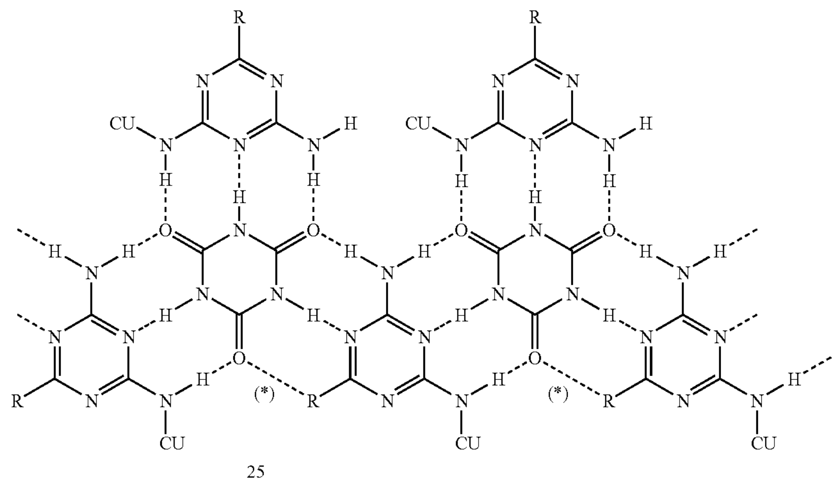

R represents hydrogen, a substituted or unsubstituted alkyl group, a substituted or unsubstituted aryl group, a substituted or unsubstituted aralkyl group, a heterocyclic group, a chromophore group CU or CU', —$OR^1$, or —$NR^2R^3$;

$R^1$ represents hydrogen, a substituted or unsubstituted alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group, a heterocyclic group or a chromophore group CU or CU';

$R^2$ and $R^3$ are the same or different and represent hydrogen ((*) when $R^2$ and/or $R^3$ represent hydrogen then an extra hydrogen bond is formed in System Formula 3), a substituted or unsubstituted alkyl group, a substituted or unsubstituted aryl group, a substituted or unsubstituted aralkyl group, a heterocyclic group, a substituted or unsubstituted acyl group, a substituted or unsubstituted sulphonyl group, a substituted or unsubstituted phosphoryl group, a chromophore group, or $R^2$ and $R^3$ represent the necessary atoms to form a ring system; and CU and CU' are the same or different and represent any chromophore group absorbing between 200 nm and 2000 nm, such as an azo dye, an anthraquinone dye, a (poly) methine dye, an azomethine dye, a polyene dye, a pyrene dye, a disazo dye, a carbonium dye, a styryl dye, a stilbene dye, a phthalocyanine dye, a coumarin dye, an aryl-carbonium dye, a nitro dye, a naphtholactam dye, a dioxazine dye, a flavin dye and a formazan dye.

System Formula 4.

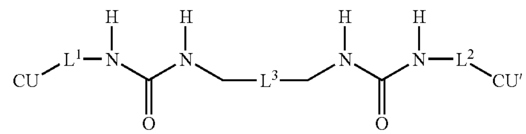

CU and CU' are the same or different and represent any chromophore group absorbing between 200 nm and 2000 nm, such as an azo dye, an anthraquinone dye, a (poly) methine dye, an azomethine dye, a polyene dye, a pyrene dye, a disazo dye, a carbonium dye, a styryl dye, a stilbene dye, a phthalocyanine dye, a coumarin dye, an arylcarbonium dye, a nitro dye, a naphtholactam dye, a dioxazine dye, a flavin dye and a formazan dye; and $L^1$, $L^2$ and $L^3$ are the same or different and represent any linking group containing at least one carbon, silicon, nitrogen, phosphorous, sulfur or oxygen atom, but is preferably selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group $R^2$ and $R^3$ are the same or different and represent hydrogen, a substituted or unsubstituted alkyl group, a substituted or unsubstituted aryl group, a substituted or unsubstituted aralkyl group, a heterocyclic group or $R^2$ and $R^3$ represent the necessary atoms to form a ring system; and CU and CU' are the same or different and represent any chromophore group absorbing between 200 nm and 2000 nm, such as an azo dye, an anthraquinone dye, a (poly) methine dye, an azomethine dye, a polyene dye, a pyrene dye, a disazo dye, a carbonium dye, a styryl dye, a stilbene dye, a phthalocyanine dye, a coumarin dye, an arylcarbonium dye, a nitro dye, a naphtholactam dye, a dioxazine dye, a flavin dye and a formazan dye.

System Formula 5.

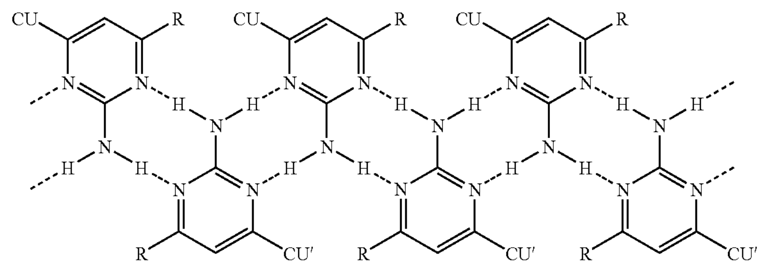

R represents hydrogen, a substituted or unsubstituted alkyl group, a substituted or unsubstituted aryl group, a substituted or unsubstituted aralkyl group, a heterocyclic group, CU or CU', —$OR^1$, —$NR^2R^3$;

System Formula 6.

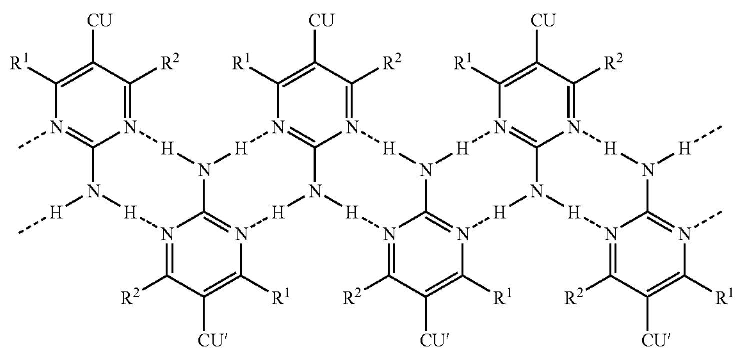

$R^1$ represents hydrogen, a substituted or unsubstituted alkyl group, a substituted or unsubstituted aryl group, a substituted or unsubstituted aralkyl group or a heterocyclic group;

$R^1$ and $R^2$ are the same or different and represent hydrogen, a substituted or unsubstituted alkyl group, a substituted or unsubstituted aryl group, a substituted or unsubstituted aralkyl group, a heterocyclic group, —$OR^3$, —$NR^4R^5$;

$R^3$ represents hydrogen, a substituted or unsubstituted alkyl group, a substituted or unsubstituted aryl group, a substituted or unsubstituted aralkyl group or a heterocyclic group;

$R^4$ and $R^5$ are the same or different and represent hydrogen, a substituted or unsubstituted alkyl group, a substituted or unsubstituted aryl group, a substituted or unsubstituted aralkyl group, a heterocyclic group or $R^4$ and $R^5$ represent the necessary atoms to form a ring system; and CU and CU' are the same or different and represent any chromophore group absorbing between 200 nm and 2000 nm, such as an azo dye, an anthraquinone dye, a (poly) methine dye, an azomethine dye, a polyene dye, a pyrene dye, a disazo dye, a carbonium dye, a styryl dye, a stilbene dye, a phthalocyanine dye, a coumarin dye, an arylcarbonium dye, a nitro dye, a naphtholactam dye, a dioxazine dye, a flavin dye and a formazan dye.

System Formula 7.

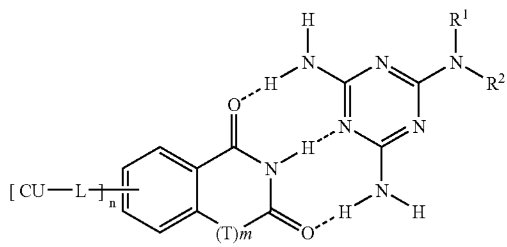

L represents any linking group containing at least one carbon, silicon, nitrogen, phosphorous, sulfur or oxygen atom, but is preferably selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group;

n is an integer having a value of at least 1;

m has a value of 0 or 1, if m=1 then T represents O, $NR^3$, $(CH_2)_p$ whereby p has a value of 0,1 or 2;

$R^1$ and $R^2$ are the same or different and represent hydrogen, a substituted or unsubstituted alkyl group, a substituted or unsubstituted aryl group, a substituted or unsubstituted aralkyl group, a substituted or unsubstituted acyl group, a substituted or unsubstituted sulphonyl group, a substituted or unsubstituted phosphoryl group, a heterocyclic group or $R^1$ and $R^2$ represent the necessary atoms to form a ring system; when $R^1{=}R^2{=}H$, trimers are formed;

$R^3$ represents hydrogen, a substituted or unsubstituted alkyl group, a substituted or unsubstituted aryl group, a substituted or unsubstituted aralkyl group; and CU represents any chromophore group absorbing between 200 nm and 2000 nm, such as an azo dye, an anthraquinone dye, a (poly)methine dye, an azomethine dye, a polyene dye, a pyrene dye, a disazo dye, a carbonium dye, a styryl dye, a stilbene dye, a phthalocyanine dye, a coumarin dye, an aryl-carbonium dye, a nitro dye, a naphtholactam dye, a dioxazine dye, a flavin dye and a formazan dye.

System Formula 8.

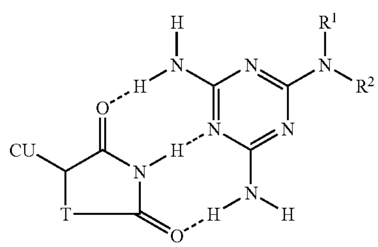

T represents O, $NR^3$, $(CH_2)_n$ whereby n is an integer having a value of at least 1, $R^1$ and $R^2$ are the same or different and represent hydrogen, a substituted or unsubstituted alkyl group, a substituted or unsubstituted aryl group, a substituted or unsubstituted aralkyl group, a substituted or unsubstituted acyl group, a substituted or unsubstituted sulphonyl group, a substituted or unsubstituted phosphoryl group, a heterocyclic group or $R^1$ and $R^2$ represent the necessary atoms to form a ring system; when $R^1{=}R^2{=}H$, trimers are formed;

$R^3$ represents hydrogen, a substituted or unsubstituted alkyl group, a substituted or unsubstituted aryl group, a substituted or unsubstituted aralkyl group; and CU represents any chromophore group absorbing between 200 nm and 2000 nm, such as an azo dye, an anthraquinone dye, a (poly)methine dye, an azomethine dye, a polyene dye, a pyrene dye, a disazo dye, a carbonium dye, a styryl dye, a stilbene dye, a phthalocyanine dye, a coumarin dye, an aryl-carbonium dye, a nitro dye, a naphtholactam dye, a dioxazine dye, a flavin dye and a formazan dye.

System Formula 9.

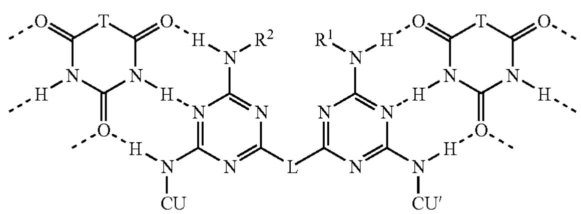

CU and CU' are the same or different and represent any chromophore group absorbing between 200 nm and 2000 nm, such as an azo dye, an anthraquinone dye, a (poly) methine dye, an azomethine dye, a polyene dye, a pyrene dye, a disazo dye, a carbonium dye, a styryl dye, a stilbene dye, a phthalocyanine dye, a coumarin dye, an arylcarbonium dye, a nitro dye, a naphtholactam dye, a dioxazine dye, a flavin dye and a formazan dye;

$R^1$ and $R^2$ are the same or different and represent hydrogen, a substituted or unsubstituted alkyl group, a substituted or unsubstituted aryl group, a substituted or unsubstituted aralkyl group, a substituted or unsubstituted acyl group, a substituted or unsubstituted sulphonyl group, a substituted or unsubstituted phosphoryl group, a substituted or unsubstituted cycloalkyl group, a heterocyclic group;

T represents $NR^3$ or $CR^4R^5$; $R^3$ represents hydrogen, a substituted or unsubstituted alkyl group, a substituted or unsubstituted aryl group, a substituted or unsubstituted aralkyl group, a substituted or unsubstituted cycloalkyl group or a heterocyclic group; $R^4$ and $R^5$ are the same or different and represent hydrogen, a substituted or unsubstituted alkyl group, a substituted or unsubstituted aryl group, a substituted or unsubstituted aralkyl group, a heterocyclic group or $R^4$ and $R^5$ represent the necessary atoms to form a ring system; and L represents any linking group containing at least one carbon, silicon, nitrogen, phosphor, sulfur or oxygen atom, but is preferably selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group.

heterocyclic group or $R^4$ and $R^5$ represent the necessary atoms to form a ring system.

Ink-jet Ink

In a first embodiment of this invention, inks are formulated containing self-assembling dyes according to formula (I). Examples of different dye systems are shown in System Formulas 1, 2, 4, 5 and 6. Self-assembly through the formation of intermolecular hydrogen bonds, may be induced through evaporation of the ink vehicle. As long as the self-assembling dyes are dissolved in the ink no or partial self-assembly occurs because of the formation of hydrogen bonds with the ink vehicle. Once the ink vehicle (or one of the ink vehicles) is removed through, for example, evaporation, self-assembly of the dyes is induced resulting in supramolecular structures. In these assemblies the integrity of the individual component molecules normally remains largely intact: that is, the wave functions of the respective molecular components remain largely separate on complex formation. However, after the initial self-assembly process through hydrogen bonding has started, secondary interactions may occur such as π-stacking resulting in more rigid structures with different physical properties such as shifts in spectral absorption and molecular extinction coefficient, extra energy levels for thermal relaxation, etc.

System Formula 10.

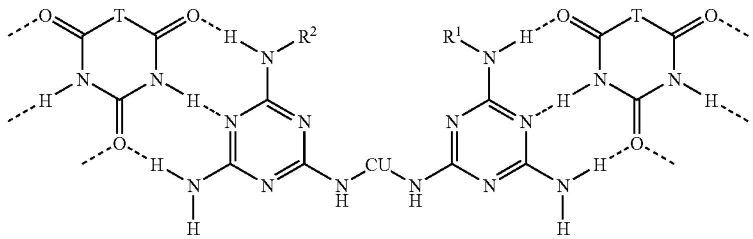

CU represents any chromophore group absorbing between 200 nm and 2000 nm, such as an azo dye, an anthraquinone dye, a (poly)methine dye, an azomethine dye, a polyene dye, a pyrene dye, a disazo dye, a carbonium dye, a styryl dye, a stilbene dye, a phthalocyanine dye, a coumarin dye, an aryl-carbonium dye, a nitro dye, a naphtholactam dye, a dioxazine dye, a flavin dye and a formazan dye;

$R^1$ and $R^2$ are the same or different and represent hydrogen, a substituted or unsubstituted alkyl group, a substituted or unsubstituted aryl group, a substituted or unsubstituted aralkyl group, a substituted or unsubstituted acyl group, a substituted or unsubstituted sulphonyl group, a substituted or unsubstituted phosphoryl group, a substituted or unsubstituted cycloalkyl group, a heterocyclic group; and T represents $NR^3$ or $CR^4R^5$; $R^3$ represents hydrogen, a substituted or unsubstituted alkyl group, a substituted or unsubstituted aryl group, a substituted or unsubstituted aralkyl group, a substituted or unsubstituted cycloalkyl group, a heterocyclic group; $R^4$ and $R^5$ are the same or different and represent hydrogen, a substituted or unsubstituted alkyl group, a substituted or unsubstituted aryl group, a substituted or unsubstituted aralkyl group, a In a second embodiment of this invention inks are formulated which contain at least two dyes $(CU)_n(SAU)_m$ according to formula (I), whereby the SAU group of one dye is complementary with the SAU group of the other dye so that the dyes are able to self-assemble with one another.

Assembly through the formation of intermolecular hydrogen bonds is induced through evaporation of the ink vehicle. As long as the self-assembling dyes are dissolved in the ink no or partial self-assembly occurs because of the formation of hydrogen bonds with the ink vehicle. Once the ink vehicle (or one of the ink vehicles) is removed through, for example, evaporation, self-assembly of the dyes is induced resulting in supramolecular structures. The considerations about the integrity of the individual component molecules are the same as for the first embodiment.

In a third embodiment of this invention inks are formulated containing a dye according to formula (I) and at least one compound according to formula (II), whereby the SAU and SAU' are complementary so that the dye of formula (I) and the compound(s) of formula (II) is(are) able to self-assemble with each other. Assembly through the formation of intermolecular hydrogen bonds may be induced through evaporation of the ink vehicle. As long as the assembling dyes are dissolved in the ink no or partial assembly occurs because of the formation of hydrogen bonds with the ink vehicle. Once the ink vehicle (or one of the ink vehicles) is removed through, for example, evaporation, assembly of the dyes is induced resulting in supramolecular structures. The considerations about the integrity of the individual component molecules are the same as for the first and second embodiment.

In a fourth embodiment of this invention the components of the self-assembly process are separated from each other. The dye according to formula (I) is part of the ink while a second dye according to formula (I) or the compound(s) according to formula (II) are incorporated into an ink receiving layer of an ink-jet recording element.

So, apart from a process wherein ink compositions as defined above are used, the scope of the present invention further encompasses a process for the formation of an ink-jet image comprising the step of image-wise jetting by means of an ink-jet printing apparatus onto an ink-jet recording element, comprising a support and at least one ink receiving layer, droplets of an ink composition comprising a liquid or solid vehicle and at least one first dye according to the formula (I):

$$(CU)_n(SAU)_m \quad (I)$$

wherein,

CU means any chromophore group with an absorption maximum between 200 nm and 2000 nm covalently linked to SAU, SAU means a multiple H-donor/accepting group, which can form at least three hydrogen bonds;

and wherein said ink receiving layer comprises at least a second dye according to formula (I), so that after the image-wise jetting of the ink droplets said first dye according to formula (I) and said second dye according to formula (I) self-assemble in the ink receiving layer, whereby the association constant of the assembly reaction $K_{ass}$, determined by $^1$H-NMR in $CDCl_3$, is at least 2.5 $M^{-1}$;

n and m are at least 1; when n is greater than 1 the CU groups may be the same or different; when m is greater than 1 the SAU groups may be the same or different.

The scope of the present invention further encompasses a process for the formation of an ink-jet image comprising the step of image-wise jetting by means of an ink-jet printing apparatus onto an ink-jet recording element, comprising a support and at least one ink receiving layer, droplets of an ink composition comprising a liquid or solid vehicle and at least one dye according to the formula (I):

$$(CU)_n(SAU)_m \quad (I)$$

wherein,

CU means any chromophore group with an absorption maximum between 200 nm and 2000 nm covalently linked to SAU, SAU means a multiple H-donor/accepting group, which can form at least three hydrogen bonds;

and wherein said ink receiving layer comprises at least one compound according to formula (II):

$$(SAU')_p(X)_q \quad (III),$$

so that after the image-wise jetting of the ink droplets said at least one dye $(CU)_n(SAU)_m$ and said at least one compound $(SAU')_p(X)_q$ self-assemble in the ink receiving layer;

n, m, and p are at least 1; when n is greater than 1 the CU groups may be the same or different; when m or p is greater than 1 the SAU or SAU' groups may be the same or different;

X is any linking group and q is 0 or 1.

The second dye according to formula (I) or the compounds according to formula (II) can be present in the ink receiving layer of the ink-jet recording element as single molecules or covalently linked to a polymer backbone such as gelatin, cellulose, polyvinyl alcohol, etc. Preferably the second dye according to formula (I) or the compounds according to formula (II) are present in the ink-receiving layer as single molecules. The considerations about the mechanism of the assembly and about the integrity of the component molecules are the same as for the previous embodiments.

Ink Vehicle

The ink compositions according to the present invention can be formulated as water based inks, solvent and/or oil based inks, as UV-curable inks and as hot melt (phase change) inks. Suitable ink compositions are described extensively in the existing patent literature and can be found for example in “Ink-jet Technology and Product Development Strategies, Stephen F. Pond, Torrey Pines Research, 2000, Chapter 5: Ink Design” and references cited therein.

Preferred ink compositions are those comprising dyes according to the present invention in an aqueous vehicle and in a solvent and/or oil based vehicle.

The present dyes are useful as colorants for aqueous inks. The ink-compositions of the present invention preferably contain from 0.5% to 40%, more preferably from 0.5% to 15%, and especially from 1% to 10%, by weight of the dye of formula (I) based on the total weight of the ink. Although many ink compositions contain less than 5% by weight of colorant, it is desirable that the dye has a solubility of around 10 wt % or more. This allows the preparation of concentrated inks, which may be used to prepare more dilute inks and to minimize the chance of precipitation of colorant if evaporation of the liquid vehicle occurs during use of the ink.

When the liquid vehicle is an aqueous vehicle it is preferably water or a mixture of water and one or more water-soluble organic solvents. The weight ratio of water to organic solvent(s) is preferably from 99:1 to 1:99, more preferably from 99:1 to 50:50 and especially from 95:5 to 80:20. The water-soluble organic solvents) is(are) preferably selected from $C_{1-4}$-alkanols such as methanol, ethanol, n-propanol, isopropanol, n-butanol, sec-butanol, tert-butanol; amides such as dimethylformamide or dimethylacetamide; ketones or ketone-alcohols such as acetone or diacetone alcohol; ethers such as tetrahydrofuran or dioxane; oligo- or poly-alkyleneglycols such as diethylene glycol, triethylene glycol, hexylene glycol, polyethylene glycol or polypropylene glycol; alkyleneglycols or thioglycols containing a $C_2$–$C_6$ alkylene group such as ethylene glycol, propylene glycol, butylene glycol, pentylene glycol or hexylene glycol and thiodiglycol; polyols such as glycerol or 1,2,6-hexanetriol; $C_{1-4}$-alkyl-ethers of polyhydric alcohols such as 2-methoxyethanol, 2-(2-methoxyethoxy)ethanol, 2-(2-ethoxyethoxy)ethanol, 2-[2-(2-methoxyethoxy)ethoxy] ethanol, 2-[2-(2-ethoxyethoxy)-ethoxy]-ethanol, ethyleneglycolmonoallylether; heterocyclic amides, such as 2-pyrrolidone, N-methyl-2-pyrrolidone, N-ethyl-2-pyrrolidone and 1,3-dimethylimidazolidone; sulphoxides such as dimethyl sulphoxide and sulpholane or mixtures containing two or more of the aforementioned water-soluble organic solvents, for example thiodiglycol and a second glycol or diethylene glycol and 2-pyrrolidone. Preferred water-soluble organic solvents are 2-pyrrolidone; N-methyl-pyrrolidone; alkylene- and oligo-alkyleneglycols, such as ethyleneglycol, diethyleneglycol, triethyleneglycol; and lower alkyl ethers of polyhydric alcohols such as or 2-methoxy-2-ethoxy-2-ethoxy-ethanol; and polyethyleneglycols with a molecular weight of up to 500.

The present dyes are particularly useful as colorants for solvent and/or oil based inks. Solvent based ink compositions are used where fast drying times are required and particularly when printing onto hydrophobic substrates such as plastics, metal or glass. Where the liquid vehicle is solvent based the solvent is preferably selected from ketones, alkanols, aliphatic hydrocarbons, esters, ethers, amides or mixtures thereof. Where an aliphatic hydrocarbon is used as the solvent a polar solvent such as an alcohol, ester, ether or amide is preferably added. Preferred solvents include ketones, especially methyl ethyl ketone and alkanols especially ethanol and n-propanol.

Typical solvents for solvent based ink-jet inks are methanol, ethanol, propanol, diacetone alcohol, methoxypropanol, glycol, methyl ethyl ketone, methyl isopropyl ketone, ethyl acetate, butyl acetate and methoxypropyl acetate, ethyl lactate and butyl lactate, monomethylethers from glycol, n.butylether from diethyleneglycol (Dowanol PM-series) and triethyleneglycol, tripropyleneglycolmonomethylether (TMP), dipropyleneglycolmonomethylether, and (di)methylnaphthalene. The less volatile solvents are more often used in oil based inks.

Solvent and/or oil based ink compositions of the present invention preferably contain from 0.5% to 40%, more preferably from 0.5% to 15%, and especially from 1% to 10%, by weight of the dye of formula (1) based on the total weight of the ink. Although many ink compositions contain less than 5% by weight of colorant, it is desirable that the dye has a solubility of around 10% or more. This allows the preparation of concentrated inks, which may be used to prepare more dilute inks and to minimize the chance of precipitation of colorant if evaporation of the liquid vehicle occurs during use of the ink.

When the vehicle for an ink composition is a low melting point solid, the melting point of the solid is preferably in the range from 60° C. to 125° C. Suitable low melting point solids include long chain fatty acids or alcohols, preferably those with $C_{18}$ to $C_{24}$ chains, or sulphonamides. The dyes according to the present invention or mixtures of the dyes may be dissolved in the low melting point solid or may be finely dispersed in it.

For ink-jet applications the viscosity of the final ink should be between 1–25 mPa·s at 20° C., preferably between 1–15 mPa·s at 20° C. and most preferably between 1–10 mPa·s at 20° C. for water and solvent-based inks, and between 1–25 mPa·s at 45° C., preferably between 2–18 mPa·s at 45° C. and most preferably between 3–12 mPa·s at 45° C. for oil-based inks.

Other Ingredients

The ink compositions according to the present invention may contain further colorants other than the dyes according the present invention, for example to modify the color or brightness of the ink. Colorants may be dyes, pigments or a combination thereof. Both organic and/or inorganic pigments may be used.

The ink compositions according to the present invention may further include a surfactant. The surfactant can be anionic, cationic, non-ionic, or zwitter-ionic and added in a total amount below 20.0 wt % based on the total ink weight.

A biocide may be added to the ink composition according to the present invention to prevent unwanted microbial growth, which may occur in the ink composition over time. The biocide may be used either singly or in combination. Each of them is preferably added in an amount of 0.001 to 3 wt % based on the total weight of the ink composition.

They may also contain stabilizing agents, such as UV-absorbers, singlet oxygen quenchers such as hindered amine light stabilizers, peroxide scavengers and other radical scavengers.

The ink composition according to the present invention may contain a humectant to prevent the clogging of the nozzle, due to its ability to slow down the evaporation rate of ink. Suitable humectants include, for example, triacetin, N-methyl-2-pyrrolidone, glycerol, urea, thiourea, ethylene urea, alkyl urea, alkylthiourea, dialkyl urea and dialkyl thiourea, diols, including ethanediols, propanediols, propanetriols, butanediols, pentanediols, and hexanediols; glycols, including propylene glycol, polypropylene glycol, ethylene glycol, polyethylene glycol, diethylene glycol, tetraethylene glycol, and mixtures and derivatives thereof. A preferred humectant is polyethylene glycol and added to the ink-jet ink formulation in an amount of 0.1 to 20 wt % of the ink composition.

The ink composition according to the present invention may further contain a thickener used for viscosity regulation, pH controlling agents, evaporation accelerators, rust inhibitors, crosslinking agents, soluble electrolytes as conductivity aid, sequestering agents and chelating agents.

Ink-jet Recording Element

The ink-jet recording element used with the ink compositions according to the present invention comprises a support and optionally at least one ink-receiving layer.

The support of the ink-jet recording element can be chosen from the paper type, metal type and polymeric type support. Paper types include plain paper, cast coated paper, polyethylene coated paper and polypropylene coated paper. Polymeric supports include cellulose acetate propionate or cellulose acetate butyrate, polyesters such as polyethylene terephthalate (PET) and polyethylene naphthalate, polyamides, polycarbonates, polyimides, polyolefins, poly(vinylacetals), polyethers and polysulphonamides. Other examples of useful high-quality polymeric supports for the present invention include opaque white polyesters and extrusion blends of polyethylene terephthalate and polypropylene. Polyester film supports, and especially polyethylene terephthalate, are preferred because of their excellent properties of dimensional stability. When the ink-jet recording material is meant for outdoor use then typical useful supports include PET, wet strength paper, PVC, PVC with an adhesive backing, the polyethylene paper TYVEK, trade name of Du Pont Co., the porous polyethylene paper TESLIN, trade name of International Paper CO., canvas, polypropylene, and polycarbonate. Metal type supports include aluminum and steel plates.

The ink-receiving layer may contain the typical ingredients well known in the art from numerous patent applications. Typical ingredients include binders, pigments, mordants, surfactants, spacing agents, whitening agents, UV-absorbers, hardeners, plasticizers, etc.

Ink-jet Printing Apparatus

The scope of the present invention further encompasses an ink-jet printing apparatus comprising an ink cartridge containing an ink composition according to the presents invention with a dye according to formula (I), and optionally at least one compound according to formula (II) or (III) as extensively described above. The ink-jet printing process can be performed according to any of the well-known techniques, such as the continuous printing method, the thermal jet method and the piezo method.

The present invention will now be illustrated by the following examples without however being limited thereto.

EXAMPLES

The Synthesis Examples 1 to 31 deal with the synthesis of the dyes used in accordance with the present invention, or of intermediates thereof. The evaluation of the dyes according to the present invention is described in the section 'Ink-jet Examples'.

Materials

All materials used in the examples were readily available from standard commercial sources such as ALDRICH CHEMICAL Co. (Belgium) unless otherwise specified.

Reference dyes are commercially available from commercial sources such as ALDRICH CHEMICAL Co. (Belgium), CLARIANT or MERCK are prepared according to published methods, unless described in the Examples.

Measurement Methods

UV data have been recorded in 1 cm sample holders with observed optical densities between 0.1 and 2.0. $\epsilon$ is given as $1.mol^{-1}.cm^{-1}$. Different Perkin Elmer UV-spectroscopes have been used. FT-IR spectra have been recorded on a Spectrum One Perkin Elmer ATR FT-IR spectroscope. NMR spectra have been recorded on a 300 MHz Varian spectroscope. MALDI-TOF MS data have been recorded on a Perceptive Voyager DE Pro spectrometer.

The density, i.e. optical density of the Ink-jet Examples was measured using a MacBeth TR1224 densitometer.

SYNTHESIS EXAMPLES

The Synthesis Examples 1 to 31 deal with the synthesis of the dyes used in accordance with the present invention, or of intermediates thereof.

Synthesis Example 1

This example discloses the synthesis of the Isocyanate-1.

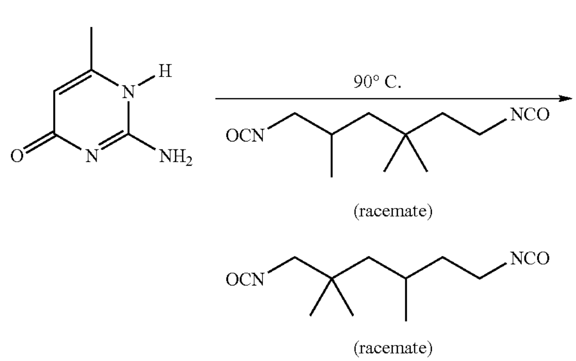

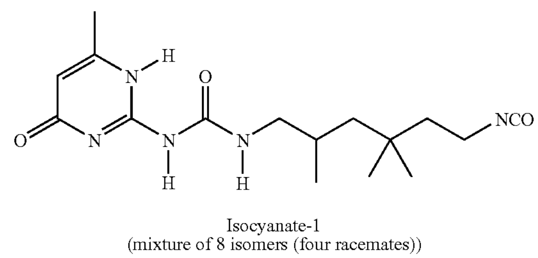

Isocyanate-1
(mixture of 8 isomers (four racemates))

3 mL of pyridine were added to a white suspension of the isocytosine (2 gram) and a mixture of 2,2,4-trimethyl-1,6-diisocyanate and 2,4,4-trimethyl-1,6-diisocyanate (24 gram). The mixture was heated for 21 hours at an oil bath temperature of 100° C. under a slight argon flow. The reaction mixture was cooled to room temperature and pentane was added to induce precipitation of a white product. The suspension was filtered and the residue was washed several times with pentane to yield the isocyanate-1 as a white solid. Yield: 60%.

1H NMR (300 MHz, $CDCl_3$): δ=0.95–1.05 (m, 9H), 1.1 (m, 1H), 1.3 (m, 1H), 1.6 (m, 2H), 1.8 (m, 1H), 2.2 (s, 3H), 3,0–3.4 (m, 4H), 5.8 (s, 1H), 10.1 (s, 1H), 11.7 (s, 1H), 13.1 (s, 1H). IR: ν (cm−1)=709, 744, 761, 798, 844, 946, 971, 1028, 1132, 1171, 1248, 1319, 1368, 1381, 1390, 1415, 1439, 1469, 1518, 1580, 1647, 1693, 2260, 2873, 2933, 2956, 3143, 3196.

Synthesis Example 2

This example discloses the synthesis of Dye-1.

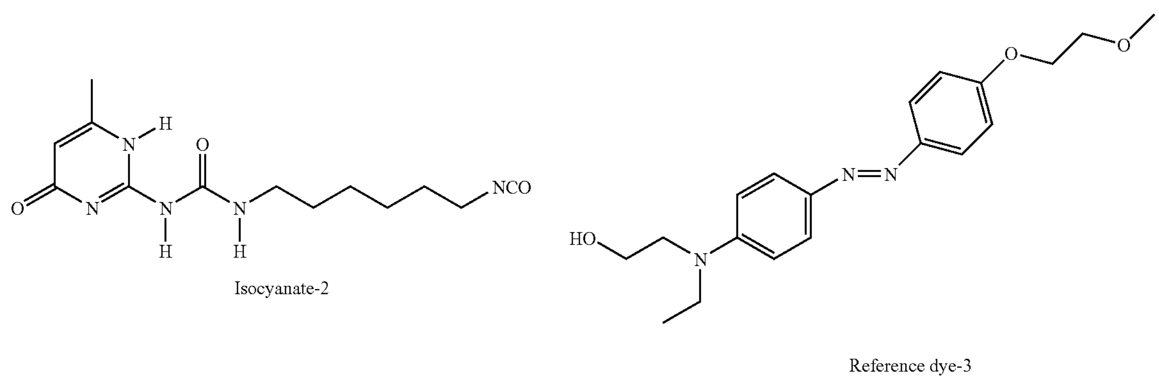
Isocyanate-2

Reference dye-3

DYE 135620
$CHCl_3$, reflux
dibutylin dilaurate

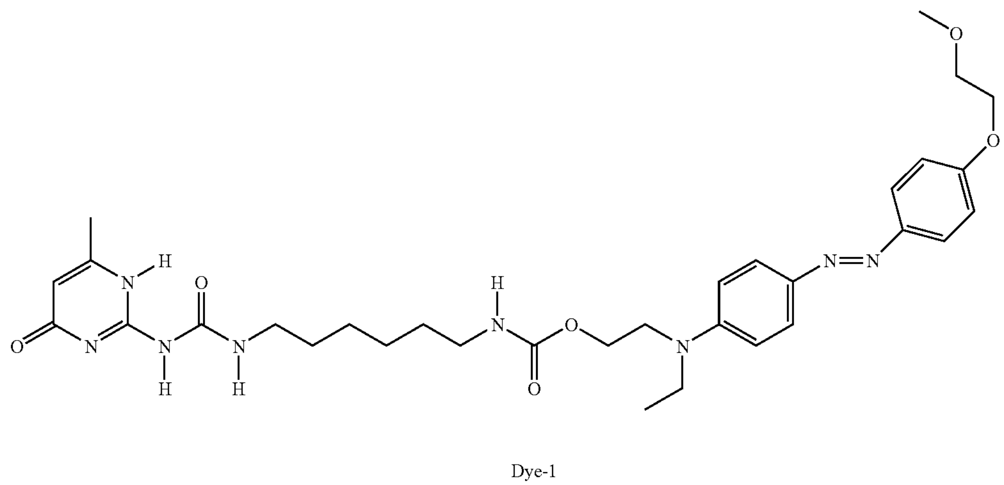
Dye-1

Reference dye-3 (17.4 gram) and the isocyanate-2 (prepared according to Example 1) (14.8 gram) were dissolved in 400 mL of dry chloroform. Several drops of the dibutyltin dilaurate catalyst were added and the reaction mixture was stirred under an argon atmosphere at an oil bath temperature of 80° C. for 21 hours. The reaction mixture was cooled to room temperature and added dropwise to 700 mL of hexane. The precipitated fine yellow powder was filtered and purified through a second precipitation from chloroform into a mixture of hexane/chloroform (500 mL/200 mL). 29.1 gram (90%) of Dye-1 was obtained.

1H NMR (300 MHz, $CDCl_3$): δ=1.1–1.7 (m, 11H), 2.1 (s, 3H), 3.0–3.2 (m, 4H), 3.4 (m, 5H), 3.6 (m, 2H), 3.7 (m, 2H), 4.1 (m, 2H), 4.3 (m, 2H), 5.15 and 5.2 (2s, 1H), 5.8 (s, 1H), 6.75 (d, 2H), 6.95 (d, 2H), 7.8 (d, 4H), 10.1 (s, 1H), 11.7 (s, 1H), 13.1 (s, 1H). MALDI-TOF MS (FW=636.75), found m/z=637.13. IR: ν (cm−1)=666, 750, 823, 837, 923, 942, 1003, 1035, 1058, 1105, 1132, 1151, 1194, 1240, 1315, 1361, 1377, 1396, 1446, 1511, 1546, 1583, 1667, 1682, 1700, 2929, 3290. λmax=409 nm; ε=26321 (CHCl3); λmax=409 nm; ε=29000 (MeOH).

Synthesis Example 3

This example discloses the synthesis of Dye-2.

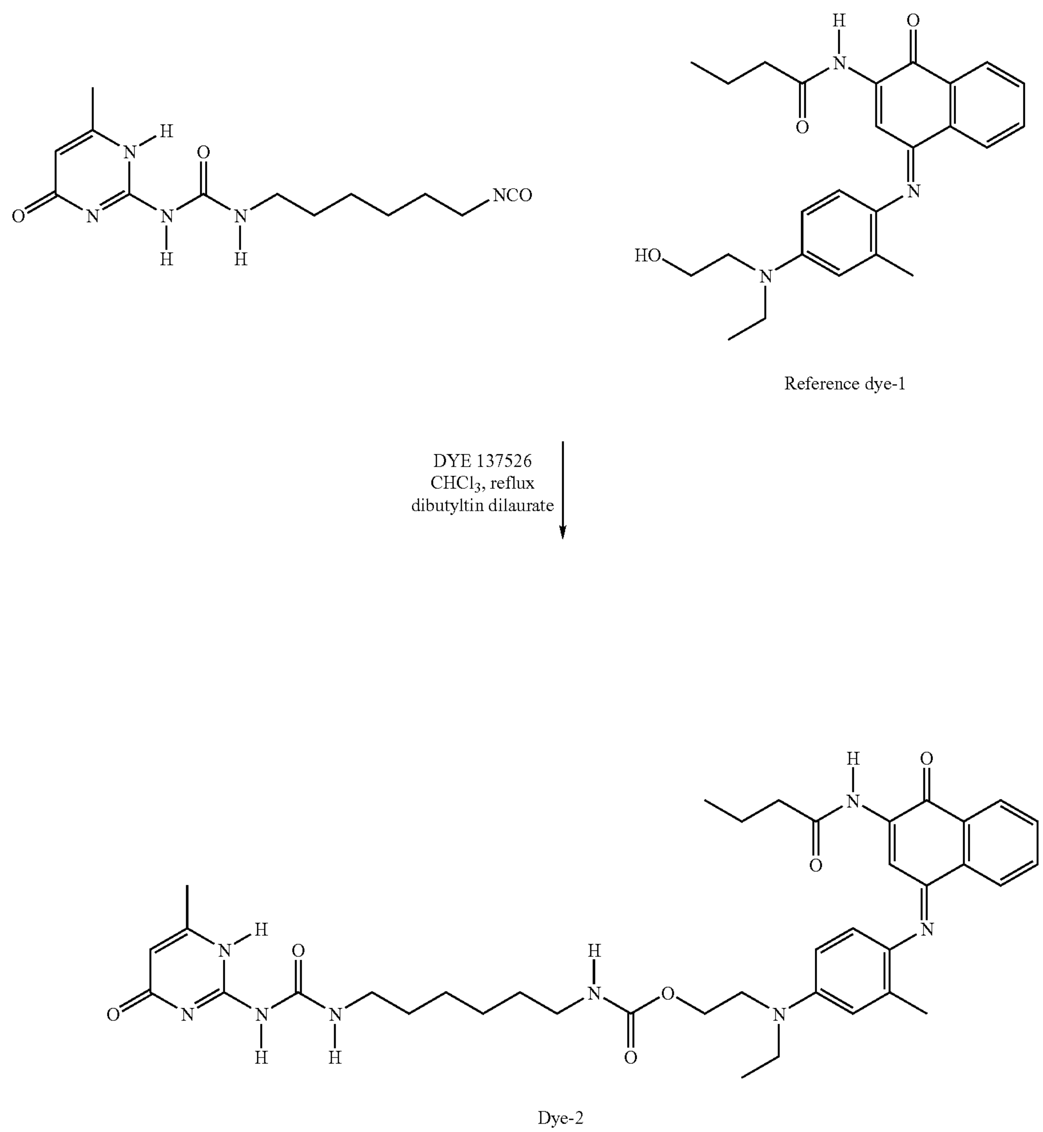

Reference dye-3 (17.4 gram) and the isocyanate-2 (prepared according to Example 1) (14.8 gram) were dissolved in 400 mL of dry chloroform. Several drops of the dibutyltin dilaurate catalyst were added and the reaction mixture was stirred under an argon atmosphere at an oil bath temperature of 80° C. for 21 hours. The reaction mixture was cooled to room temperature and added dropwise to 700 mL of hexane. The precipitated fine yellow powder was filtered and purified through a second precipitation from chloroform into a mixture of hexane/chloroform (500 mL/200 mL). 29.1 gram (90%) of Dye-1 was obtained.

1H NMR (300 MHz, $CDCl_3$): δ=1.1–1.7 (m, 11H), 2.1 (s, 3H), 3.0–3.2 (m, 4H), 3.4 (m, 5H), 3.6 (m, 2H), 3.7 (m, 2H), 4.1 (m, 2H), 4.3 (m, 2H), 5.15 and 5.2 (2s, 1H), 5.8 (s, 1H), 6.75 (d, 2H), 6.95 (d, 2H), 7.8 (d, 4H), 10.1 (s, 1H), 11.7 (s, 1H), 13.1 (s, 1H). MALDI-TOF MS (FW=636.75), found m/z=637.13. IR: ν (cm−1)=666, 750, 823, 837, 923, 942, 1003, 1035, 1058, 1105, 1132, 1151, 1194, 1240, 1315, 1361, 1377, 1396, 1446, 1511, 1546, 1583, 1667, 1682, 1700, 2929, 3290. λmax=409 nm; ϵ=26321 (CHCl3); λmax=409 nm; ϵ=29000 (MeOH).

Synthesis Example 4

This example discloses the synthesis of Dye-3.

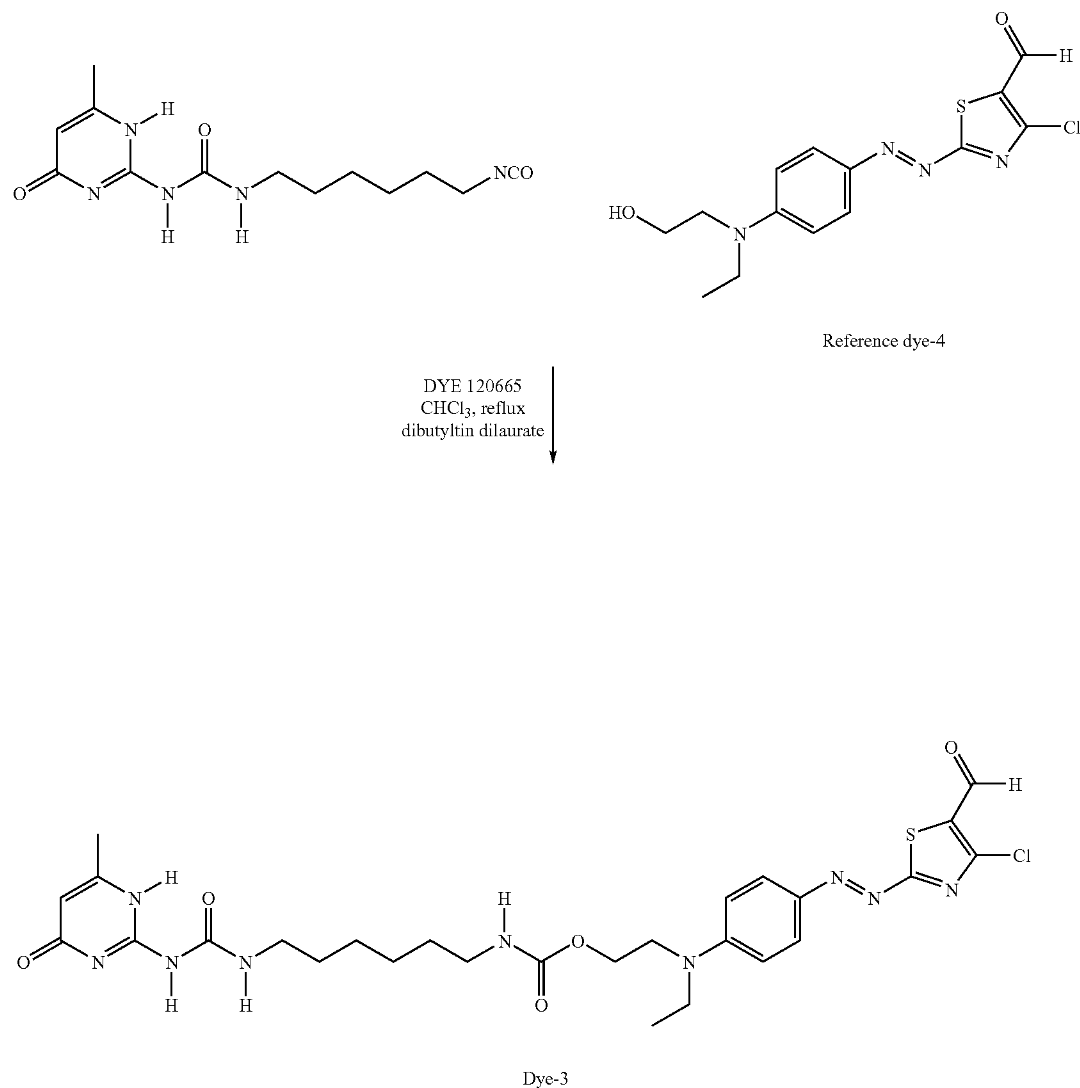

Reference dye-4 (706 mg) and the isocyanate-2 (579 mg) were dissolved in 50 mL of dry chloroform. Several drops of dibutyltin dilaurate (catalyst) were added, and the reaction mixture was boiled under an argon atmosphere for 21 hours. The reaction mixture was cooled to room temperature and the solvent was removed under reduced pressure. The compound was purified using column chromatography starting with pure chloroform as the eluent and gradually switching to 2% methanol in chloroform. The collected product was precipitated in hexane (to remove the catalyst) to yield 1.15 gram of Dye-3 (92%).

1H NMR (300 MHz, $CDCl_3$): δ=1.1–1.6 (m, 11H), 2.2 (s, 3H), 3.2 (m, 4H), 3.6 (m, 2H), 3.7 (m, 2H), 4.3 (m, 2H), 5.2–5.4 (2s, 1H), 5.8 (s, 1H), 6.8 (m, 2H), 7.9 (d, 2H), 10.0 (s, 1H), 10.1 (s, 1H), 11.7 (s, 1H), 13.1 (s, 1H). MALDI-TOF MS (FW=632.12), found m/z=632.14.

IR: ν (cm−1)=653, 664, 684, 721, 799, 826, 880, 926, 997, 1072, 1101, 1215, 1242, 1309, 1327, 1372, 1411, 1445, 1482, 1519, 1581, 1595, 1658, 1697, 2856, 2928, 3214. λmax=555 nm; ε=44000 (CHCl3); λmax=547 nm; ε=38000 (MeOH).

Synthesis Example 5

This example discloses the synthesis of Dye-4.

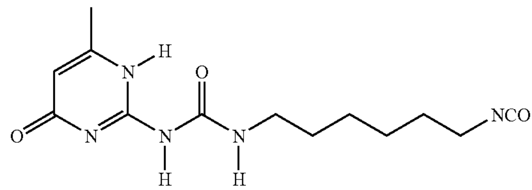

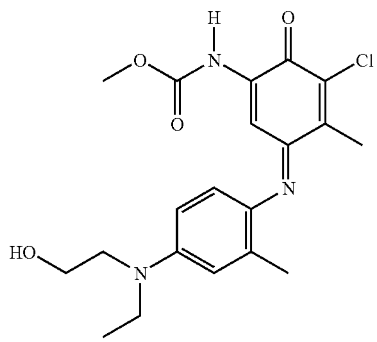

Reference dye-2

DYE 315414
$CHCl_3$, reflux
dibutyltin dilaurate

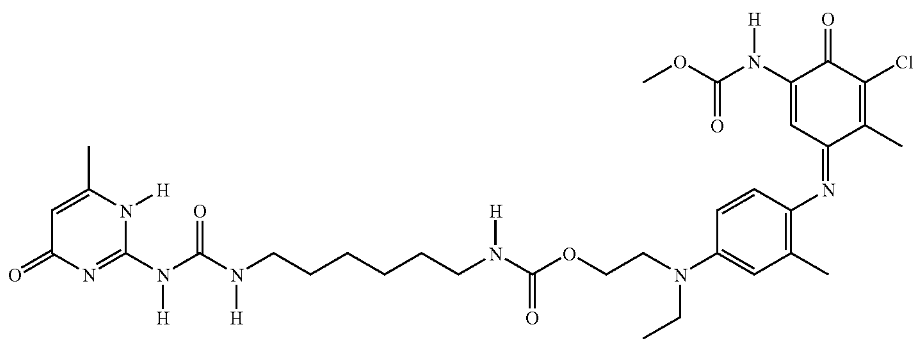

Dye-4

Reference Dye-2 (9.9 gram) and the isocyanate-2 (7.2 gram) were dissolved in 300 mL of dry chloroform. Several drops of dibutyltin dilaurate (catalyst) were added and the reaction mixture was refluxed for 21 hours under an argon atmosphere. The reaction mixture was cooled to room temperature and added dropwise to 700 mL of hexane. After a second precipitation Dye-4 is obtained as a blue powder: 16.1 gram (92%).

1H NMR (300 MHz, $CDCl_3$): δ=1.2 (t, 3H), 1.3 (m, 4H), 1.4–1.6 (m, 4H), 2.2 (s, 3H), 2.3 (s, 3H), 2.5 (s, 3H), 3.0–3.2 (m, 4H), 3.4 (m, 2H), 3.5 (m, 2H), 3.7 (s, 3H), 4.2 (m, 2H), 5.1 and 5.3 (2s, 1H), 5.8 (s, 1H), 6.6 (m, 2H), 6.8 (d, 1H), 7.6 (s, 1H), 7.9 (s, 1H), 10.1 (s, 1H), 11.7 (s, 1H), 13.1 (s, 1H). MALDI-TOF MS (FW=699.20), found m/z=700.25. IR: ν (cm−1)=664, 750, 784, 804, 843, 875, 917, 968, 1042, 1110, 1135, 1179, 1243, 1318, 1348, 1375, 1393, 1455, 1514, 1583, 1630, 1660, 1698, 1700, 2858, 2929, 3216, 3374. λmax=653 nm; ε=26000 (CHCl3); λmax=652 nm; ε=21000 (MeOH).

Synthesis Example 6

This example discloses the synthesis of Dye-5.

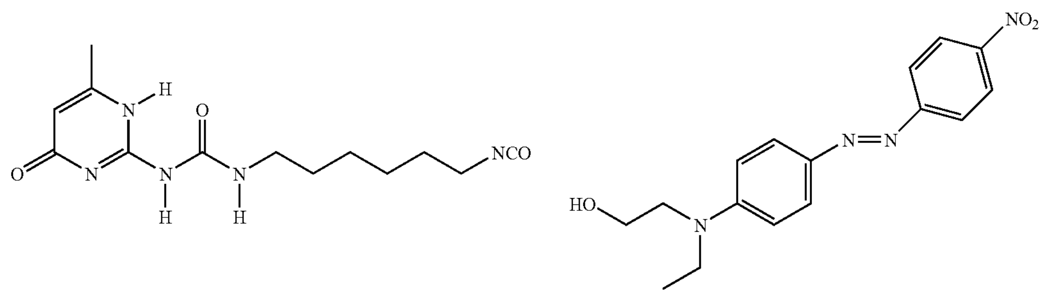

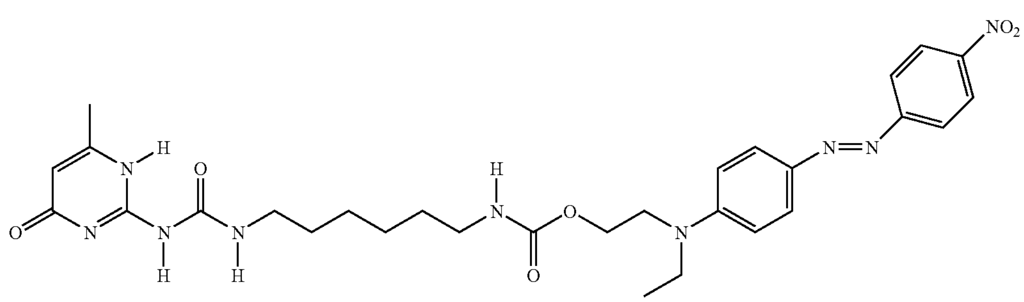

Dye-5

Reference dye-5 (1.0 gram) and the isocyanate-2 (1.0 gram) were mixed in 20 mL dry CHCl3 and 5 mL dry pyridine. Several drops of dibutyltin dilaurate (catalyst) were added and the reaction mixture was boiled and stirred under an argon atmosphere for several hours. The mixture was cooled. Evaporation and co-evaporation with toluene removed the solvent. Dye-5 was obtained as a red powder.

1H NMR (300 MHz, $CDCl_3$): δ=3.1–3.3 (m, 4H), 3.5 (m, 2H), 3.7 (m, 2H), 4.2 (m, 2H), 5.0–5.2 (2s, 1H), 5.8 (s, 1H), 6.8 (m, 2H), 7.9 (m, 4H), 8.3 (m, 2H), 10.1 (s, 1H), 11.7 (s, 1H), 13.1 (s, 1H).

MALDI-TOF MS (FW=607.7), found m/z=608.2. IR: ν (cm−1)=689, 741, 767, 798, 858, 943, 1041, 1105, 1133, 1194, 1251, 1311, 1338, 1384, 1446, 1512, 1590, 1662, 1698, 2857, 2932, 3230. λmax=479 nm (CHCl3); λmax=476 nm (MeOH).

Synthesis Example 7

This example discloses the synthesis of Dye-6.

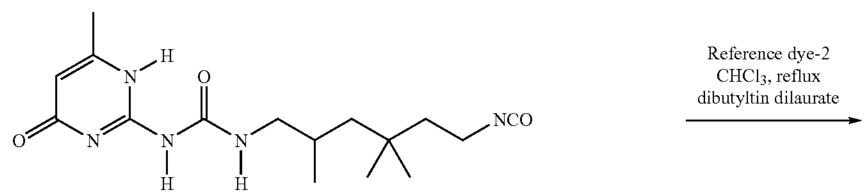

-continued

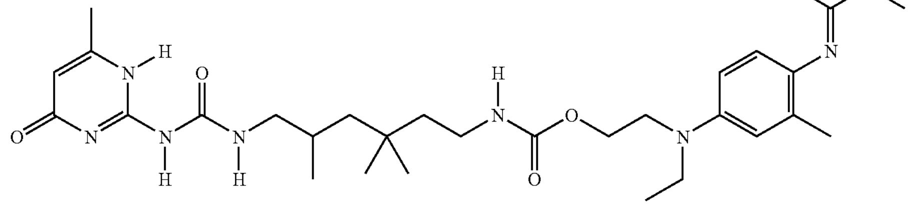

Dye-6

The isocyanate-1 (2.0 g; 5.96 mmol) and reference dye-2 (see example 5) (2.43 g; 5.99 mmol) were dissolved in 120 mL of dry chloroform. A few drops of dibutyltin dilaurate catalyst were added and the mixture was refluxed for 24 hours under an argon atmosphere. The reaction was monitored with TLC (2% MeOH/$CHCl_3$). Silica was added and the suspension was stirred for a few hours, followed by filtration. The filtrate was concentrated and the residue was dissolved in chloroform and precipitated in pentane to remove the catalyst; further purification was achieved with column chromatography (starting with pure chloroform as eluent and changing to 2% MeOH in chloroform). After chromatography, Dye-6 was precipitated from chloroform in pentane. Yield 3.28 gram (75%).

1H NMR (300 MHz, $CDCl_3$): δ=0.9–1.0 (m, 10H), 1.2–1.4 (m, 4H), 1.5–1.7 (m, 3H), 2.2 (s, 3H), 2.3 (s, 3H), 2.5 (s, 3H), 3.0 (m, 2H), 3.2 (m, 2H), 3.5 (m, 2H), 3.6 (m, 2H), 3.7 (s, 3H), 4.2 (m, 2H), 5.2–5.4 (2s, 1H), 5.8 (s, 1H), 6.6 (m, 2H), 6.75 (d, 1H), 7.7 (s, 1H), 7.9 (s, 1H), 10.1 (s, 1H), 11.7 (s, 1H), 13.1 (s, 1H). IR: ν (cm−1)=666, 705, 745, 768, 784, 804, 842, 875, 917, 968, 1042, 1110, 1135, 1179, 1250, 1319, 1350, 1376, 1394, 1456, 1515, 1595, 1632, 1660, 1697, 1723, 2957, 3218, 3376. λmax=655 nm; ε=25000 ($CHCl_3$); λmax=647 nm; ε=21000 (MEK); λmax=638 nm; ε=24000 (EtOAc).

Synthesis Example 8

This example discloses the synthesis of Dye-7.

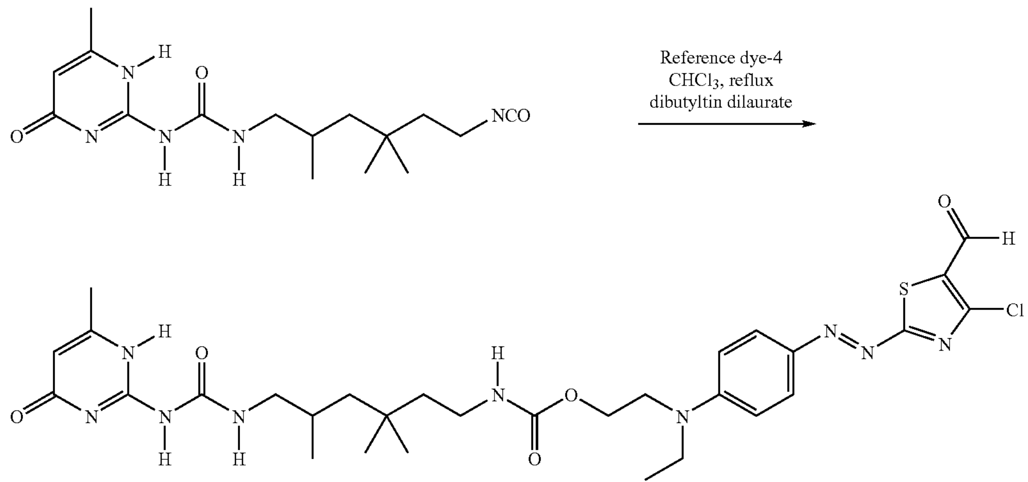

Dye-7

The isocyanate-1 (3.5 g; 10.4 mmol) and reference dye-4 (3.58 g; 10.6 mmol) were dissolved in 120 mL of dry chloroform. A few drops of dibutyltin dilaurate catalyst were added and the mixture was refluxed for 24 hours under argon. The reaction was followed with TLC (2% MeOH/$CHCl_3$). Silica was added and the suspension was stirred for a few hours, followed by filtration. The filtrate was concentrated under reduced pressure and the residue was dissolved in chloroform and precipitated in pentane to remove the catalyst; further purification was achieved with column chromatography (starting with pure chloroform as eluent and changing to 2% MeOH in chloroform; alternatively, EtOAc/hexane mixtures can be used). After chromatography, Dye-7 was precipitated from chloroform into pentane. Yield 4.2 gram (60%).

1H NMR (300 MHz, $CDCl_3$): δ 0.9 (m, 9H), 1.0–1.8 (8H), 2.2 (s, 3H), 2.8–3.0 (m, 4H), 3.5 (m, 2H), 3.7 (m, 2H), 4.3 (m, 2H), 5.2–5.4 (1H), 5.8 (s, 1H), 6.8 (m, 2H), 7.9 (m, 2H), 10.1 (m, 2H), 11.9 (bs, 1H), 13.1 (bs, 1H).

FT-IR: ν (cm−1)=666, 684, 721, 761, 796, 826, 880, 925, 997, 1013, 1073, 1123, 1218, 1244, 1310, 1327, 1372, 1411, 1482, 1520, 1597, 1660, 1698, 2957. λmax=553 nm; ϵ=3700 (CHCl3); λmax=561 nm; ϵ=39000 (MEK); λmax=553 nm; ϵ=36000 (EtOAc).

Synthesis Example 9

This example discloses the synthesis of Dye-8.

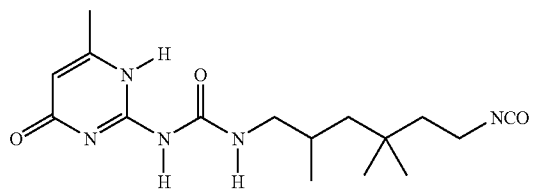

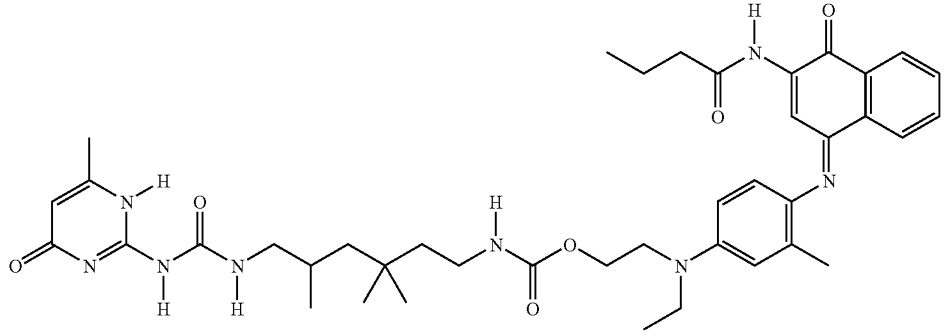

Dye-8

The isocyanate-1 (2.0 g; 5.96 mmol) and reference dye-1 (2.5 g; 5.96 mmol) were dissolved in 120 mL of dry chloroform. A few drops of dibutyltin dilaurate catalyst were added and the mixture was refluxed for 96 hours under argon. The reaction was followed with TLC (2% MeOH/$CHCl_3$). Silica was added and the suspension was stirred for a few hours, followed by filtration. The filtrate was concentrated under reduced pressure and the residue was dissolved in chloroform and precipitated in pentane to remove the catalyst; further purification was achieved with column chromatography (starting with pure chloroform as eluent and changing to 2% MeOH in chloroform; alternatively, EtOAc/hexane mixtures can be used). After chromatography, Dye-8 was precipitated from chloroform into pentane. Yield: 60%.

1H NMR (300 MHz, $CDCl_3$): δ 0.9–1.9 (22H), 2.2 (s, 3H), 2,4 (s, 3H), 3.0 (m, 2H), 3.2 (m, 2H), 3.4 (m, 4H), 3.6 (m, 2H), 4.3 (t, 2H), 5.2–5.4 (1H), 5.8 (s, 1H), 6.6 (d, 1H), 6.7 (m, 2H), 7.6 (t, 1H), 7.7 (t, 1H), 8.2 (d, 1H), 8.48 (s 1H), 8.55 (d, 1H), 9.3 (t, 1H), 10.1 (bs, 1H), 11.9 (bs, 1H), 13.1 (bs, 1H).

FT-IR: ν (cm−1)=696, 754, 797, 841, 936, 1029, 1072, 1100, 1138, 1193, 1246, 1318, 1354, 1393, 1447, 1470, 1501, 1532, 1580, 1607, 1660, 1698, 2958. λmax=684 nm; ϵ=25000 (CHCl3); λmax=679 nm; 6=22000 (MEK); λmax=680 nm; ϵ=22000 (EtOAc).

Synthesis Example 10

This example discloses the synthesis of Dye-9.

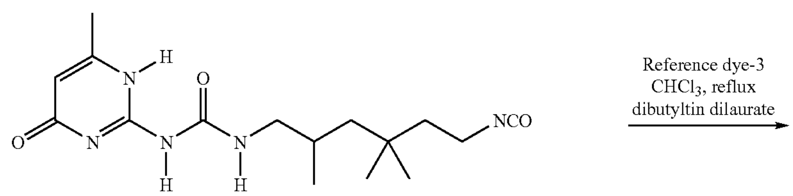

-continued

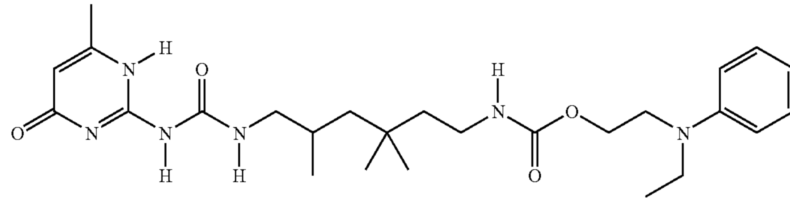

The isocyanate-1 (6.15 g; 18.3 mmol) and reference dye-3 (6.00 g; 17.5 mmol) were dissolved in 180 mL of dry chloroform. A few drops of dibutyltin dilaurate catalyst were added and the mixture was refluxed for 24 hours under argon. The reaction was followed with TLC (2% MeOH/$CHCl_3$) and IR. The reaction mixture was evaporated under reduced pressure and the residue was precipitated from chloroform into pentane to remove the catalyst. The compound was then purified with column chromatography (starting with 1/1 EtOAc/hexane as eluent and changing gradually to 3/1 EtOAc/hexane; the product was collected by eluting with 4% MeOH in chloroform). After chromatography, dye-9 was precipitated from chloroform into pentane.

1H NMR (300 MHz, $CDCl_3$): δ 0.9 (m, 9H), 1.0–1.8 (8H), 2.2 (s, 3H), 3.0 (m, 2H), 3.3 (m, 2H), 3.5 (m, 5H), 3.6 (m, 2H), 3.8 (m, 2H), 4.2–4.4 (m, 4H), 5.0–5.4 (three m, 1H), 5.8 (s, 1H), 6.8 (m, 2H), 7.0 (d, 2H), 7.8 (m, 4H), 10.1 (m, 1H), 11.9 (bs, 1H), 13.1 (bs, 1H).

FT-IR: ν (cm−1)=664, 731, 775, 821, 836, 924, 1033, 1060, 1133, 1149, 1196, 1242, 1316, 1355, 1396, 1447, 1511, 1581, 1594, 1660, 1697, 2956, 3216. λ=409 nm; ϵ=29112 ($CHCl_3$).

Synthesis Example 11

This example discloses the synthesis of Dye-10.

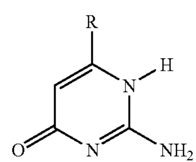

R = 1-ethylpentyl

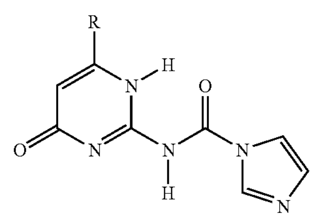

CDI Activation of 6-(1-ethylpentyl)isocytosine.

6-(1-Ethylpentyl)-isocytosine (3.0 gram, 14.4 mmol) and carbonyldiimidazole (CDI; 3.24 gram, 20 mmol) were stirred at room temperature in 40 mL $CHCl_3$ for two hours, during which the mixture was kept under an argon atmosphere. The solution was washed with an aqueous NaCl solution, dried with $MgSO_4$ and concentrated to give a quantitative yield of CDI-activated product. NMR analyses showed signals at the expected resonances and no traces of excess CDI were discerned. (The isocytosine starting product had been prepared by a standard coupling procedure of its β-keto ester precursor and guanidine carbonate).

1H NMR ($CDCl_3$), λ=12.9 (2H, bs), 8.6 (1H, s), 7.5 (1H, s), 6.9 (1H, s), 5.7 (1H, s), 2.4 (1H, m), 1.6 (4H, m), 1.2 (4H, m), 0.95–0.7 (6H, m).

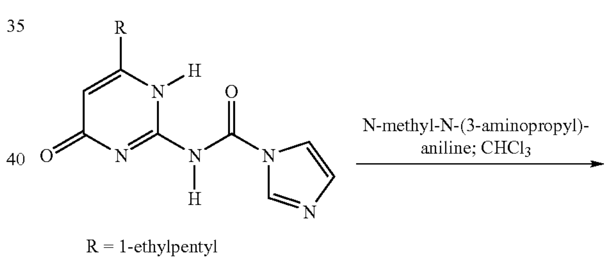

R = 1-ethylpentyl

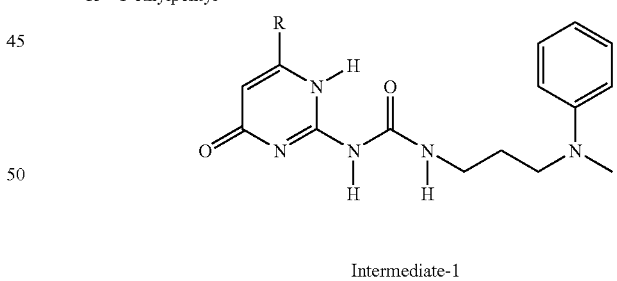

Intermediate-1

Synthesis of Intermediate-1.

The CDI-activated product of (1-ethylpentyl)-isocytosine (4.3 gram, 14.4 mmol) was stirred overnight at room temperature in $CHCl_3$ together with N-methyl-N-(3-aminopropyl)-aniline (2,45 gram, 15 mmol). The solution was subsequently washed with a HCl solution and a NaHCO3 solution, and thereafter dried and concentrated. Column chromatography over silica with hexane/EtOAc 1/1 gave 4.8 gram of Intermediate-1 (85%). The oil solidified on standing.

1H NMR ($CDCl_3$), δ=13.2 (1H, s), 12.0 (1H, s), 10.3 (1H, s), 7.2 and 6.7 (5H), 5.8 (1H, s), 3.5–3.3 (4H, m), 3.0 (3H, s), 2.3 (1H, m), 1.9 (2H, m), 1.8–1.5 (4H, m), 1.3 (4H, m), 0.95–0.8 (6H, m).

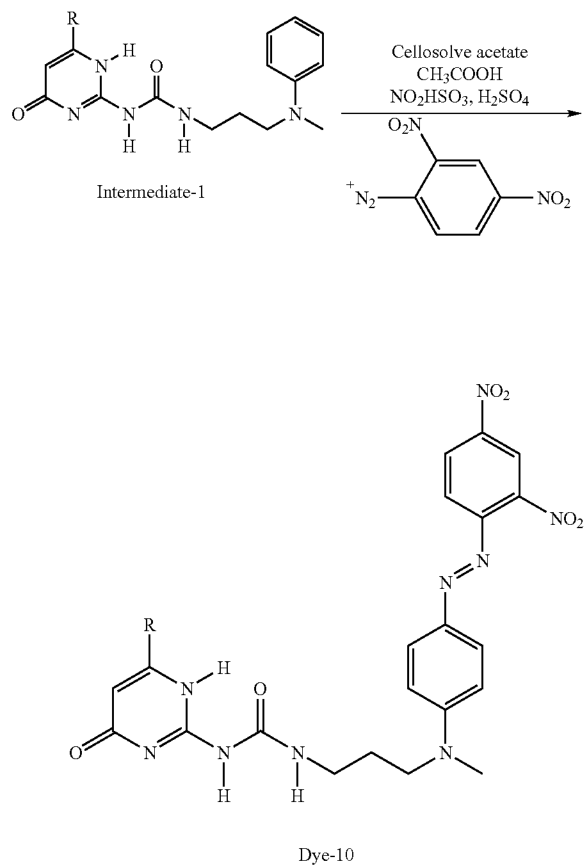

Synthesis of Dye-10.

2,4-Dinitroaniline (0.6 gram, 3.3 mmol) was suspended in 4.5 mL of acetic acid and 0.6 mL of $H_2SO_4$. A 40% solution of nitrosyl sulfuric acid ($NO_2HSO_3$, 0.9 gram, 2.8 mmol) in $H_2SO_4$ was added to this mixture, while remaining the mixture at 15° C. Stirring was continued for 30 minutes. The resulting yellow solution was added dropwise to a cooled solution of Intermediate-1 (0.5 gram, 1.26 mmol) in 4 mL of cellosolve acetate. The mixture turned red and was stirred overnight, while the temperature of the mixture was allowed to rise from 5° C. to room temperature. The clear mixture was poured on crushed ice to yield a purple-reddish solid that was filtered and washed with water. The product was dissolved in $CHCl_3$, washed twice with a $NaHCO_3$ solution, and once with a saturated NaCl solution. After drying over $MgSO_4$, and concentration, the product was dissolved in $CHCl_3$ and a small amount of acetic acid, and this solution was added dropwise to warm ethanol, yielding pure Dye-10 (0.37 gram, 50%).

1H NMR ($CDCl_3$), δ=13.1 (1H, s), 12.0 (1H, s), 10.4 (1H, s), 8.7 (1H, s), 8.4 (1H, d), 7.9 (3H, m), 6.8 (2H, d), 5.8 (1H, s), 3.6 (2H, m), 3.4 (2H, m), 3.2 (3H, s), 2.3 (1H, m), 2.0 (2H, m), 1.7–1.5 (4H, m), 1.3 (4H, m), 0.9 (6H, m).

Synthesis Example 12

This example discloses the general procedure for consecutive triple modification of cyanuric chloride.

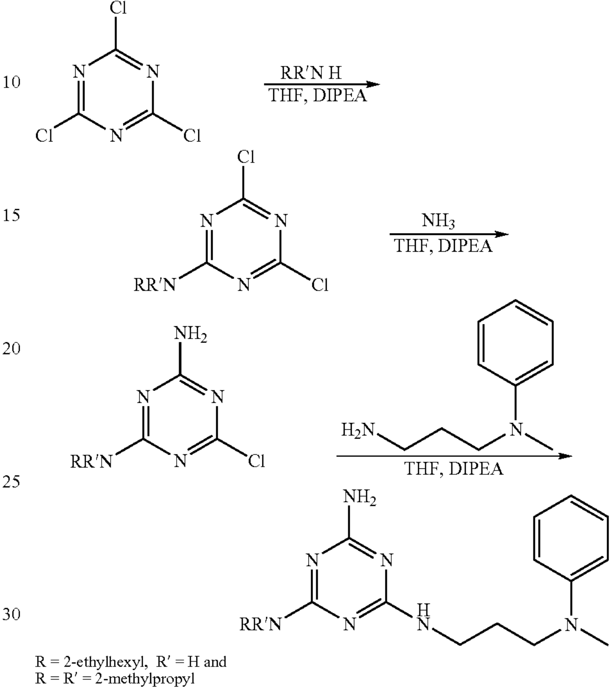

First step. Cyanuric chloride in THF was added to a solution of 2-ethylhexyl amine (or diisobutyl amine) and diisopropyl amine (both 1.05 equivalents) in THF. The reaction mixture was stirred and maintained at −5° C. The reaction was complete after about 2 hours, as confirmed by TLC and GC-MS analysis. The product was purified by addition of dichloromethane, washing with a NaHCO3 solution and drying with $Na_2SO_4$.

Second step. The mono-functionalized cyanuric chloride derivative was stirred in THF together with 1.05 equivalents of diisopropylethyl amine. After cooling of the mixture to 0° C., $NH_3$ gas was gently flushed through the solution. The temperature was allowed to rise to 15° C.; TLC and GC-MS were used to establish whether the reaction had gone to completion. Dichloromethane was added, the mixture was washed with a $NaHCO_3$ solution and was dried with $MgSO_4$. Crystallization from methanol or toluene yielded pure product.

Third step. The bi-functionalized cyanuric chloride derivative was stirred overnight in boiling dioxane together with N-methyl-N-(3-amino propyl)-aniline and diisopropylethyl amine (both 1.1 equivalents). After cooling, dichloromethane was added and the mixture was washed with a NaHCO3 solution and dried with $MgSO_4$. Column chromatography on silica with a $CHCl_3$/MeOH mixture yielded pure oils.

R=2-ethylhexyl, R'=H: 1H NMR ($CDCl_3$), δ=7.3 (2H, m), 6.7 (3H, m), 6.0–5.3 (4H, bm), 3.5–3.2 (6H, m), 2.9 (3H, s), 1.9 (2H, m), 1.5 (1H, m), 1.3 (8H, m), 0.9 (6H, m).

R=R'=isobutyl: 1H NMR ($CDCl_3$), δ=7.2 (2H, m), 6.7 (3H, m), 5.1 (1H, bs), 4.8 (2H, bs), 3.4 (8H, m), 2.9 (3H, s), 2.1 (2H, m), 1.9 (2H, m), 0.9 (12H, d).

Synthesis Example 13

This example discloses the synthesis of Dye-11.

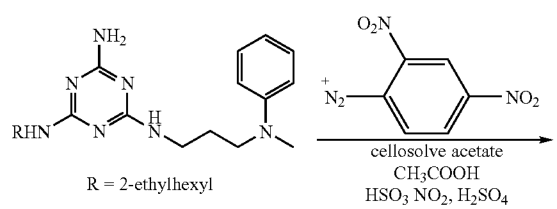

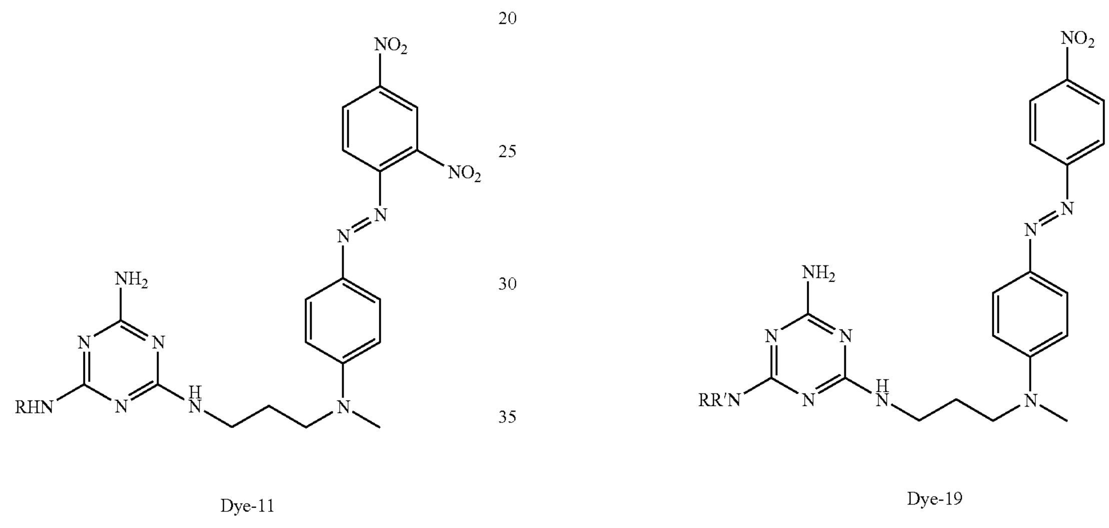

Dye-11

Dye-19

2,4-Dinitroaniline (1.1 gram, 6.0 mmol) was suspended in 9 mL of acetic acid and 1.2 mL of H2SO4; addition of a 40% nitrosyl sulfuric acid ($NO_2HSO_3$, 1.8 gram, 5.7 mmol) solution in $H_2SO_4$ gave an almost clear yellow solution that was stirred for 30 minutes, while keeping the temperature at about 15° C. The diazonium salt solution was added dropwise to a cooled (5–10° C.) solution of the precursor-triazine (1 gram, 2.6 mmol) in 16 mL of cellosolve acetate. Upon addition the mixture became reddish. The clear reaction mixture was stirred overnight, and was poured onto ice to give a purple solid. The solid was filtered, washed and dissolved in $CHCl_3$. The solution was washed with a $NaHCO_3$ solution and with brine, and was then dried over $MgSO_4$. The crude product was purified by column chromatography in CHCl3 with 2% MeOH eluent and was thereafter precipitated from a $CHCl_3$ solution into pentane to yield Dye-11 as a purple powder.

1H NMR ($CDCl_3$), δ=8.7 (1H, s), 8.4 (1H, d), 7.9 (3H, m), 6.7 (2H, d), 5.4–4.8 (4H, bs), 3.6–3.0 (9H, m), 2.0 (2H, m), 1.6–1.2 (9H, m), 1.0–0.9 (6H, m). λmax=524 nm; ε=33068 (CHCl3). MALDI-TOF MS, $[M+H^+]$=580.

Synthesis Example 14

This example discloses the synthesis of Dye-19.

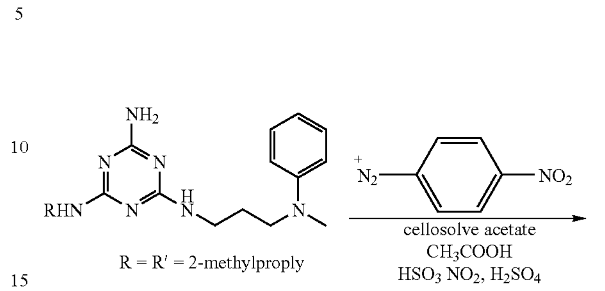

4-Nitroaniline (0.9 gram, 6.5 mmol) was suspended in 9 mL of acetic acid and 1.2 mL of $H_2SO_4$; addition of a 40% nitrosyl sulfuric acid ($NO_2HSO_3$, 2.1 gram, 6.6 mmol) solution in $H_2SO_4$ gave an almost clear yellow solution that was stirred for 30 minutes, while keeping the temperature at about 10° C. The diazonium salt solution was added dropwise to a cooled (5–10° C.) solution of the precursor triazine (1 gram, 2.6 mmol) in 16 mL of cellosolve acetate. A precipitate developed but redissolved during the reaction. The clear reaction mixture was poured onto ice, the mixture was made basic, and the red solid was isolated by filtration and subsequent washing with water. The product was dissolved in $CHCl_3$ and washed with a $NaHCO_3$ solution, followed by drying over $MgSO_4$. The crude product was purified by column chromatography in $CHCl_3$ with 2% MeOH eluent. Precipitation into pentane gave Dye-19 as a red powder (0.865 gram; 62%).

$^1H$ NMR ($CDCl_3$), δ=8.3 (2H, d), 7.9 (4H, m), 6.8 (2H, d), 5.1 (1H, bs), 4.9 (2H, bs), 3.5–3.3 (8H, m), 3.1 (3H, s), 2.1 (2H, m), 1.9 (2H, m), 0.9 (12H, d).

MALDI-TOF MS, $[M+H^+]$=535.3.

UV: λmax ($CHCl_3$)=482 nm; ε=31000.

Synthesis Example 15

This example discloses the synthesis of Dye-12.

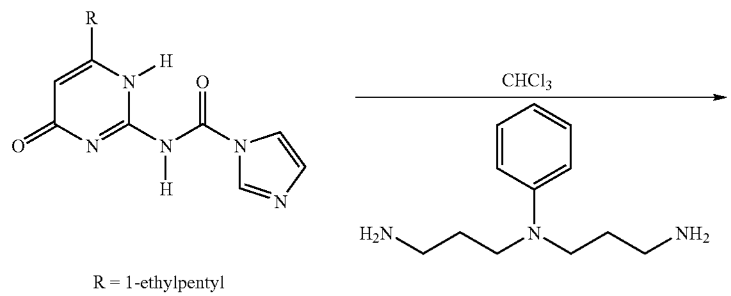

R = 1-ethylpentyl

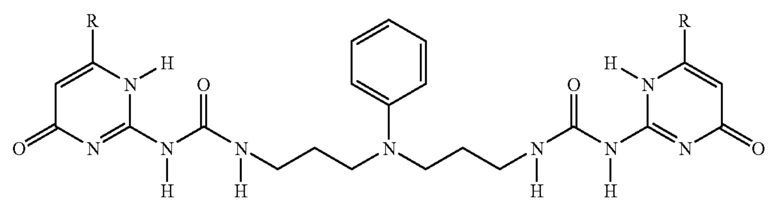

Intermediate-2

Synthesis of Intermediate-2.

The CDI-activated product of (1-ethylpentyl)-isocytosine (2.6 gram, 8.5 mmol, 2.2 equivalents) was stirred overnight at room temperature in $CHCl_3$ together with N-(bis-3-aminopropyl)-aniline (0.8 gram, 3.85 mmol). The solution was subsequently washed with a HCl solution and a NaHCO3 solution, and thereafter dried and concentrated. The product was dissolved in $CHCl_3$ and a small amount of acetic acid and was precipitated in ethanol. The suspension was heated until a clear solution was obtained. After cooling, pure Intermediate-2 was isolated as a white precipitate. (The diamine had been prepared by cyanoethylation of aniline, subsequent hydrogenation and purification by distillation under reduced pressure).

1H NMR ($CDCl_3$), δ=13.1 (2H, s), 12.0 (2H, s), 10.3 (2H, s), 7.4–7.0 and 6.8–6.5 (5H), 5.8 (2H, s), 3.5–3.3 (8H, m), 2.3 (2H, m), 2.0 (4H, m), 1.6 (8H, m), 1.3 (8H, m), 0.95–0.7 (12H, m).

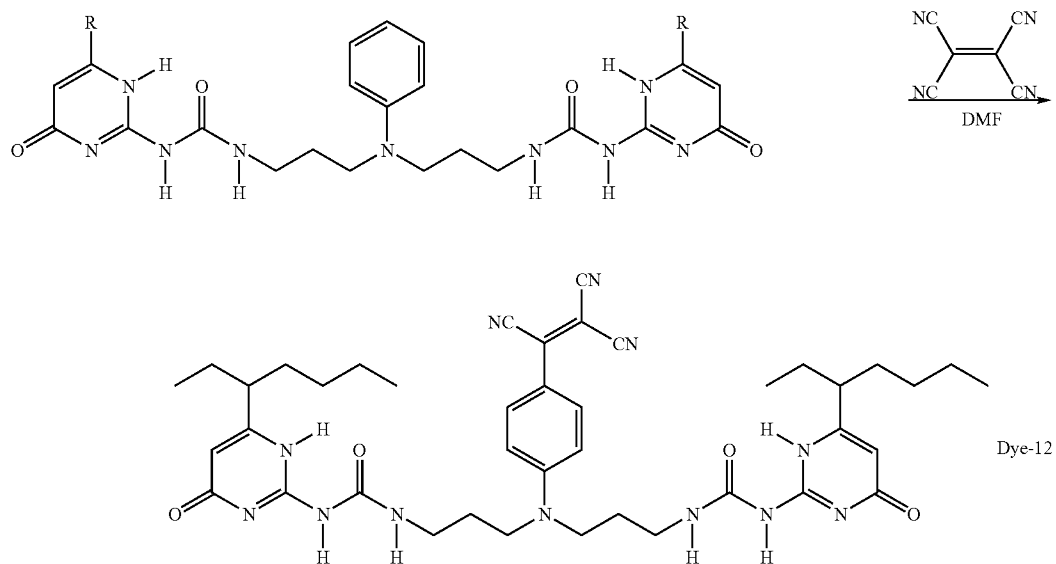

Synthesis of Dye-12.

Tetracyanoethylene (0.104 gram, 0.81 mmol) in 1.5 mL DMF was added dropwise to a heated (65° C.) suspension of Intermediate-2 (0.5 gram, 0.74 mmol) in 1.5 mL DMF. During addition a purple-reddish Colour developed (the reaction mixture was flushed with nitrogen, and the nitrogen was led through a NaOH/NaOCl trap to remove HCN). After the addition was complete, the mixture was stirred for 1.5 hours at 70° C. Addition of 6 mL ethanol, further stirring for an hour, cooling to room temperature and addition of some water resulted in a suspension that was filtered and washed with water and ethanol. After drying the structure of Dye-12 was confirmed by MALDI-TOF MS ([M+]=779, [M+Na+]=802, [M+K+]=818).

Synthesis Example 16

This example discloses the synthesis of Dye-13.

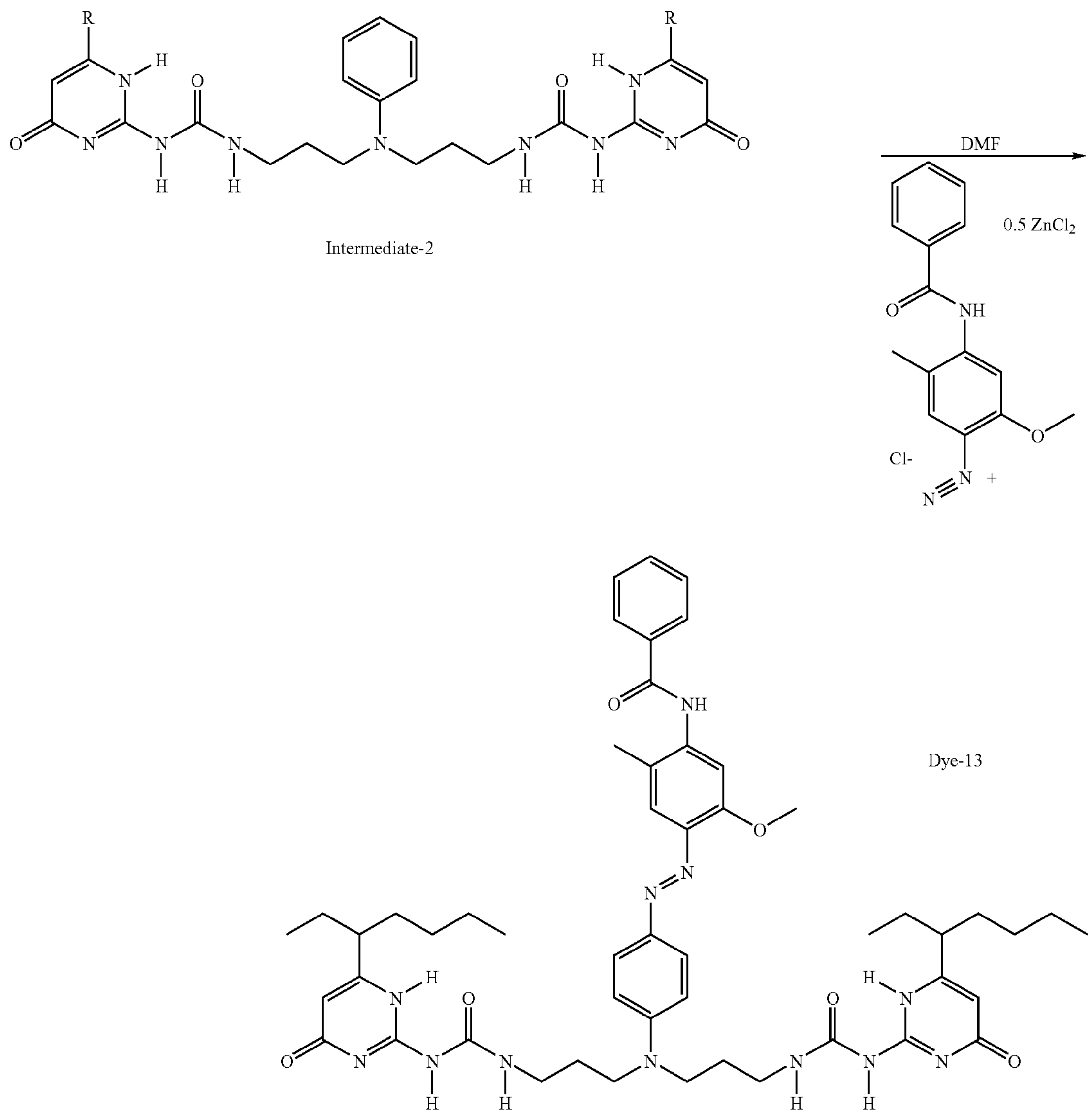

Intermediate-2 (0.25 gram, 0.37 mmol) was stirred in 5 mL DMF at 65° C. together with the commercial diazonium salt (fast violet B salt, 0.283 gram, 0.76 mmol). The mixture became homogeneous and dark and was stirred at the given temperature for 1.5 hours. After cooling, $CHCl_3$ was added and the mixture was washed with acidic water and with a $NaHCO_3$ solution. After drying and precipitation the precipitate was purified using column chromatography. MALDI-TOF MS analysis as well as NMR analysis confirmed the structure of Dye-13. ([M+H$^+$]=946, [M+Na+]=968).

Synthesis Example 17

This example discloses the synthesis of Dye-14.

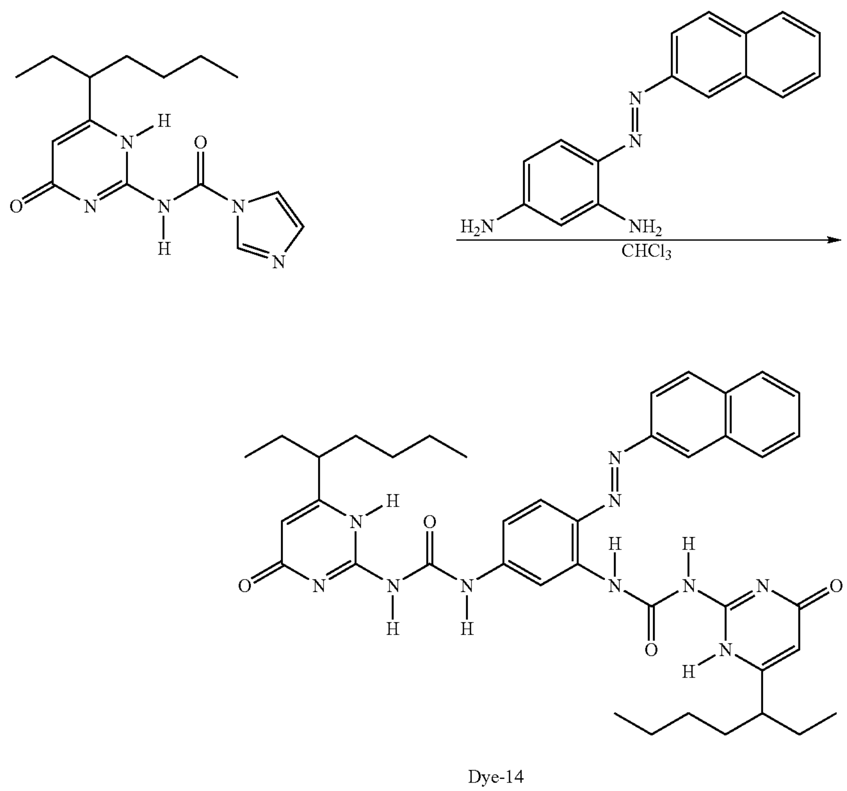

The activated 6-(1-ethylpentyl)isocytosine (2.8 gram; 9.3 mmol) was dissolved in 50 mL dry $CHCl_3$ together with Solvent Brown 1 (Fat Brown R R; C.I.11285)(1.06 gram, 4.0 mmol), and the mixture was heated in an oil bath of 80° C. for about 20 hours. Purification by column chromatography (silica; $CHCl_3$/MeOH, 98/2), and then by precipitation into acetone afforded Dye-14 as an orange solid.

1H NMR ($CDCl_3$, TFA-D1), δ=12.0 (6H, bs), 8.9 (1H, d), 8.4 (1H, bs), 8.0 (4H, m), 7.6 (4H, m), 6.3 (1H, s), 6.2 (1H, s), 2.6 (2H, m), 1.7 (8H, m), 1.4 (8H, m), 1.0 (12H, m). λmax=408 nm; ϵ=19868 ($CHCl_3$).

MALDI-TOF MS analysis, $[M+H^+]$=734, [M+Na+]=756, [M+K+]=772.

λmax=408 nm; ϵ=20000 ($CHCl_3$).

Synthesis Example 18

This example discloses the synthesis of Dye-15.

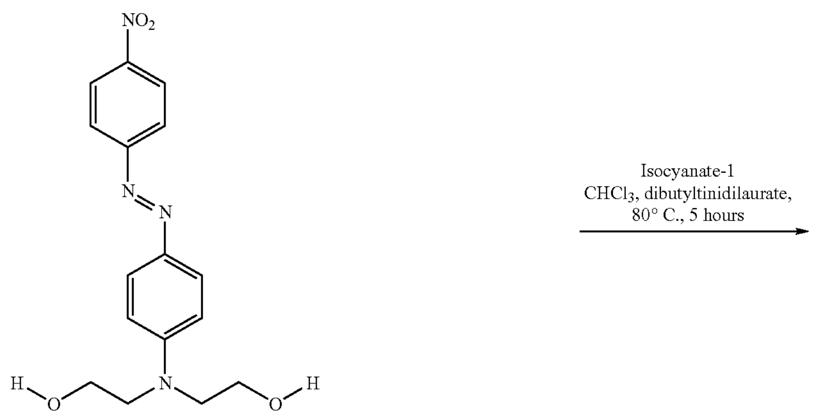

-continued

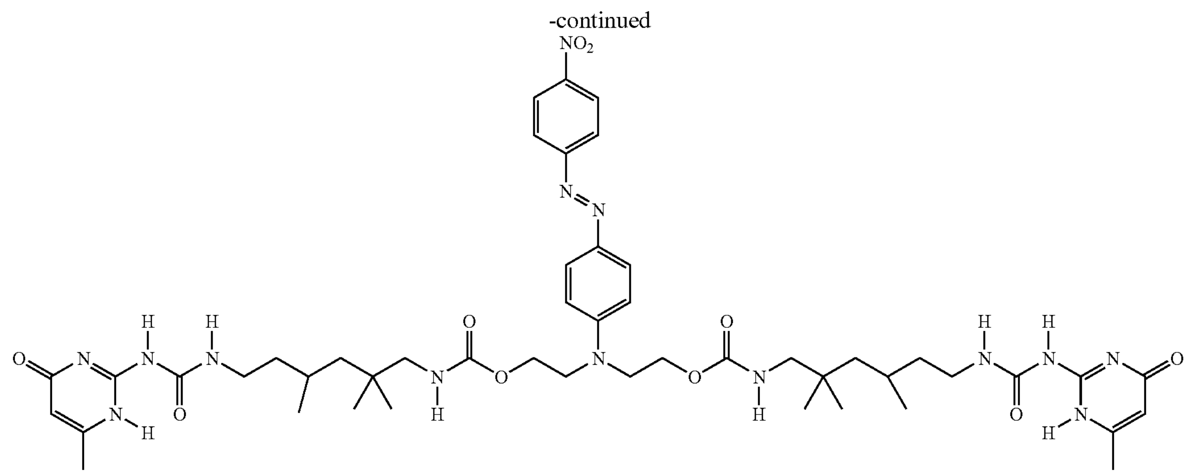

Dye-15

The starting diol (0.5 gram), Isocyanate-1 (1.11 gram) and a drop of dibutyltin dilaurate catalyst were mixed and heated in 100 mL of dry chloroform. After 24 hours of reflux, all isocyanate was consumed (FTIR analysis). The red product Dye-15 was isolated using column chromatography (silica, $CHCl_3$/MeOH, 98/2).

1H NMR ($CDCl_3$), δ=13.1 (2H, bs), 11.8 (2H, bs), 10.1 (2H, bs), 8.3 (2H, m), 7.9 (4H, m), 6.8 (2H, m), 5.8 (2H, s), 5.8–5.2 (2H), 4.2 (4H, m), 3.7 (4H, m), 3.3–2.8 (8H), 2.2 (6H, s), 1.8–1.2 (8H, m), 1.0 (20H, m). $\lambda_{max}$=464 nm; ϵ=28465 ($CHCl_3$).

MALDI-TOF MS analysis, [M+H+]=1001, [M+Na+]=1023.

λmax=464 nm; ϵ=28000 ($CHCl_3$).

Synthesis Example 19

This example discloses the synthesis of Dye-16.

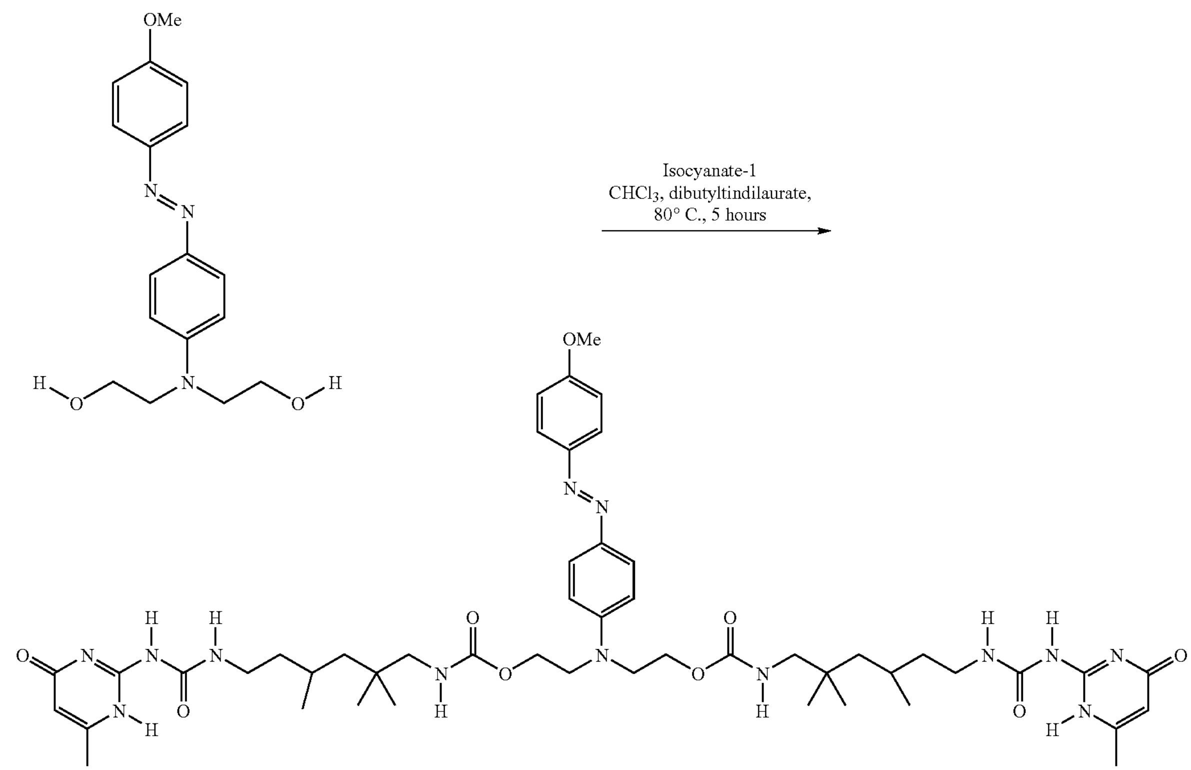

Dye-16

The starting diol (1 gram), Isocyanate-1 (2.3 gram) and a drop of dibutyltin dilaurate catalyst were mixed and heated in 100 mL of dry chloroform. After 40 hours of reflux isocyanate-1 was completely consumed (FTIR analysis). After column chromatography (silica, $CHCl_3$/MeOH, 98/2) Dye-16 (1.25 gram) was isolated as a yellow powder.

1H NMR ($CDCl_3$), δ=13.1 (2H, bs), 11.8 (2H, bs), 10.1 (2H, bs), 7.8 (4H, m), 6.9 (2H, m), 6.7 (2H, m), 5.8 (2H, s), 5.6–5.2 (2H), 4.2 (4H, m), 3.8 (3H, s), 3.6 (4H), 3.3–2.8 (8H), 2.2 (6H, s), 1.8–1.2 (8H, m), 1.0 (20H, m). $\lambda_{max}$=405 nm; ε=31920 ($CHCl_3$).

MALDI-TOF MS analysis, [M+H+]=985, [M+Na+]=1009.

$\lambda_{max}$=405 nm; ε=32000 ($CHCl_3$).

Synthesis Example 20

This example discloses the synthesis of Dye-17.

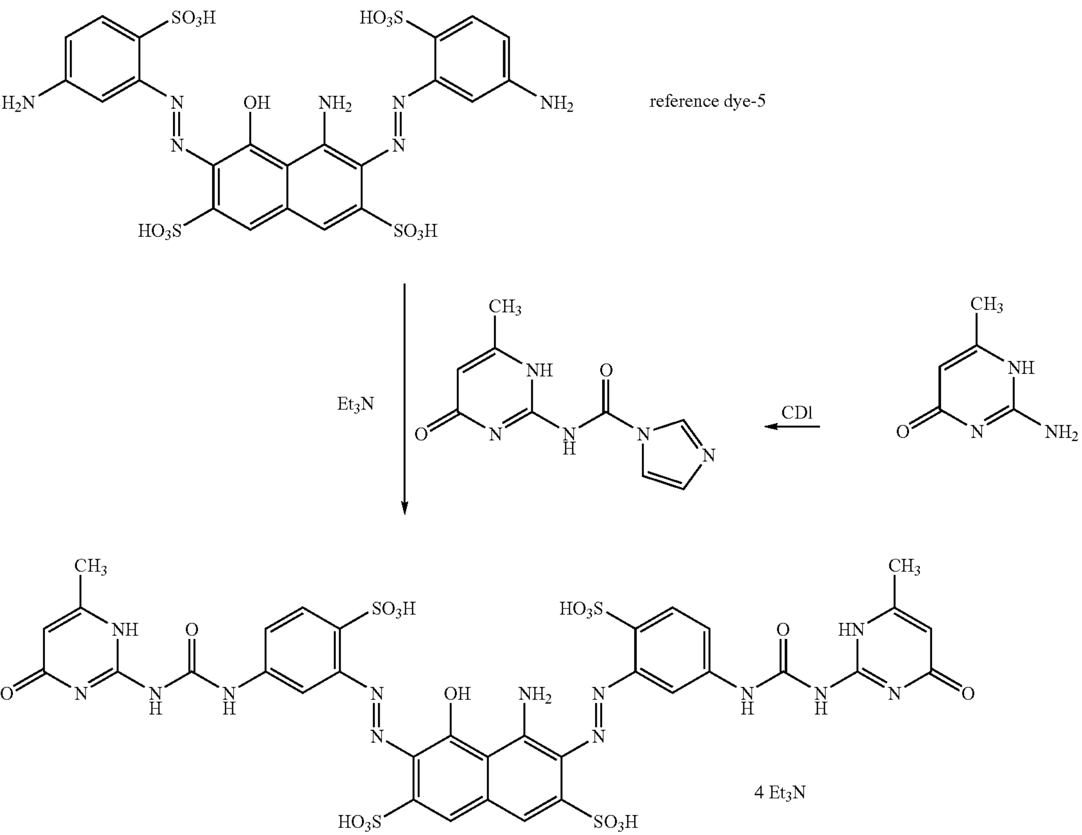

Dye-17

5.9 g (33 mmol) CDI was added to a suspension of 3.8 g (30 mmol) 2-amino-4-hydroxy-6-methylpyrimidine. The reaction is slightly exothermic and the mixture remains a suspension. The mixture is stirred for 30 minutes. 7.2 g of reference dye-5 is dissolved in 50 mL dimethylacetamide at 50° C. by adding 5.6 mL triethylamine. This solution is added to the suspension of CDI activated 2-amino-4-hydroxy-6-methylpyrimidine and the reaction is allowed to continue over night at room temperature. The precipitated mixture of products is isolated by filtration, washed with ethylacetate and dried. The compound was purified using preparative chromatography using a gradient elution from methanol/water 10/90 to methanol/water 90/10, both buffered with 1.05 mL triethylamine and 0.5 mL acetic acid per liter eluent, on a Kromasil C18 (100 A, 10 μm) silica. The chromatography was run on a Prochrom LC80 column at a speed of 150 mL per minute and a gradient elution time of 30 minutes. Dye-17 was isolated with 10% yield and characterized by 1H-NMR spectroscopy and mass spectroscopy.

Synthesis Example 21

This example discloses the synthesis of Dye-18

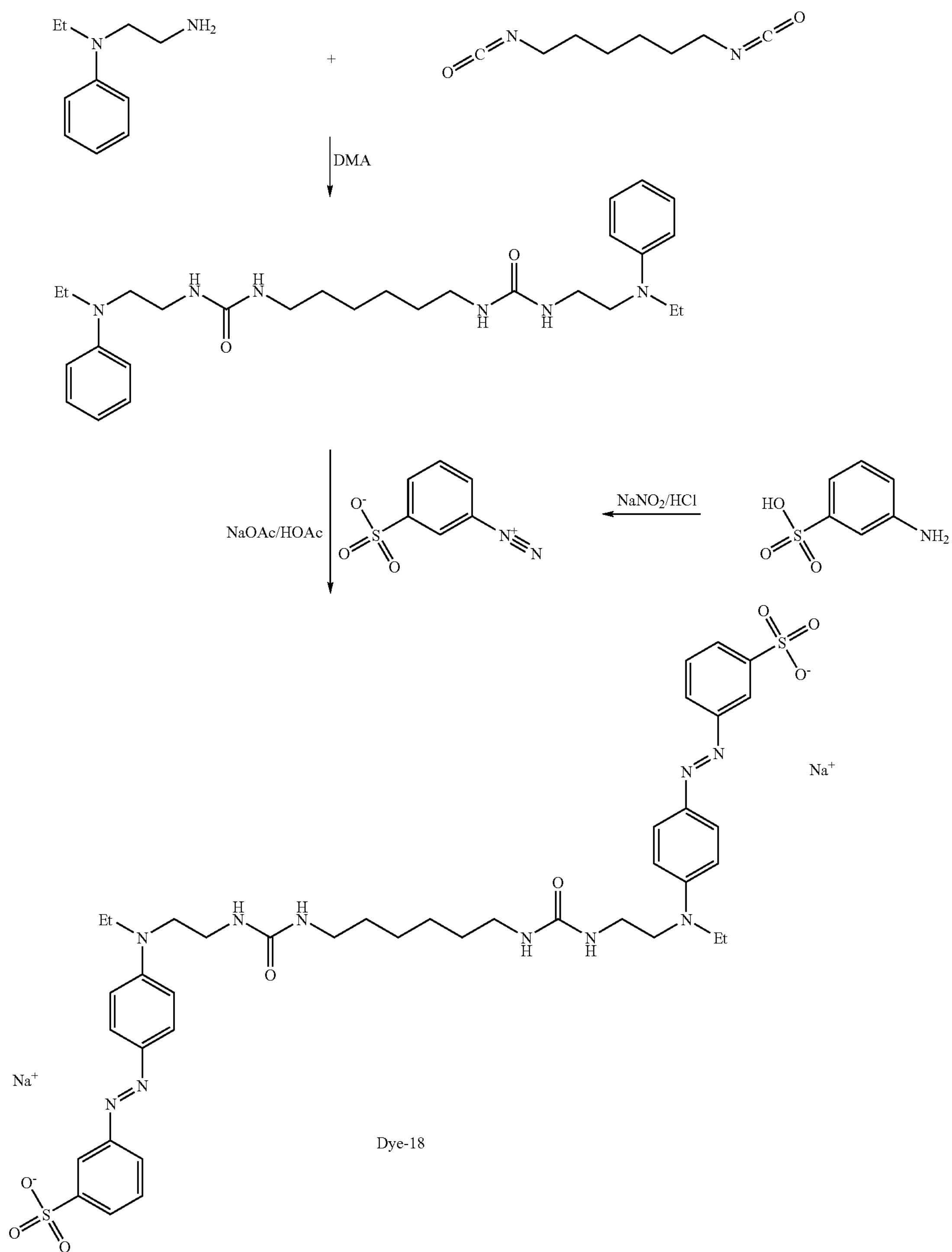

Preparation of the Bis-urea Intermediate 7.1 g (43 mmol) N-aminoethyl-N-ethyl-aniline was dissolved in 20 mL dimethylacetamide. A solution of 3.4 g (0.2 mmol) 1,6-diisocyanatohexane in 20 mL dimethylacetamide was added dropwise while keeping the reaction at 20° C. On standing over night, a small amount of the bis-urea intermediate precipitated from the reaction mixture. The precipitate was isolated by filtration, washed with acetone and dried. 0.8 g (8%) was isolated. The dimethylacetamide filtrate was poured into 250 mL ice/water. The precipitated product was isolated by filtration washed with 50 mL acetone and 50 mL ethyl acetate and dried. 6.9 g (70%) was isolated.

Diazotation of Metanilic Acid 1.7 g (10 mmol) metanilic acid was added to a solution of 2.7 mL concentrated hydrochloric acid in 15 mL water. The suspension was cooled to 3° C. A solution of 0.76 g (11 mmol) $NaNO_2$ in 2 mL of water was added while keeping the reaction mixture at 3° C. The diazonium salt precipitated from the reaction mixture as a zwitterion.

Preparation of Dye 18

6.9 g $NaOAc.3H_2O$ was dissolved in 7 mL water and 22 mL acetic acid. 2.5 g (5 mmol) of the bis-urea intermediate was dissolved in this mixture. The cooled suspension of diazotated metanilic acid was added portionwise to the solution of the bis-urea. The reaction was allowed to continue for one hour and the mixture was poured into 200 mL water. The acetic acid was neutralized with 50 mL of a 10% $NaHCO_3$-solution. The solution was extracted with 300 mL n.-butanol and a second time with 100 mL n.-butanol. The combined butanol-extracts were evaporated under reduced pressure and Dye-18 was isolated by preparative column chromatography (eluent: 0.2M NaCl/MeOH 35/65 on a Kromasil C18 (100 A, 10 μm)-silica). 2.8 g (64%) of Dye 18 was isolated as disodium salt. The structure was confirmed with $^1$H-NMR-spectroscopy.

Synthesis Example 22

This example discloses the synthesis of Dye-21 Synthesis of the diphthalimide.

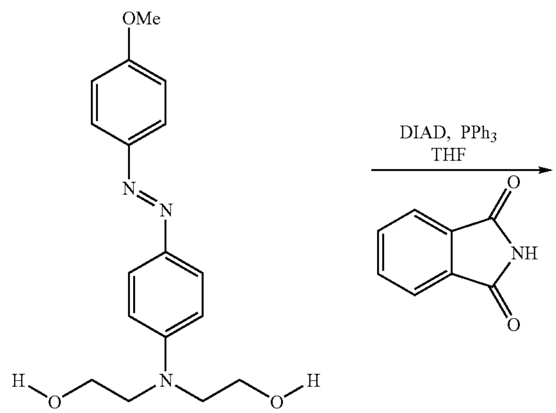

-continued

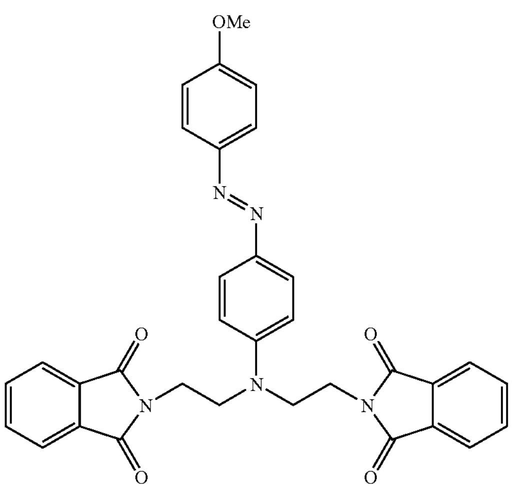

The azodye-diol (1 gram; 3.17 mmol (prepared according to standard procedures) was dissolved in 20 mL of THF together with phthalimide (1.4 gram; 9.5 mmol) and triphenylphosphine (2.4 gram; 9.1 mmol). Diisopropylazodicarboxylate (1.9 gram; 9.4 mmol) in THF was added dropwise to this solution while cooling the mixture in a water bath. Overnight stirring at room temperature yielded a precipitate. Ether was added, stirring was continued for some time and the precipitate was collected by filtration. Yield: 1.43 gram (78%). The diphthalimide was pure according to TLC and NMR analyses.

$^1$H NMR ($CDCl_3$), δ=7.9–7.6 (12H, m), 7.0 (4H, 2), 3.95 (4H, m), 3.9 (3H, s), 3.8 (4H, m).

Synthesis of Dye-21.

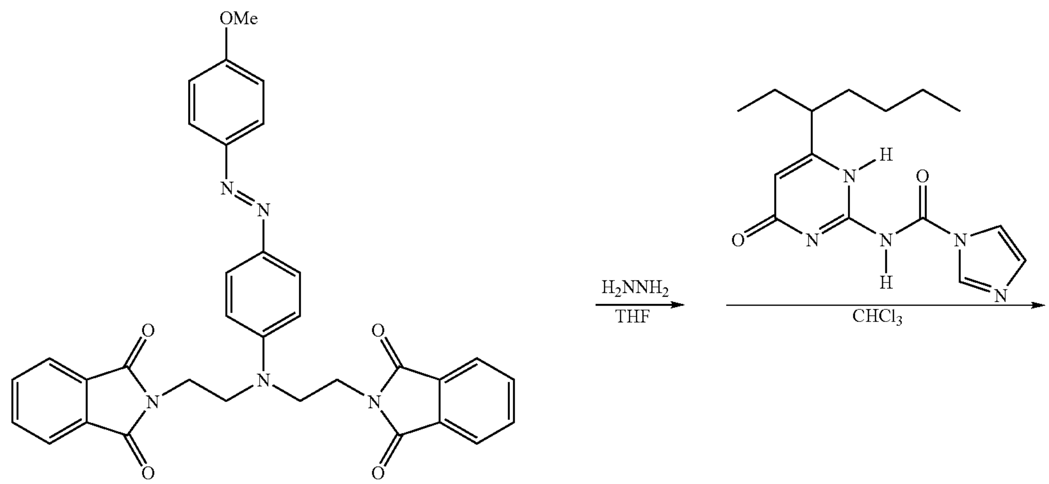

-continued

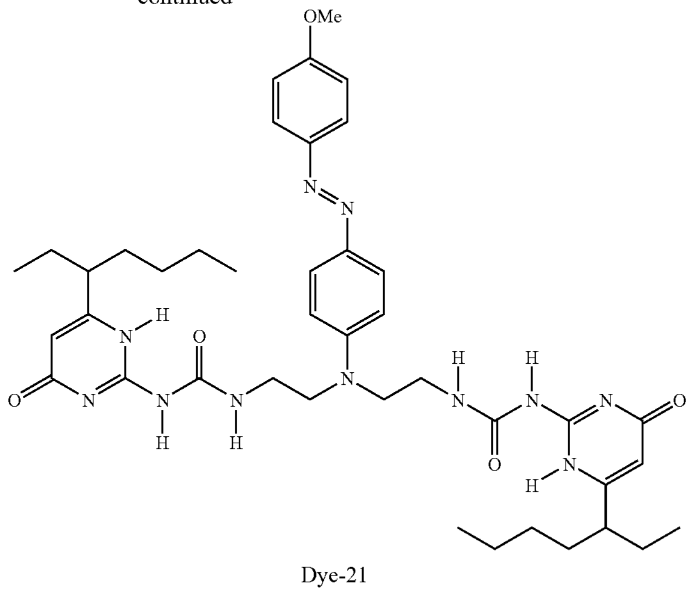

Dye-21

The diphthalimide (1.43 gram; 2.5 mmol) was suspended in 40 mL of boiling THF and hydrazine hydrate (2.6 mL). The suspension developed into a clear solution and subsequently a white precipitate was formed. After cooling down the mixture it was filtered and the filtrate was concentrated to yield the crude diamine that was used in the next step. The CDI-activated product of (1-ethylpentyl)-isocytosine (2.1 gram, 6.93 mmol) was stirred overnight at room temperature in 50 mL $CHCl_3$ together with the crude diamine (0.87 gram; 2.78 mmol). The mixture was subsequently washed with a HCl solution and a $NaHCO_3$ solution, and thereafter dried and concentrated. The product was precipitated from $CHCl_3$ into methanol and yielded 1.92 gram of Dye-21 as a yellow product (87%).

1H NMR ($CDCl_3$), δ=13.2 (2H, s), 11.9 (2H, s), 10.4 (2H, s), 7.8 (4H, m), 7.0 (4H, m), 5.8 (2H, s), 3.8 (3H, s), 3.7–3.4 (8H, m), 2.3 (2H, m), 1.8–1.5 (8H, m), 1.3 (8H, m), 0.95–0.8 (12H, m).

MALDI-TOF MS, [M+H+]=784.6, [M+Na+]=806.6, [M+K+]=822.6.

UV: λmax=408 nm; ϵ=14000 ($CHCl_3$).

Synthesis Example 23

This example discloses the synthesis of Dye-22

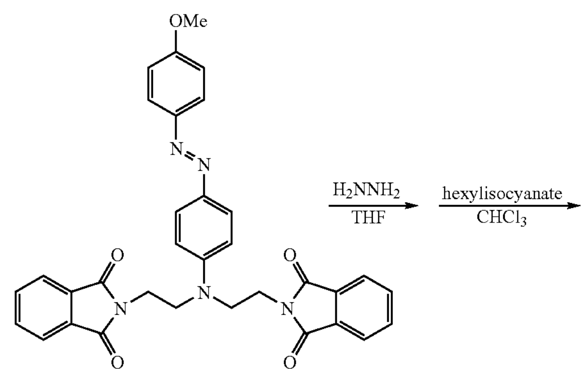

-continued

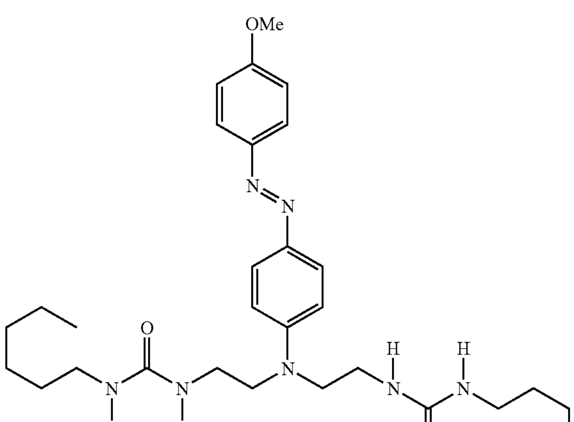

Dye-22

The diphthalimide (1.43 gram; 2.5 mmol) was suspended in 40 mL of boiling THF and hydrazine hydrate (2.6 mL). The suspension developed into a clear solution and subsequently a white precipitate was formed. After cooling down the mixture it was filtered and the filtrate was concentrated to yield the crude diamine that was used in the next step. Hexyl isocyanate (2.5 equivalents) was stirred overnight at room temperature together with the crude diamine in 50 mL $CHCl_3$. Dye-22 was purified by column chromatography (CHCl3/MeOH eluent), followed by precipitation in CHCl3/heptane.

$^1$H NMR ($CDCl_3$), δ=7.8 (4H, m), 7.0 (2H, d), 6.8 (2H, d), 5.8 (2H, bs), 5.2 (2H, bs), 3.9 (3H, s), 3.6–3.3 (8H, m), 3.1 (4H, m), 1.6–1.2 (16H, m), 0.95–0.8 (6H, t).

MALDI-TOF MS, $[M+H^+]$=568.6, $[M+Na^+]$=590.6, $[M+K^+]$=606.6.

UV: λmax=406 nm; ϵ=26000 ($CHCl_3$).

Synthesis Example 24

This example discloses the synthesis of Dye-23

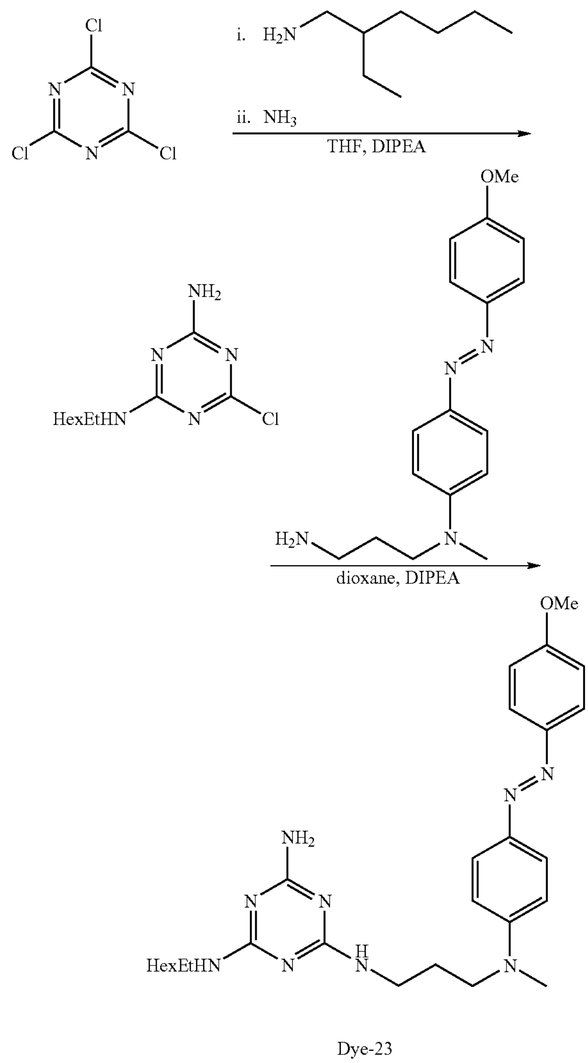

Dye-23

The modification of cyanuric chloride with ethylhexyl amine and ammonia has been described in Example 12. 4-(4-(N-methyl-N-(3-aminopropyl)amine)-phenylazo)-anisole (7.22 g, 24.2 mmol; prepared according to standard procedures), the triazine chloride (4.51 g, 17.5 mmol) and diisopropylamine (2.65 g, 20.5 mmol) are boiled overnight in 150 mL of dioxane. The compounds dissolved on heating and a suspension developed during stirring. After cooling, $CHCl_3$ was added and the mixture was consecutively washed with a HCl-solution and a $NaHCO_3$ solution. The organic solution was dried with $MgSO_4$, filtered and concentrated. The crude product was purified by silica column chromatography using $CHCl_3$ with 1% MeOH as eluent. 4.0 g of Dye-23 was obtained as a yellow powder.

$^1$H NMR ($CDCl_3$), δ=7.8 (4H, m), 7.0 (2H, m), 6.7 (2H, m), 5.3–4.8 (4H, bs), 3.9 (3H, s), 3.6–3.2 (6H, m), 3.0 (3H, s), 1.9 (2H, m), 1.5 (1H, m), 1.4–1.2 (8H, m), 0.9 (6H, m).

MALDI-TOF MS $C_{28}H_{41}N_9O$, [M+H$^+$]=520.3, [M+Na$^+$]=542.3.

UV: $\lambda_{max}$ ($CHCl_3$)=410 nm; $\epsilon$=23000

Synthesis Example 25

This example discloses the synthesis of Dye-24 and Dye-25

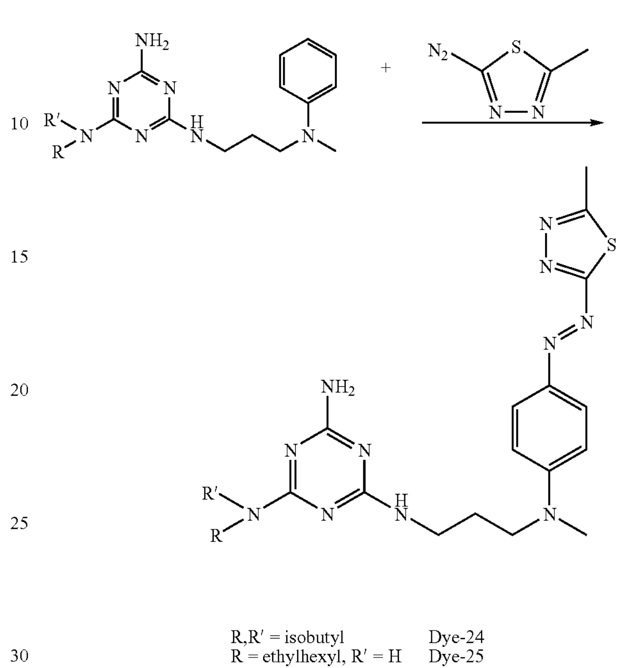

R,R′ = isobutyl Dye-24
R = ethylhexyl, R′ = H Dye-25

The syntheses of the triazine starting compounds are described in Example 12. The diazonium salt of 2-amino-5-methyl-1,3,4-thiadiazole was prepared by dropwise addition of a 40% $NO_2HSO_3$ solution in sulfuric acid (4.1 g) to an ice cooled solution of the thiadiazole (1.5 g) in acetic acid (18 mL) and sulfuric acid (2.4 mL), while maintaining the temperature of the reaction mixture below 10° C. Stirring was continued for an additional 30 minutes to obtain a clear solution.

Dye-24. The diazonium salt solution (2.5 equivalents) was added dropwise to a cooled solution (10–15° C.) of the triazine (2 g, 5.2 mmol) in cellusolve acetate (32 mL). Stirring was continued for two hours at room temperature. The mixture was poured onto ice to yield a sticky red product that was collected by filtration over paper. The product was dissolved in $CHCl_3$. The organic solution was washed with a $NaHCO_3$ solution, and dried with $MgSO_4$. After concentration, the product was purified by column chromatography using $CHCl_3$ with 1% MeOH as eluent. Precipitation from $CHCl_3$ into pentane yielded 0.9 g of Dye-24 as a red powder.

$^1$H NMR ($CDCl_3$), δ=7.8 (2H, d), 6.6 (2H, d), 5.5 (1H, bs), 5.1 (2H, bs), 3.5–3.2 (8H, m), 3.0 (3H, s), 2.7 (3H, s), 2.0 (2H, m), 1.8 (2H, m), 0.9 (12H, m).

MALDI-TOF MS $C_{24}H_{37}N_{11}S$, [M+H$^+$]=512.3, [M+Na$^+$]=534.3.

UV: λmax ($CHCl_3$)=486 nm; $\epsilon$=36000

Dye-25 was prepared in the same way to yield 3.9 g of a red powder.

$^1$H NMR ($CDCl_3$), δ=7.8 (2H, d), 6.6 (2H, d), 5.4–4.8 (4H, bm), 3.5–3.3 (4H, m), 3.2 (2H, m), 3.0 (3H, s), 2.7 (3H, s), 1.9 (2H, m), 1.4 (1H, m), 1.2 (8H, m), 0.9 (6H, m).

MALDI-TOF MS $C_{24}H_{37}N_{11}S$, [M+H$^+$]=512.3, [M+Na$^+$]=534.3.

UV: $\lambda_{max}$ ($CHCl_3$)=486 nm; $\epsilon$=38000.

Synthesis Example 26

This example discloses the synthesis of Dye-26

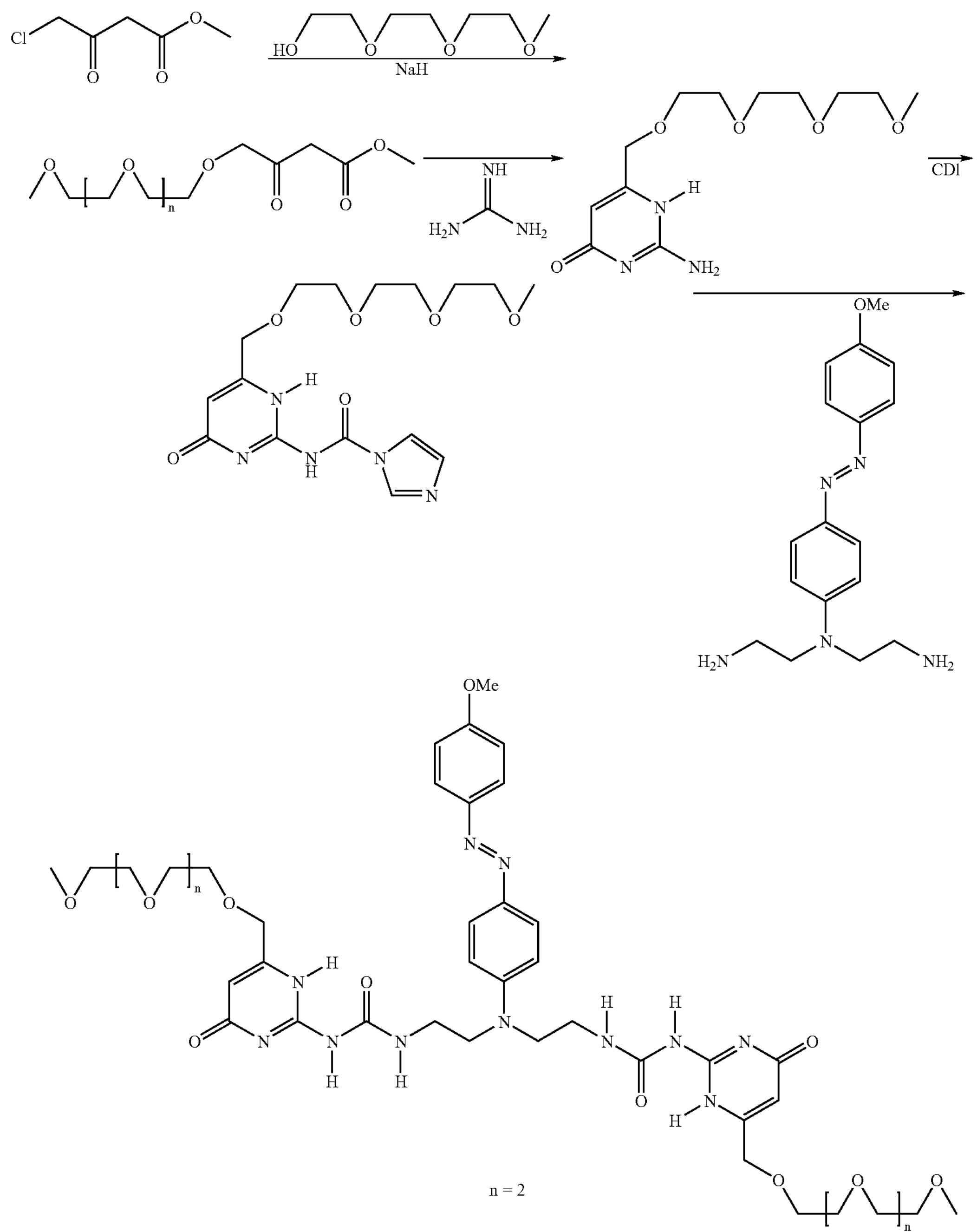

Dye-26

NaH (60%, 1.2 g, 30 mmol) was stirred in 20 mL dry THF under an argon atmosphere. Triethylene glycol (2 g, 12.2 mmol) in 5 mL THF was added dropwise, and after 30 minutes of stirring the β-keto ester (1.8 g, 12 mmol) in 6 mL THF was added dropwise. The mixture was stirred overnight at room temperature, and was thereafter poured into a 10% aqueous solution of acetic acid. Extraction with $CH_2Cl_2$, washing of the organic layer with water and a NaCl solution, drying with $MgSO_4$, filtration and concentration gave the crude β-keto ester oil (2.1 g, 63%) that was used in the next step as isolated. The β-keto ester (2 g, 7.2 mmol) and guanidine carbonate (1.7 g, 18.9 mmol) were boiled in 40 mL of ethanol for 72 hours. The mixture was concentrated, isopropanol was added and the suspension was filtered to remove the excess of guanidine carbonate. The filtrate was concentrated and eluted over a silica column, first using $CHCl_3$ with 4% MeOH to remove contaminations. The isocytosine, a white solid, could be collected by eluting with $CHCl_3$/MeOH (4%) containing 1% triethylamine. Yield: 1.65 g (80%).

The isocytosine (1.65 g, 5.7 mmol) was stripped from possible protic solvents by co-evaporation with toluene and was dissolved in 40 mL of $CHCl_3$ that had been pre-dried over molecular sieves. Carbonyl di-imidazole, CDI, (1.7 g, 10.5 mmol) was added and the solution was stirred for 8 hours at room temperature; NMR analysis showed that no isocytosine was present anymore. The solution was washed twice with a saturated NaCl solution, dried with $MgSO_4$, and concentrated to give a white product. Yield of the activated product: 1.9 g (90%). The activated isocytosine (1.16 g, 3.0 mmol) was stirred for three days at room temperature with 4-(4-(N,N-bis-(2-amino ethyl)amine)-phenylazo)-anisole (0.45 g, 1.44 mmol) in 25 mL of $CHCl_3$ under an atmosphere of argon. The mixture was washed with an 1M HCl solution and with a $NaHCO_3$ solution. The organic layer was dried with $Na_2SO_4$ and concentrated to give a yellow solid.

$^1H$ NMR ($CD_3SOCD_3$), δ=11.0–10.0 (6H, bs), 7.7 (4H, m), 7.0 (4H, m), 5.8 (2H, s), 4.2 (4H, s), 3.8 (4H, s), 3.6–3.3 (31H, m), 3.2 (6H, s).

MALDI-TOF MS $C_{43}H_{61}N_{11}O_{13}$, $[M+H^+]$=940.3, $[M+Na^+]$=962.3, $[M+K^+]$=978.3, $[M+2Na^+-H^{30}]$=984.3, $[M+K^++Na^+-H^+]$=1000.3.

UV: $\lambda_{max}$ ($CHCl_3$)=404 nm; ε=28000.

NMR-data on the intermediate products are in agreement with the assigned molecular structures.

Synthesis Example 27

This example discloses the synthesis of Dye-27 and Dye-28

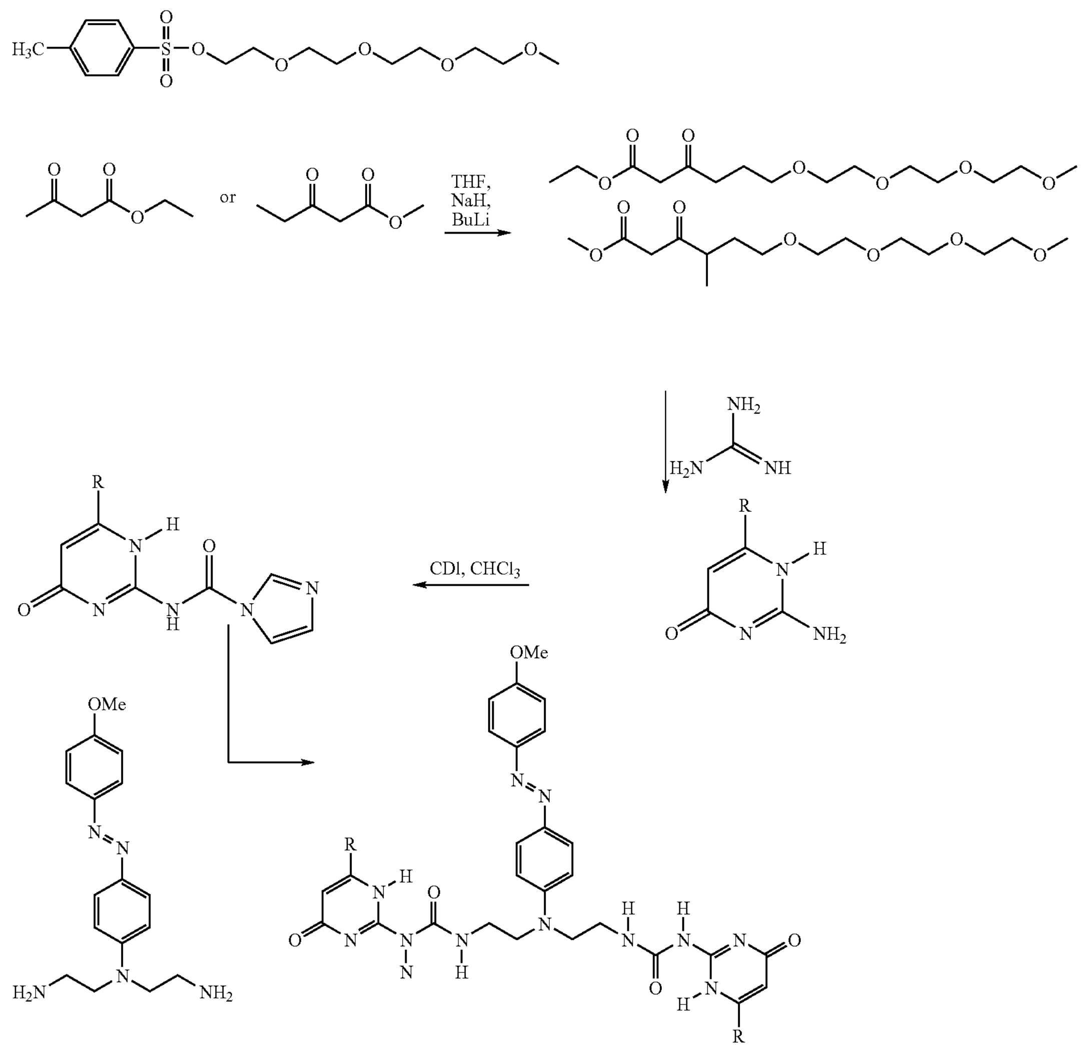

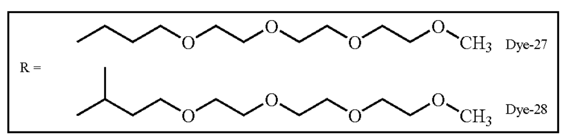

Monomethyl tetraethylene glycol (25.8 g, 124 mmol) was stirred in 35 mL of THF, 35 mL of water and NaOH (7.1 g, 178 mmol). The mixture was kept under 5° C., while TsCl (21.5 g, 113 mmol) in 35 mL of THF was added dropwise; stirring was continued for an additional 4 hours. $CHCl_3$ was added to the solution, and the mixture was washed twice with a saturated NaCl solution. Drying with $MgSO_4$, filtration and concentration gave 37.2 grams of an oily tosylate (91%).

Dye-27. Ethylacetoacetate (2.0 g, 15.4 mmol) was added dropwise to an ice-cooled suspension of NaH (60%, 0.73 g, 18.3 mmol) in 45 mL of dry THF. After one hour of stirring, n-BuLi in hexanes (1.6 M, 9.5 mL, 15.2 mmol) was added, while maintaining ice-cooling of the reaction mixture. After another hour, the monomethyl tetraethylene glycol tosylate (5 g, 13.8 mmol) in 15 mL of dry THF was added dropwise to the ethylacetoacetate mixture and the suspension was put to reflux for 16 hours. The reaction mixture was poured into water and extracted with $CH_2Cl_2$. The organic layer was washed with a saturated NaCl solution, and dried with $Na_2SO_4$. Silica column chromatography using 5% dimethoxyethane in $CHCl_3$ gave 3.2 g β-keto ester product (72%).

The β-keto ester (1.9 g, 5.9 mmol) and guanidine carbonate (1.35 g, 15 mmol) were boiled in 30 mL of ethanol for 16 hours. The mixture was concentrated and eluted over a silica column, first using $CHCl_3$ with 4% MeOH to remove contaminations. The isocytosine, a white solid, was collected by eluting with $CHCl_3$/MeOH (4%) containing 2% triethylamine. Yield: 0.82 g (44%).

The isocytosine (0.82 g, 2.6 mmol) was co-evaporated with toluene and stirred for 6 hours with CDI (0.55 g, 3.4 mmol) in 20 mL of dry $CHCl_3$ under an argon atmosphere. The mixture was washed twice with a saturated NaCl solution, dried with $Na_2SO_4$ and concentrated.

The activated product (0.8 g, 1.95 mmol) was stirred with 4-(4-(N,N-bis-(2-amino ethyl)amine)-phenylazo)-anisole (0.26 g, 0.83 mmol) in 25 mL of $CHCl_3$. After 24 hours, the solution was washed with a 1M HCl and thereafter with a $NaHCO_3$ solution. Drying with $Na_2SO_4$ was followed by filtration and concentration to yield Dye-27 as a yellow solid. The solid was dissolved in $CHCl_3$ and precipitated into pentane. Yield: 0.77 g (95%).

$^1$H NMR ($CDCl_3$), δ=13.0 (2H, bs), 11.9 (2H, bs), 10.4 (2H, bs), 7.8 (4H, m), 6.9 (4H, m), 5.9 (2H, s), 3.9–3.3 (45H, m), 2.6 (4H, t), 1.9 (4H, t).

MALDI-TOF MS $C_{47}H_{69}N_{11}O_{13}$, $[M+H^+]$=996.5, $[M+Na^+]$=1018.5.

UV: $\lambda_{max}$ ($CHCl_3$)=404 nm; λ=15000

NMR-data on the intermediate products are in agreement with the assigned molecular structures.

Dye-28. THF (25 mL) was added to NaH (60%, 0.64 g, 16 mmol) which was previously washed with pentane. Methylpropionylacetate (1.5 g, 11.5 mmol) was added, while the suspension was cooled in an ice bath. After 10 minutes of stirring, n-BuLi in hexanes (2.5 M, 4.8 mL, 12 mmol) was added dropwise. Another 10 minutes of stirring was followed by addition of the monomethyl tetraethyleneglycol tosylate (4.6 g, 12.7 mmol) in 15 mL of THF. The mixture was boiled overnight, and then washed with a 1M HCl solution and a saturated NaCl solution. The β-keto ester was purified by silica column chromatography using consecutively $CHCl_3$/MeOH (2%), and $CHCl_3$/MeOH (4%) containing 2% triethylamine as eluents.

The β-keto ester (1.6 g, 5.0 mmol) and guanidine carbonate (1.15 g, 12.8 mmol) were boiled in 20 mL of ethanol for 16 hours. The mixture was concentrated and eluted over a silica column, first using $CHCl_3$ with 4% MeOH to remove contaminations. The isocytosine was collected as a white solid by eluting with $CHCl_3$/MeOH (4%) containing 2% triethylamine. Yield: 1.36 g (83%).

The isocytosine (1.36 g, 4.1 mmol) was stripped from protic contaminants by co-evaporation with toluene and was dissolved in 25 mL of dry $CHCl_3$. CDI (1.05 g, 6.5 mmol) was added and stirring was maintained overnight under an argon atmosphere. The mixture was washed twice with a saturated NaCl solution, dried with $Na_2SO_4$ and concentrated.

The activated product (1.9 g, 4.5 mmol) was stirred with 4-(4-(N,N-bis-(2-amino ethyl)amine)-phenylazo)-anisole (0.55 g, 1.76 mmol) in 50 mL of dry $CHCl_3$. After 24 hours, the solution was washed with a 1M HCl solution and thereafter with a $NaHCO_3$ solution. Drying with $Na_2SO_4$ was followed by filtration and concentration to give Dye-28 as a yellow solid. The solid was dissolved in $CHCl_3$ and precipitated into pentane, followed by crystallization from ethylacetate. Yield: 1.55 (87%).

$^1$H NMR ($CDCl_3$), δ=13.1 (2H, bs), 11.9 (2H, bs), 10.4 (2H, bs), 7.8 (4H, m), 6.9 (4H, m), 5.9 (2H, s), 3.9–3.3 (45H, m), 2.9 (2H, m), 1.9 (4H, t), 1.3 (6H, d).

MALDI-TOF MS $C_{49}H_{73}N_{11}O_{13}$, $[M+H^+]$=1024.5, $[M+Na^+]$=1046.5.

UV: $\lambda_{max}$ ($CHCl_3$)=404 nm; ϵ ($CHCl_3$)=16000

NMR-data on the intermediate products are in agreement with the assigned molecular structures.

Synthesis Example 28

This example discloses the synthesis of Dye-29

$MgCl_2$ (16.5 g, 173 mmol) was added to a cooled (−15° C.) mixture of potassium malonate (24.4 g, 144 mmol) and triethylamine (22.5 g, 223 mmol) in 200 mL acetonitrile. After stirring for 2 hours at 10–15° C., ethylhexanoyl chloride (11.2 g, 69 mmol) was added, while maintaining cooling in an ice bath. Overnight stirring at room temperature under an argon atmosphere was followed by evaporation of the solvent, addition of ether and an HCl solution. The organic layer was washed with a bicarbonate solution, dried over $MgSO_4$ and concentrated to give an almost quantitative yield of an oil. This β-keto ethyl ester (6.0 g, 28.0 mmol) was added dropwise to an ice cooled suspension of NaH (60%, 1.32 g, 33 mmol) in 75 mL of dried THF.

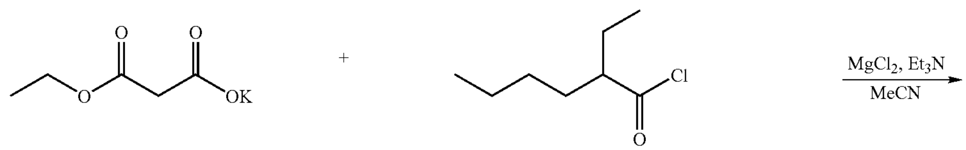

-continued

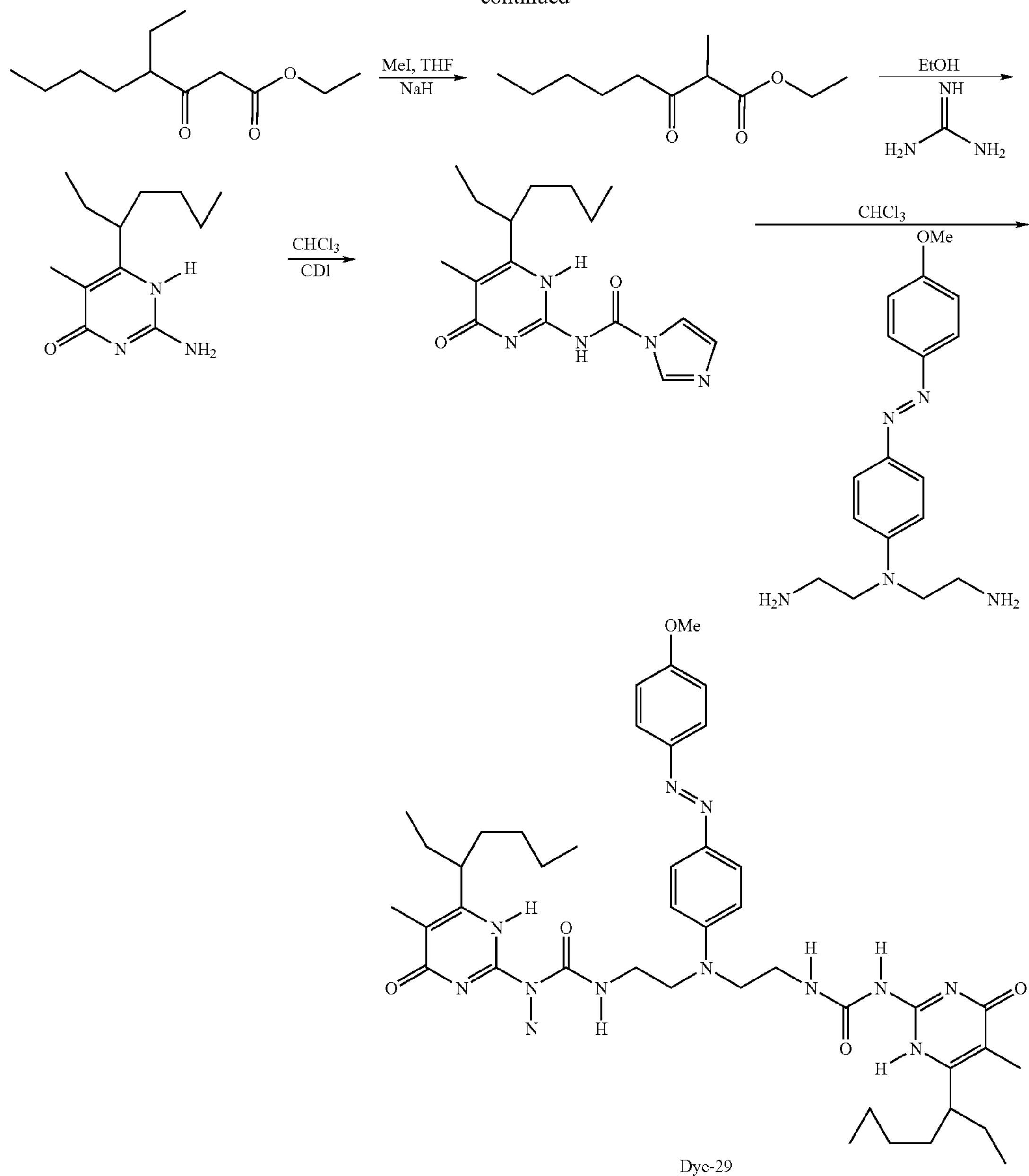

After an hour of stirring, MeI (2.4 mL, 38.5 mmol) was added and the mixture was stirred overnight under an argon atmosphere at 45° C. The product was poured into an aqueous 1M HCl solution and extracted with chloroform. The organic layer was washed with a saturated NaCl solution and dried with $Na_2SO_4$. Evaporation of the solvent gave 6.5 grams of an oil. This modified β-keto ethyl ester (11.2 g, 49.1 mmol) and guanidine carbonate (42.2 g, 469 mmol) were put to reflux in 275 mL of ethanol. Reflux was maintained during two days, using a Dean-Stark setup with dried molecular sieves in the receiving arm. Ethanol was removed by evaporation, chloroform was added and the organic solution was washed with a bicarbonate solution. Drying of the solution with $MgSO_4$ was followed by precipitation of the isocytosine into pentane to afford 6.0 grams (55%) of a white solid. The isocytosine (3.0 g, 13.5 mmol) and CDI (3.0 g, 18.5 mmol) were stirred during two hours in 75 mL of chloroform at room temperature. The mixture was washed three times with a saturated NaCl solution and then dried with $Na_2SO_4$. The activated product (3.9 g, 90%) was ready for use in the next step as NMR-analysis did not show any imidazole or CDI traces. The activated isocytosine (3.9 g, 12.3 mmol) was stirred overnight with 4-(4-(N,N-bis-(2-amino ethyl)amine)-phenylazo)-anisole (1.47 g, 4.7 mmol) in 120 mL of chloroform. The mixture was consecutively extracted with a 1 M aqueous HCl solution and a bicarbonate solution, followed by drying over $Na_2SO_4$. Evaporation of the solvent was followed by precipitation from chloroform into methanol, and then from chloroform into pentane to yield 1.5 grams of Dye-29 as a yellow solid.

$^1$H NMR ($CDCl_3$), δ=13.0 (2H, bs), 11.9 (2H, bs), 10.5 (2H, bs), 7.8 (4H, m), 7.0 (2H, m), 6.9 (2H, m), 3.8 (3H, s), 3.7 (4H, m), 3.5 (4H, m), 2.8 (2H, m), 2.1 (6H, s), 1.8–1.5 (8H, m), 1.4–1.2 (8H, m), 0.9 (12H, m).

MALDI-TOF MS $C_{43}H_{61}N_{11}O_5$, [M+H$^+$]=812.1, [M+Na$^+$]=834.1.

UV: $\lambda_{max}$ ($CHCl_3$)=410 nm; $\epsilon$ ($CHCl_3$)=22000

NMR-data on the intermediate products are in agreement with the assigned molecular structures.

Synthesis Example 29

This example discloses the synthesis of Dye-30

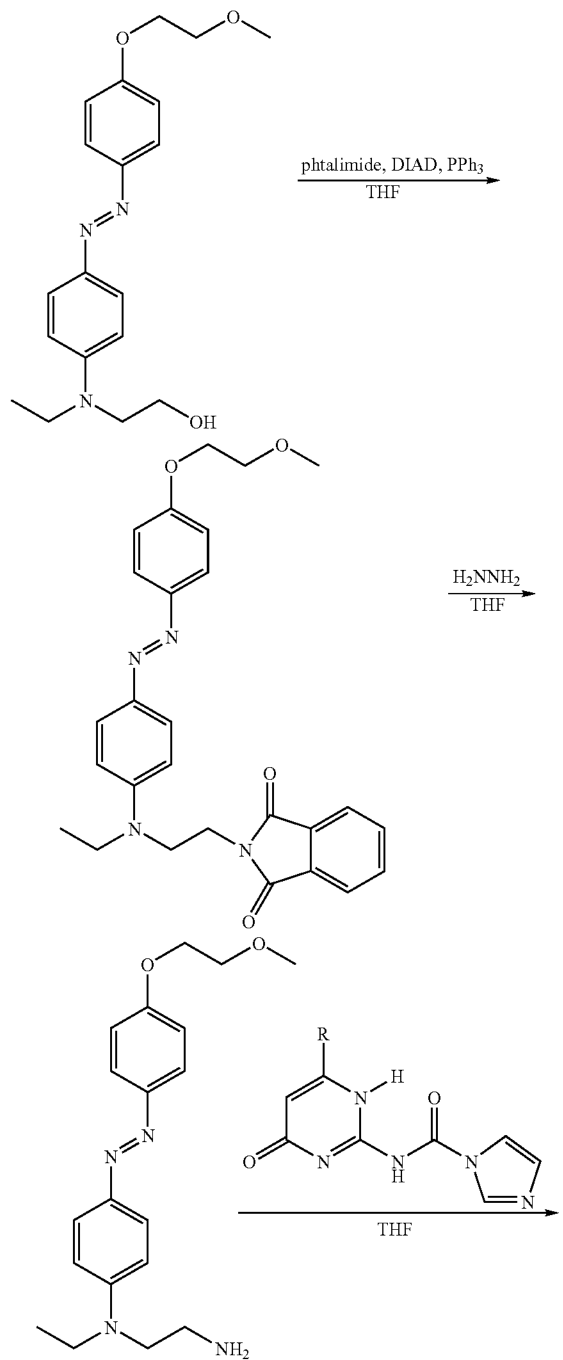

-continued

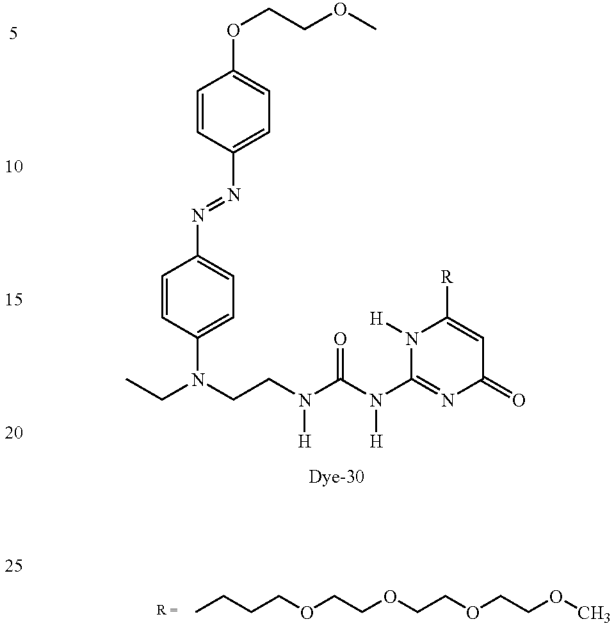

Dye-30

The CDI-activated glycolated isocytosine has been described in Example 11.

The dye alcohol (10 g, 29.2 mmol; prepared according to standard procedures), phthalimide (5.1 g, 34.7 mmol) and triphenylphosphine (9.2 g, 35.1 mmol) were dissolved in 200 mL THF. DIAD (7.1 g, 35.1 mmol) was added dropwise at room temperature. After overnight reaction, the product was concentrated and purified on a silica column ($CHCl_3$/MeOH, 1%). Stirring in ether/THF 20/1 gave a precipitate that was filtered and dried. Yield: 11.9 g (86%). Hydrazine hydrate (2 g, 40 mmol) was added to the phthalimide dye (11.9 g, 25.2 mmol) in boiling THF. After overnight reflux the white precipitate was removed by filtration. The filtrate was stirred overnight at 40° C. after an additional portion of hydrazine hydrate (1.5 g, 30 mmol) was added. Filtration and co-evaporation of the filtrate with toluene gave the amine product. This amine (1.35 g, 3.9 mmol) and the activated isocytosine (2.2 g, 5.4 mmol) were stirred overnight at room temperature in 20 mL of THF. The solution was concentrated, $CHCl_3$ was added and the organic solution was washed consecutively with 0.01 M HCl, salt and bicarbonate solutions. After drying on $MgSO_4$ the residue was purified by column chromatography on silica using $CHCl_3$/MeOH 1% to 4% as eluent. 1.54 g of Dye-30 was obtained (57%).

$^1$H NMR ($CDCl_3$), δ=13.0 (1H, bs), 11.9 (1H, bs), 10.4 (1H, bs), 7.8 (4H, m), 7.0 (2H, m), 6.8 (2H, m), 5.8 (1H, s), 4.2 (2H, t), 3.8 (2H, m), 3.7–3.4 (26H, m), 2.7 (2H, t), 2.0 (2H, m), 1.3 (3H, t).

MALDI-TOF MS $C_{34}H_{49}N_7O_8$, [M+H$^+$]=684.1, [M+Na$^+$]=706.1.

UV: $\lambda_{max}$ ($CHCl_3$)=413 nm; $\epsilon$=17000

NMR-data on the intermediate products are in agreement with the assigned molecular structures.

Synthesis Example 30

This example discloses the synthesis of Dye-31

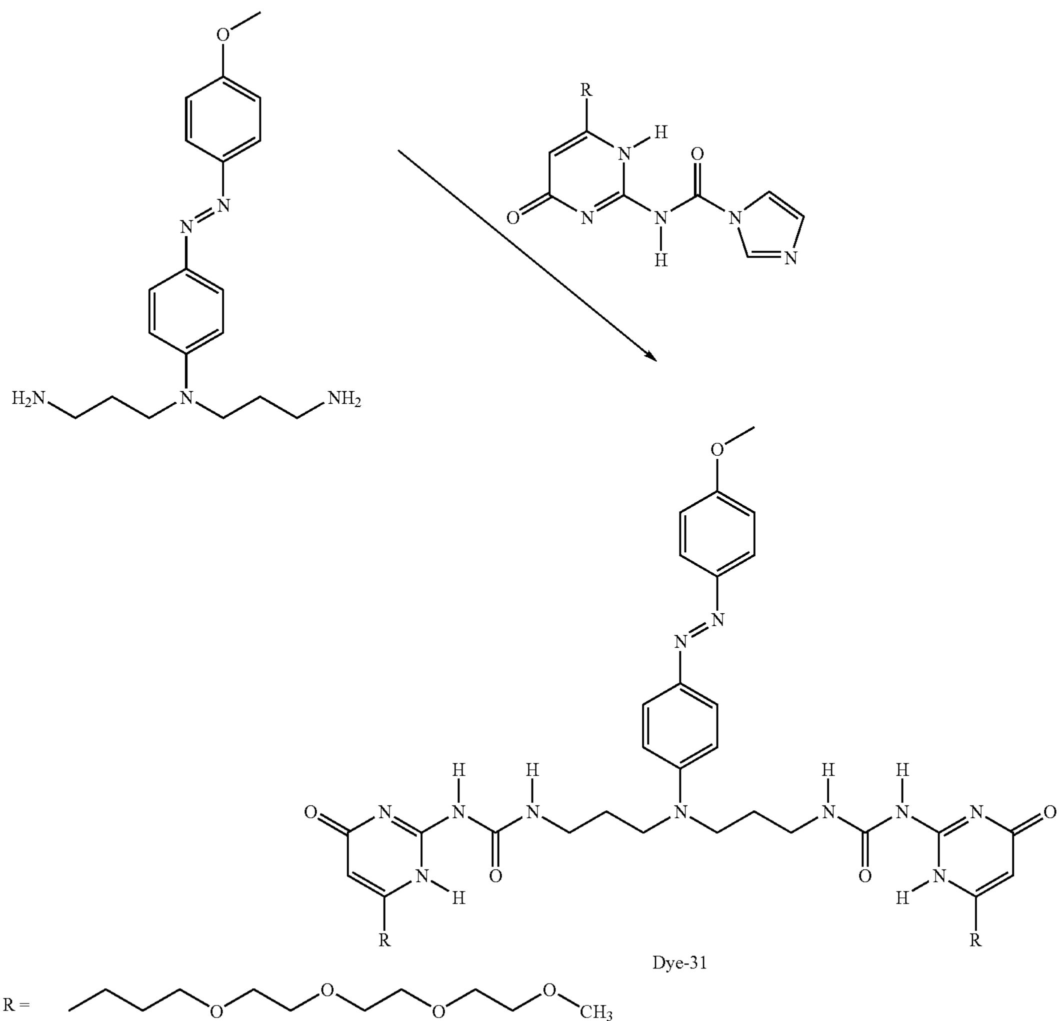

The CDI-activated glycolated isocytosine has been described in Example 11. The diamine (0.7 g, 2.1 mmol) and the CDI-activated isocytosine (2.0 g, 4.9 mmol) were stirred overnight in 20 mL of THF at room temperature under an argon atmosphere. Chloroform was added and the mixture was washed with a 0.01 M HCl solution and a saturated bicarbonate solution. The organic phase is dried over $Na_2SO_4$, filtered and concentrated under reduced pressure. The residue is purified by column chromatography over silica using $CHCl_3$/MeOH (2%) as eluent to yield 0.95 g of pure Dye-31.

$^1$H NMR ($CDCl_3$), δ=13.2 (1H, s), 13.0 (1H, s), 11.9 (1H, s), 11.7 (1H, s), 10.2 (1H, s), 10.0 (1H, s), 7.8 (4H, m), 7.0 (2H, m), 6.8 (2H, m), 5.8 (1H, s), 5.7 (1H, s), 3.9 (6H, s), 4.0–3.3 (39H, m), 3.1 (2H, m), 2.5 (4H, m), 2.1 (2H, m), 1.8 (4H, m).

MALDI-TOF MS $C_{49}H_{73}N_{11}O_{13}$, $[M+H^+]$=1024.4, $[M+Na^+]$=1046.4.

UV: $\lambda_{max}$ ($CHCl_3$)=418 nm; ε=24000

Synthesis Example 31

This example discloses the synthesis of Reference Dye-6

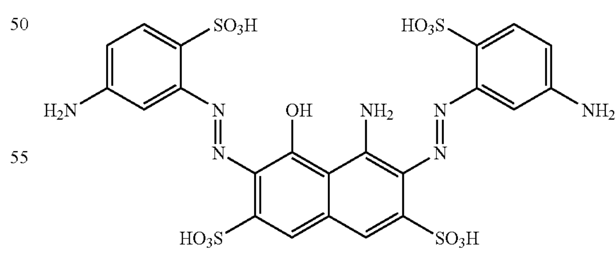

reference dye-5

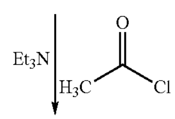

-continued

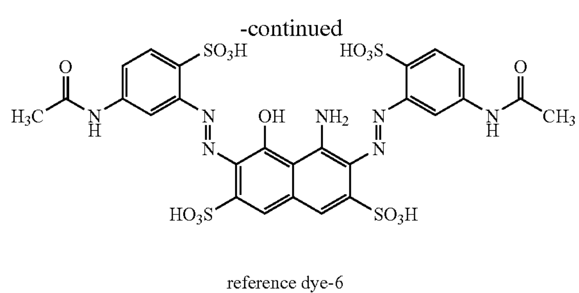

reference dye-6

0.9 g (11 mmol) acetyl chloride in 5 mL dimethylacetamide was added dropwise at 35° C. to a suspension of 3.6 g (5 mmol) of reference dye-5 and 2.8 mL (20 mmol) triethylamine in 50 mL dimethylacetamide. The reaction is slightly exothermic but remains a suspension. The reaction is allowed to continue over night at room temperature. The precipitated compound is isolated by filtration and washed with ethyl acetate. Reference dye-6 is re-suspended in 25-mL ethyl acetate, isolated by filtration and dried. From the combined filtrates, a second crop precipitates and is isolated by filtration and washed with methylene chloride. The two fractions were combined yielding 4.2 g of reference dye-6 (70%). Reference dye-6 was characterized by $^{1}$H-NMR spectroscopy and mass spectroscopy.

INK-JET EXAMPLES

In the Ink-jet Examples below the characteristics of dyes according to formula (I) are investigated.

Ink-jet Example 1

In this example a comparison is made between the light-fastness characteristics of some invention dyes and some reference dyes. The following compounds were involved:

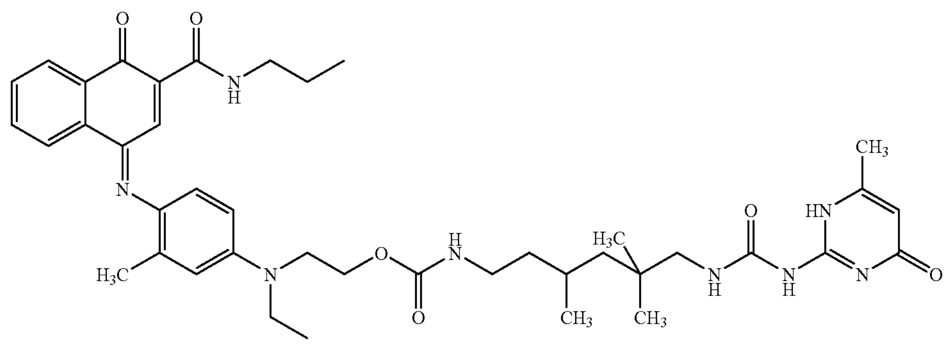

invention dye-8

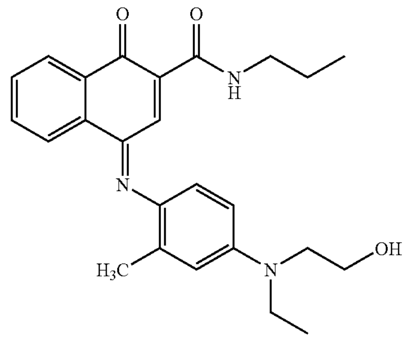

reference dye-1

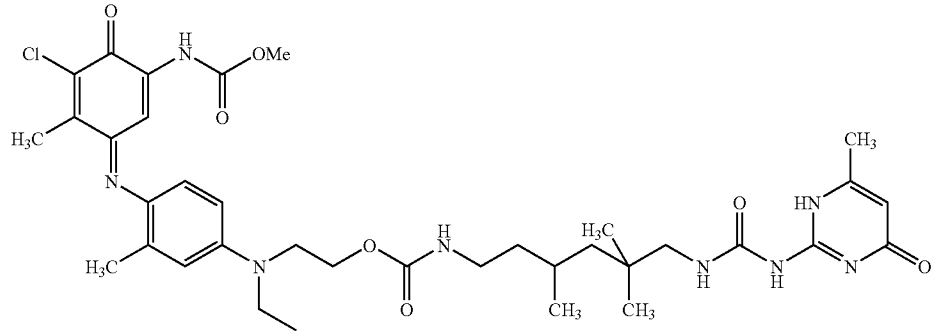

invention dye-6

-continued
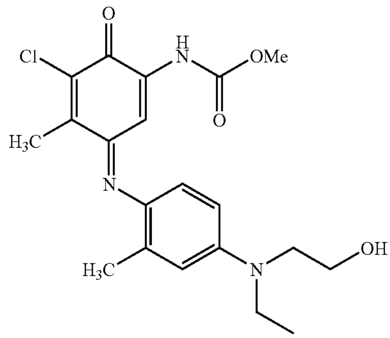
reference dye-2
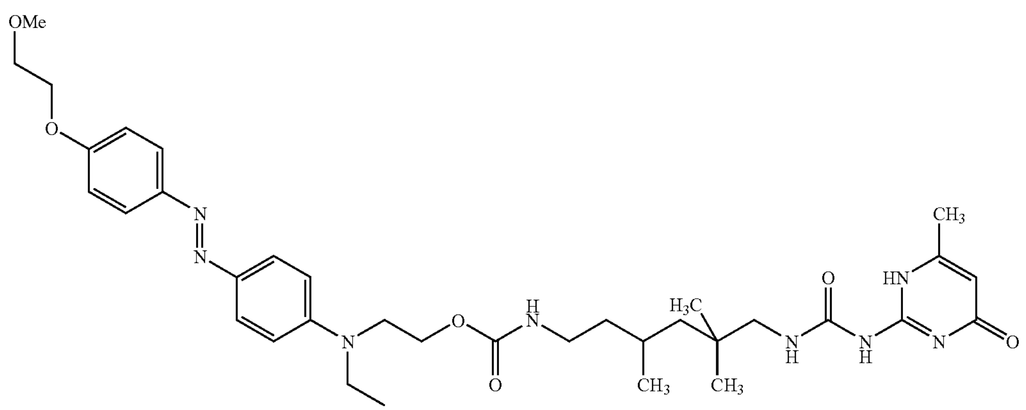
invention dye-9
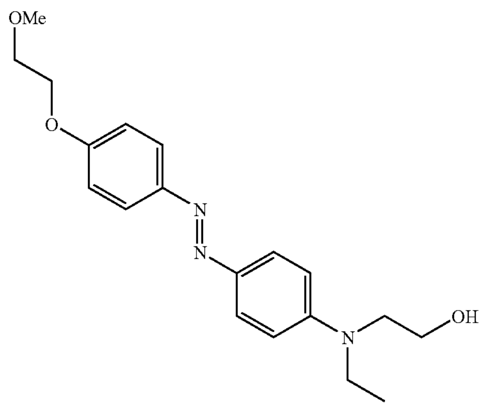
reference dye-3
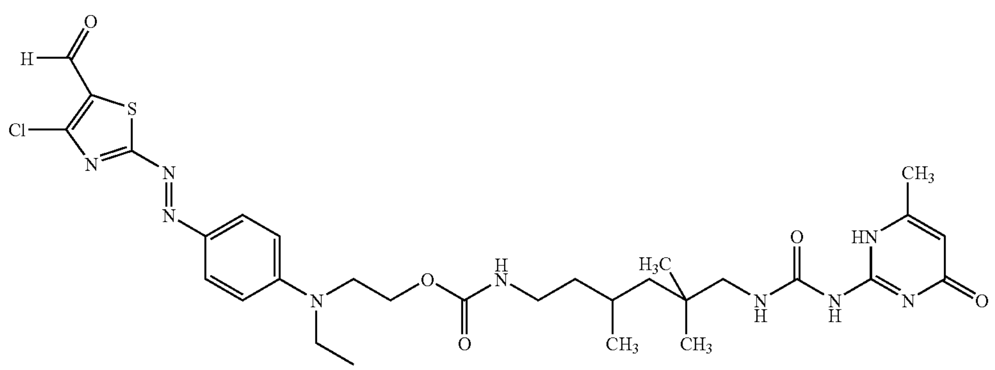
invention dye-7

-continued

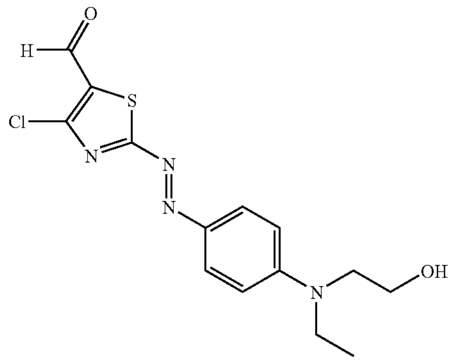

reference dye-4

Both reference and invention dyes were dissolved in 2-butanone as a 0.015 molar solution. Samples of 5 mL of the dye solutions were diluted with 5 mL methanol. From each sample, 20 µl of each solution was spotted on a Polar DTR receiver (trademark from AGFA) using an Anachem SK233 apparatus. Each sample was spotted 5 times and the average density value was taken as initial density for each dye at the start of the light-fastness test. The spotted samples were exposed during 8 hours using a Xenon-apparatus (Xenotest 150, equipped with a 7IR-filter, working in indoor mode). After one, two, four and eight hours, the density was measured again and the average density of the five spots was taken as the residual density. The percentage residual density is expressed as (residual density/initial density)×100. The results are summarized in Table 2.

TABLE 2

| Dye | 1 h exposure % residual density | 2 h exposure % residual density | 4 h exposure % residual density | 8 h exposure % residual density |
|---|---|---|---|---|
| Invention dye-8 | 86 | 78 | 73 | 42 |
| Reference dye-1 | 75 | 60 | 36 | 21 |
| Invention dye-6 | 92 | 89 | 80 | 61 |

TABLE 2-continued

| Dye | 1 h exposure % residual density | 2 h exposure % residual density | 4 h exposure % residual density | 8 h exposure % residual density |
|---|---|---|---|---|
| Reference dye-2 | 90 | 71 | 58 | 34 |
| Invention dye-9 | 98.5 | 97 | 77 | 63 |
| Reference dye-3 | 94 | 81 | 58 | 39 |
| Invention dye-7 | 99 | 87 | 77 | 56 |
| Reference dye-4 | 89 | 73 | 58 | 33 |

The results shown in Table 2 clearly show that use of the self-assembling dyes in ink compositions according to the present invention, results in significantly higher light-fastness of ink-jet images.

Ink-jet Example 2

In this example a comparison is made between the light-fastness characteristics of some invention dyes and some reference dyes. The following compounds were involved:

reference dye-7

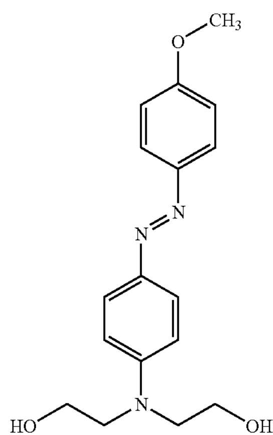

reference dye-8

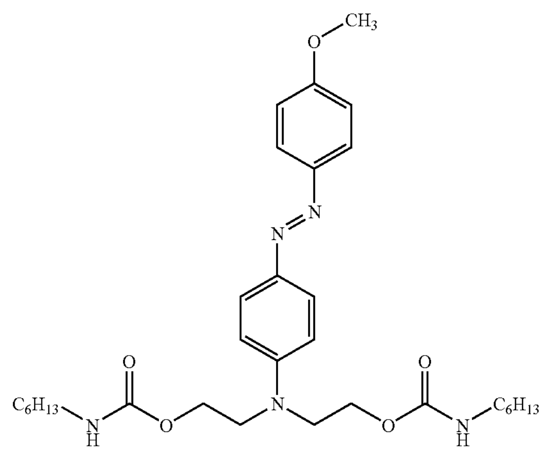

-continued

Dye 16

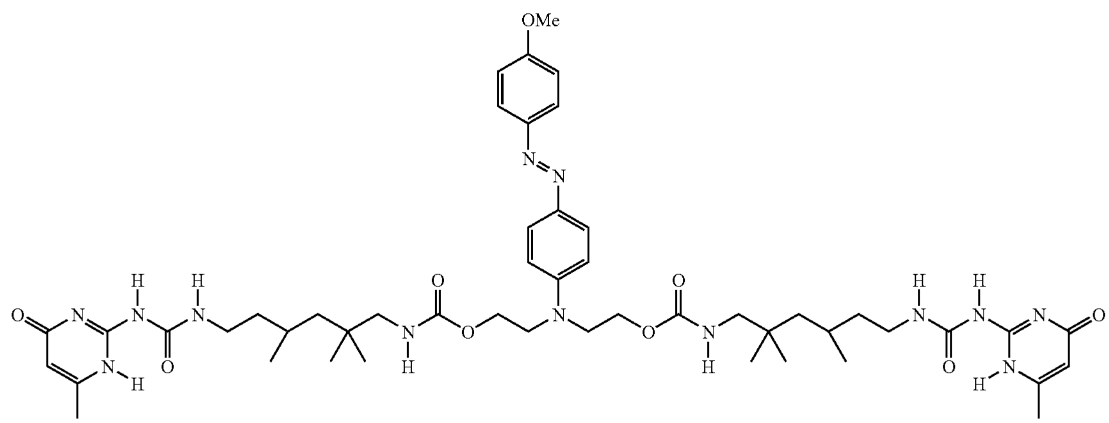

Both reference compounds and the invention dye were dissolved in $CH_2Cl_2$/2-methoxypropanol (1/1). Reference dye-7 was dissolved as a 0.25% solution (w/v). The reference dye-8 and the invention dye-16 were dissolved as a 0.5% solution (w/v). 1 mL of the samples was diluted with 0.75 mL 2-methoxypropanol and 0.75 mL $CH_2Cl_2$. A second sample of 1 mL was diluted with 1.75 mL 2-methoxypropanol and 2 mL $CH_2Cl_2$. For each sample 10 μl was spotted on a Polar DTR receiver (trademark from AGFA). Each sample was spotted 5 times and the average value was taken as the initial density for each dye at the start of the light-fastness test. The spotted samples were exposed during 8 hours using a Xenon-apparatus (Xenotest 150, equipped with a 7IR-filter, working in indoor mode). After one, two, four and eight hours, the density was measured again and the average density of five spots was taken as the residual density. The percentage residual density is expressed as (residual density/initial density)×100. The results are summarized in Table 3 and represent the percentages for the initial samples. The percentage residual density for both the initial samples and the diluted samples showed the same degradation rate.

TABLE 3

| Dye | 1 hr exposure % residual density | 2 hrs exposure % residual density | 4 hrs exposure % residual density | 8 hrs exposure % residual density |
|---|---|---|---|---|
| Invention dye-16 | 100 | 100 | 100 | 90 |
| Reference dye-7 | 100 | 95 | 82 | 68 |
| Reference dye-8 | 100 | 100 | 95 | 75 |

The results shown in Table 3 clearly show that ink compositions with self-assembling dyes according to the present invention, containing a multiple hydrogen bonding moiety, have a significantly higher light-fastness.

Ink-jet Example 3

In this example a comparison is made between the light-fastness characteristics of some invention dyes and some reference dyes. The following compounds were involved:

Dye 21

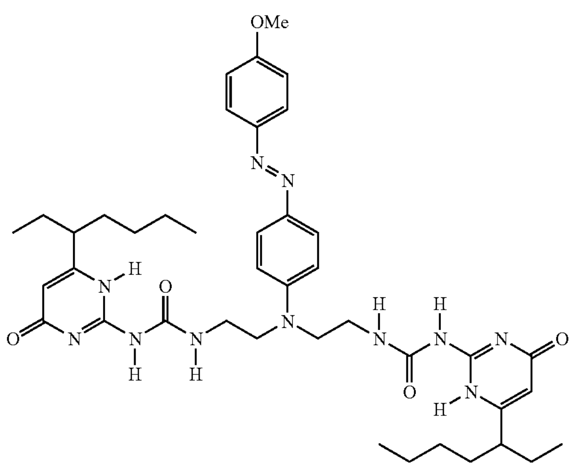

reference dye-9

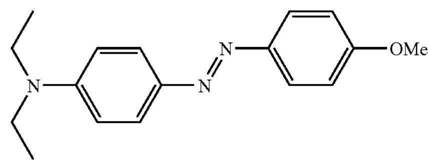

Both reference dye-9 and the invention Dye-21 were dissolved in $CH_2Cl_2$/2-methoxypropanol (1/1). Reference dye-9 was dissolved as a 0.25% solution (w/v). The invention Dye-21 was dissolved as a 0.5% solution (w/v). 1 mL of the samples was diluted with 0.75 mL 2-methoxypropanol and 0.75 mL $CH_2Cl_2$. A second sample of 1 mL was diluted with 1.75 mL 2-methoxypropanol and 2 mL $CH_2Cl_2$. For each sample 10 μl was spotted on a Polar DTR receiver (trademark from AGFA). Each sample was spotted 5 times and the average value was taken as the initial density for each dye at the start of the light-fastness test. The spotted samples were exposed during 8 hours using a Xenon-apparatus (Xenotest 150, equipped with a 7IR-filter, working in indoor mode). After one, two, four and eight hours, the density was measured again and the average density of five spots was taken as the residual density. The percentage residual density is expressed as (residual density/initial density)×100. The results are summarized in Table 4 and represent the percentages for the initial samples. The percentage residual density for both the initial samples and the diluted samples showed the same degradation rate.

TABLE 4

| Dye | 1 hr exposure % residual density | 2 hrs exposure % residual density | 4 hrs exposure % residual density | 8 hrs exposure % residual density |
|---|---|---|---|---|
| invention dye-21 | 100 | 100 | 100 | 100 |
| reference dye-9 | 92 | 85 | 77 | 55 |

The results shown in Table 4 clearly show that ink compositions with self-assembling dyes according to the present invention, containing a multiple hydrogen bonding moiety, have a significantly higher light-fastness.

Ink-jet Example 4

This example deals with ink preparation and the evaluation of some physical properties.

Solubility.

A 5% solution of Dye-6, Dye-7 and Dye-9 in butyl lactate, ethyl lactate, diacetone alcohol, propylene glycol methyl ether and tripropylene glycol methyl ether were prepared by adding the dyes to the solvents and sonicating the suspension for one hour. Clear solutions were obtained. Reference magenta dye RM1 (Table 7) was only partially soluble under the same conditions; reference cyan dye RC1 (Table 7) was soluble in butyl lactate (5%) but only partially soluble in the other solvents. Reference yellow dye RY1 (Table 7) was only soluble in methoxypropyl acetate and N-methyl pyrrolidinone.

Inks.

Table 5 shows the basic formulation, which the dyes were assessed in. The ink raw materials were placed into a plastic bottle and sonicated for one hour. The inks were then filtered to 1 μm and the physical properties measured. Table 6 shows the physical property measurements for each ink. The dyes according to the invention have similar physical ink properties and the filtration times are all good. Generally a filtration time of less than 45 seconds is expected for a dye-based ink.

TABLE 5

| Ink | % Composition w/w |
|---|---|
| Dye (Dye-6; Dye-7) | 3 |
| Vinyl chloride/vinyl acetate copolymer UCAR VAGD | 2 |
| Butyl lactate | 95 |
| Dye (Dye-9) | 3 |
| Vinyl chloride/vinyl acetate copolymer UCAR VAGD | 2 |
| Butyl lactate | 75 |
| N-Methyl Pyrrolidone | 20 |

Priming and Loading.

Inks Ink 1–6 (see table 7 for reference dyes) were tested under standard operating conditions in a Trident UltraJet printhead. The standard conditions are defined as a. 150V printhead driver
b. printhead temperature=25° C.
c. sub-pulse off
d. 354 dpi The results obtained show that all inks are easy to load and prime, and achieve good wetting of the internal architecture of the printhead. No visible air entrapment is noticed. Initial start-up is almost immediate and all channels work after maximum 4 primes. The print quality is very good on AGFA Outdoor Material (Polar DTR receiver; trademark from AGFA) and good on polyester (Melinex 347) and PVC substrates.

TABLE 6

| | Ink1/Dye-6 Cyan | Ink2/Dye-7 Magenta | Ink3/RM1 Magenta | Ink4/RC1 Cyan | Ink5/Dye-9 Yellow | Ink6/RY1 Yellow |
|---|---|---|---|---|---|---|
| Viscosity (mPa · s) | 7.70 | 8.24 | 7.15 | 8.27 | 8.44 | 7.56 |
| Surface Tension dynes/cm | 31.5 | 31.5 | 31.5 | 31.5 | 31.5 | 30 |
| Filtration Performance[1] | 27 sec. | 26 sec. | 29 sec. | 28 sec. | 33 | 33 |

[1]the filtration perfromance is the time taken to filter 15 mL of ink through a one μm filter paper using a vacuum of 200 mm Hg.

TABLE 7

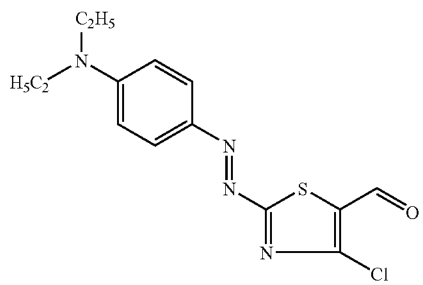

Reference Magenta-1 (RM1)

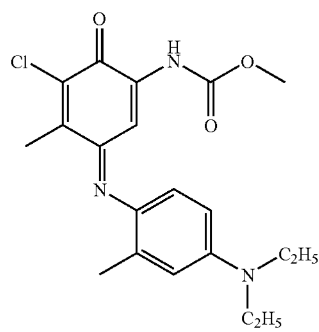

Reference Cyan-1 (RC1)

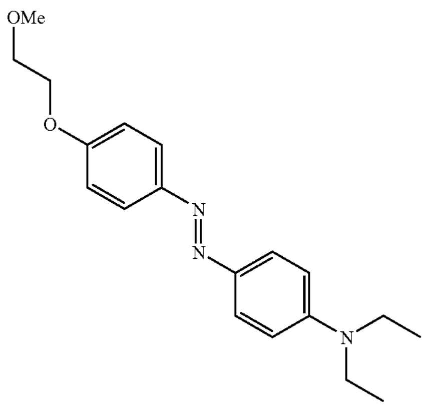

Reference Yellow-1 (RY1)

Ink-jet Example 5

A 0.02 M solution of dye-11 in $MeOH/CH_2Cl_2$/ethyl lactate 40/50/10 was diluted twice, four times, eight times and sixteen times with the same solvent mixture. The different solutions were sprayed on an AGFA POLAR DTR outdoor medium using an X-Y-plotter equipped with a sprayhead, resulting in a density wedge. A second density wedge was sprayed similar to the reference solution, using a 0.02 M solution of dye-11 in combination with 0.04 M diallylbarbituric acid as a supramolecular complement.

Both density wedges were exposed to roomlight for three months, avoiding direct sunlight on the samples. After three months exposure, the percentage density loss was measured.

Dye 11 diallylbarbituric acid
as supramolecular complement

The results are summarized in Table 8.

TABLE 8

| Sample | % density loss after three months exposure to daylight at density 1 | % density loss after three months exposure to daylight at density 1.5 |
|---|---|---|
| Dye-11 (comparative) | 55% | 17% |
| Dye-11 plus supramolecular complement (invention) | 25% | 2% |

The density wedges were also stored in the dark for three months to evaluate dark fading. At density 1.5, the reference dye lost 12% in density, while upon addition of the supramolecular complement no density loss was measured.

This example clearly illustrates the improvement in image permanence upon self-assembly of the dye and the complement.

Ink-jet Example 6

Reference Solution:

A 0.02 M solution of dye-32 in water/MeOH 90/10 was diluted twice, four times, eight times and sixteen times. A density wedge was sprayed on an AGFA POLAR DTR outdoor medium as described in the previous example.

Barbituric Acid as Supramolecular Complement:

4 moles of barbituric acid per mole dye-32 were dissolved in a 0.02 M solution of dye-32 using 2 equivalents of NaOH per mole barbituric acid. This solution was diluted and sprayed in the same way as the reference solution.

Cyanuric Acid as Supramolecular Complement:

2 moles of cyanuric acid per mole dye-32 were dissolved in a 0.02M solution of dye-32 using 2 equivalents of NaOH per mole cyanuric acid. This solution was diluted and sprayed in the same way as the reference solution.

Dye 32

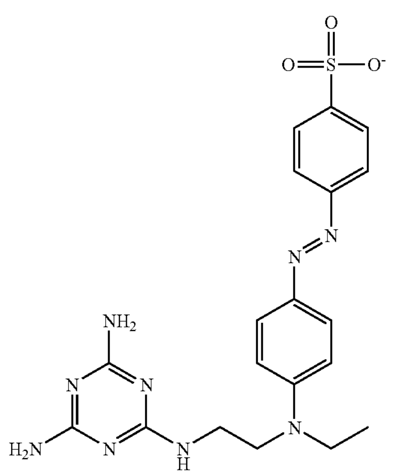

Three density wedges were prepared and exposed to Xenon light for 8 hours and the density loss at density 1 was measured after four and after eight hours of exposure.

The results are summarized in Table 9.

TABLE 9

| Sample | % density loss at density 1 after 4 hours expose | % density loss at density 1 after 8 hours exposure |
|---|---|---|
| Dye-32 (comparative) | 17% | 30% |
| Dye-32 + barbituric acid (invention) | 9% | 19% |
| Dye-32 + cyanuric acid (invention) | 8.5% | 21% |

This example clearly illustrates the improvement in image permanence upon self-assembly of the dye and the complement.

Ink-jet Example 7

A 0.02 M solution of reference dye-5, reference dye-6 and invention dye-17 were dissolved in water/MeOH 90/10 and diluted twice and five times. The solutions were spotted onto an AGFA POLAR DTR outdoor medium and exposed to Xenon light for eight hours. The % density loss at density 1 was measured after eight hours exposure. The results are summarized in Table 10.

TABLE 10

4 $Et_3N$

Dye 17

Reference dye-5

4 $Et_3N$

Reference dye-6

| Sample | % density loss after 8 hours exposure at density 1 |
|---|---|
| invention dye-17 | 1% |
| reference dye-6 | 5% |
| reference dye-5 | 20% |

This example clearly illustrates that the introduction of a self-assembling unit gives superior light fastness as compared to both the parent amino dye and the acetylated reference dye.

Ink-jet Example 8

0.02 M solutions of the invention dyes summarized in Table 11 and reference dye-9 were prepared in $CH_2Cl_2$/MeOH/ethyl lactate 50/40/10 and diluted twice, four times, eight times and sixteen times. All solutions were sprayed onto an AGFA POLAR DTR outdoor medium, resulting in a density wedge. All samples were exposed to Xenon light for eight hours and the percentage density loss after eight hours exposure was measured at density 1. All results are summarized in Table 11.

TABLE 11

Reference dye-9

| Compound | R1 | R2 | % density loss at density 1 after eight hours Xenon exposure |
|---|---|---|---|
| invention dye-21 | $CH_3(CH_2)_3CHCH_2CH_3$ | H | 24% |
| invention dye-29 | $CH_3(CH_2)_3CHCH_2CH_3$ | $CH_3$ | 29% |
| invention dye-27 | —$(CH_2)_3O(CH_2CH_2O)_3CH_3$ | H | 11% |
| invention dye-25 | —$CH_2O(CH_2CH_2O)_3CH_3$ | H | 10% |
| invention dye-28 | —$CH(CH_3)CH_2CH_2O(CH_2CH_2O)_3CH_3$ | H | 8% |
| reference dye-9 (comparative) | — | — | 51% |

From the results in Table 11 it is clear that the introduction of self-assembling units on the basic chromophore group significantly increases the light-fastness of the dyes.

Having described in detail preferred embodiments of the current invention, it will now be apparent to those skilled in the art that numerous modifications can be made therein without departing from the scope of the invention as defined in the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. An ink composition comprising at least one self-assembling dye according to formula (I)

$$(CU)_n(SAU)_m \quad (I)$$

wherein,

CU means a chromophore group with an absorption maximum between 200 nm and 2000 nm and covalently linked to SAU;

Sau means a multiple H-donor/accepting group, which can form at least three hydrogen bonds;

n and m are at least 1;

when n is greater than 1 the individual CU groups may be the same or different; and when m is greater than 1 the individual SAU groups may be the same or different.

2. Ink composition according to claim 1, wherein said ink composition further contains at least one self-assembling non-dye compound according to formula (II):

$$(SAU')_p(X)_q \quad (II)$$

wherein, SAU' means a multiple H-donor/accepting group covalently linked to X;

X represents hydrogen, a halogen, a substituted or unsubstituted alkoxy group, a substituted or unsubstituted thioalkoxy group, a substituted or unsubstituted sulphoxy group, a substituted or unsubstituted sulphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group or a heterocyclic group;

p and p are at least 1;

q is 0 or 1;

when p is greater than 1 the SAU' groups may be the same or different.

3. Ink composition according to claim 2, wherein said at least one of said self-assembling dyes present in said ink composition is capable of self-assembling with at least one of said self-assembling non-dye compounds according to formula (II) present in said ink composition.

4. Ink composition according to claim 1, wherein said ink composition contains at least two self-assembling dyes according to formula (I).

5. Ink composition according to claim 4, wherein said at least two self-assembling dyes according to formula (I) are capable of self-assembling with one another.

6. Ink composition according to claim 1, wherein the association constant $K_{ass}$ Of the self-assembling reaction between individual self-assembling dyes according to formula (I), determined by $^1$H-NMR in $CDCl_3$, is at least 2.5 $M^{-1}$.

7. An ink composition according to claim 3, wherein the association constant $K_{ass}$ of the self-assembling reaction between said at least one of said self-assembling dyes present in said ink composition with at least one of said self-assembling non-dye compounds according to formula (II) present in said ink composition, determined by $^1$H-NMR in $CDCl_3$, is at least 2.5 $M^{-1}$.

8. Ink composition according to claim 5, wherein the association constant $K_{ass}$ of the self-assembling reaction between the two self-assembling dyes according to formula (I), determined by $^1$H-NMR in $CDCl_3$, is at least 2.5 $M^{-1}$.

9. Ink composition according to claim 1 wherein said SAU group is or said SAU groups are independently selected from the group consisting of ureidopyrimidone groups, aminopyrimidine groups, aminopyridine groups, imide groups, aminotriazine groups, barbituric acid groups, urea based groups and uric acid based groups.

10. Ink composition according to claim 2 wherein said SAU' group is or said SAU' groups are independently chosen from the group consisting of ureidopyrimidone groups, aminopyrimidine groups, aminopyridine groups, imide groups, aminotriazine groups, barbituric acid groups, urea based groups and uric acid based groups.

11. Ink composition according to claim 1 wherein said ink composition is water based.

12. Ink composition according to claim 1 wherein said ink composition is solvent based.

13. Ink composition according to claim 1 wherein said ink composition is oil based.

14. Ink composition according to claim 1 wherein said ink composition is a hot melt ink.

15. Ink composition according to claim 1 wherein said ink composition is UV-curable.

16. Ink composition according to claim 6 wherein said association constant $K_{ass}$ is at least $10^2$ $M^{-1}$.

17. Ink composition according to claim 6 wherein said association constant $K_{ass}$ is at least $10^5$ $M^{-1}$.

18. Ink composition according to claim 7 wherein said association constant $K_{ass}$ is at least $10^2$ $M^{-1}$.

19. Ink composition according to claim 7 wherein said association constant $K_{ass}$ is at least $10^5$ $M^{-1}$.

20. Ink composition according to claim 8 wherein said association constant $K_{ass}$ is at least $10^2$ $M^{-1}$.

21. Ink composition according to claim 8 wherein said association constant $K_{ass}$ is at least $10^5$ $M^{-1}$.

22. Ink composition according to claim 1 wherein the concentration of self-assembling dye according to formula (I) is comprised between 0.5 wt % and 40 wt % based on the total ink weight.

23. Ink composition according to claim 11 wherein said concentration of self-assembling dye according to formula (I) is comprised between 1 wt % and 10 wt % based on the total ink weight.

24. A process for the formation of an ink-jet image comprising the step of image-wise jetting by means of an ink-jet printing apparatus onto an ink-jet recording element, comprising a support and optionally at least one ink receiving layer an ink composition comprising at least one self-assembling dye according to formula (I)

$$(CU)_n(SAU)_m \quad (I)$$

wherein,

CU means a chromophore group with an absorption maximum between 200 nm and 2000 nm and covalently linked to SAU;

SAU means a multiple H-donor/accepting group, which can form at least three hydrogen bonds;

n and m are at least 1;

when n is greater than 1 the individual CU groups may be the same or different; and when m is greater than 1 the individual SAU groups may be the same or different.

25. Process for the formation of an ink-jet image according to claim 24, wherein said ink composition further comprises a self-assembling compound according to formula (II)

$$(SAU')_p(X)_q \quad \text{(II)}$$

wherein,

SAU' means a multiple H-donor/accepting group, which can form at least three hydrogen bonds, and covalently linked to X;

X represents hydrogen, a halogen, a substituted or unsubstituted alkoxy group, a substituted or unsubstituted thioalkoxy group, a substituted or unsubstituted sulphoxy group, a substituted or unsubstituted sulphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group or a heterocyclic group;

p and p are at least 1;

q is 0 or 1;

when p is greater than 1 the SAU' groups may be the same or different.

26. Process for the formation of an ink-jet image according to claim 25, wherein said at least one of said self-assembling dyes present in said ink composition is capable of self-assembling with at least one of said self-assembling non-dye compounds according to formula (II) present in said ink composition.

27. Process for the formation of an ink-jet image according to claim 24, wherein said ink composition comprises at least two self-assembling dyes according to formula (I).

28. Process for the formation of an ink-jet image according to claim 27, wherein said at least two self-assembling dyes according to formula (I) are capable of self-assembling with one another.

29. Process for the formation of an ink-jet image according to claim 24, wherein the association constant $K_{ass}$ of the self-assembling reaction between individual self-assembling dyes according to formula (I), determined by $^1$H-NMR in $CDCl_3$, is at least 2.5 $M^{-1}$.

30. Process for the formation of an ink-jet image according to claim 26, wherein the association constant $K_{ass}$ of the self-assembling reaction between said at least one of said self-assembling dyes present in said ink composition with at least one of said self-assembling non-dye compounds according to formula (II) present in said ink composition, determined by $^1$H-NMR in $CDCl_3$, is at least 2.5 $M^{-1}$.

31. Process for the formation of an ink-jet image according to claim 28, wherein the association constant $K_{ass}$ of the self-assembling reaction between the two self-assembling dyes according to formula (I), determined by $^1$H-NMR in $CDCl_3$, is at least 2.5 $M^{-1}$.

32. Process for the formation of an ink-jet image according to claim 24, wherein said SAU group is or said SAU groups are independently selected from the group consisting of ureidopyrimidone groups, aminopyrimidine groups, aminopyridine groups, imide groups, aminotriazine groups, barbituric acid groups, urea based groups and uric acid based groups.

33. Process for the formation of an ink-jet image according to claim 25, wherein said SAU' group is or said SAU' groups are independently chosen from the group consisting of ureidopyrimidone groups, aminopyrimidine groups, aminopyridine groups, imide groups, aminotriazine groups, barbituric acid groups, urea based groups and uric acid based groups.

34. Process for the formation of an ink-jet image according to claim 24, wherein said ink composition is water based.

35. Process for the formation of an ink-jet image according to claim 24, wherein said ink composition is solvent based.

36. Process for the formation of an ink-jet image according to claim 24, wherein said ink composition is oil based.

37. Process for the formation of an ink-jet image according to claim 24, wherein said ink composition is a hot melt ink.

38. Process for the formation of an ink-jet image according to claim 24, wherein said ink composition is UV-curable.

39. Process for the formation of an ink-jet image according to claim 29, wherein said association constant $K_{ass}$ is at least $10^2$ $M^{-1}$.

40. Process for the formation of an ink-jet image according to claim 29, wherein said association constant $K_{ass}$ is at least $10^5$ $M^{-1}$.

41. Process for the formation of an ink-jet image according to claim 30, wherein said association constant $K_{ass}$ is at least $10^2$ $M^{-1}$.

42. Process for the formation of an ink-jet image according to claim 30, wherein said association constant $K_{ass}$ is at least $10^5$ $M^{-1}$.

43. Process for the formation of an ink-jet image according to claim 31, wherein said association constant $K_{ass}$ is at least $10^2$ $M^{-1}$.

44. Process for the formation of an ink-jet image according to claim 31, wherein said association constant $K_{ass}$ is at least $10^5$ $M^{-1}$.

45. Process for the formation of an ink-jet image according to claim 24, wherein the concentration of self-assembling dye according to formula (I) is comprised between 0.5 wt % and 40 wt % based on the total ink weight.

46. Process for the formation of an ink-jet image according to claim 34, wherein said concentration of self-assembling dye according to formula (I) is comprised between 1 wt % and 10 wt % based on the total ink weight.

47. An ink-jet printing apparatus comprising an ink cartridge containing an ink composition comprising at least one self-assembling dye according to formula (I)

$$(CU)_n(SAU)_m \quad \text{(I)}$$

wherein,

CU means a chromophore group with an absorption maximum between 200 nm and 2000 nm and covalently linked to SAU;

SAU means a multiple H-donor/accepting group, which can form at least three hydrogen bonds;

n and m are at least 1;

when n is greater than 1 the CU groups may be the same or different; and when m is greater than 1 the SAU groups may be the same or different.

48. Ink composition according to claim 1 wherein said at least one self-assembling dye is a dye according to formula (III):

Formula (III)

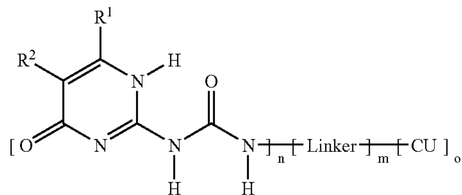

wherein

Linker represents any linking group containing at least one carbon, silicon, nitrogen, phosphorous, sulfur or oxygen atom;

CU means any dye chosen from the group consisting of an azo dye with a molar extinction coefficient larger than $10^3$ l $mol^{-1}$ $cm^{-1}$, an anthraquinone dye, a (poly) methine dye, an azomethine dye, a disazo dye, a carbonium dye, a styryl dye, a stilbene dye, a phthalocyanine dye, a coumarin dye, an aryl-carbonium dye, a nitro dye, a naphtholactam dye, a dioxazine dye, a flavin dye and a formazan dye;

n and o are the same or different and are integers having a value of at least 1; m can be zero or any integer having a value of at least 1;

$R^1$ and $R^2$ are the same or different and represent hydrogen, a halogen, a substituted or unsubstituted alkoxy group, a substituted or unsubstituted thioalkoxy group, a substituted or unsubstituted sulphoxy group, a substituted or unsubstituted sulphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group, a heterocyclic group, a chromophore group, or $R^1$ and $R^2$ represent the necessary atoms to form a ring system.

49. Ink composition according to claim 48 wherein said Linker is selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group.

* * * * *